(12) United States Patent
Stamford et al.

(10) Patent No.: US 7,304,076 B2
(45) Date of Patent: Dec. 4, 2007

(54) NEUROPEPTIDE Y Y5 RECEPTOR ANTAGONISTS

(75) Inventors: Andrew W. Stamford, Chatham Township, NJ (US); Ying Huang, East Brunswick, NJ (US); Li Guoqing, Staten Island, NY (US)

(73) Assignee: Schering Corporation, Kenilworth, NJ (US)

( * ) Notice: Subject to any disclaimer, the term of this patent is extended or adjusted under 35 U.S.C. 154(b) by 170 days.

(21) Appl. No.: 10/692,559

(22) Filed: Oct. 24, 2003

(65) Prior Publication Data

US 2004/0102474 A1    May 27, 2004

Related U.S. Application Data

(62) Division of application No. 10/202,239, filed on Jul. 24, 2002, now Pat. No. 6,667,319.

(60) Provisional application No. 60/308,433, filed on Jul. 26, 2001.

(51) Int. Cl.
*A61K 31/445* (2006.01)
*C07D 401/12* (2006.01)

(52) U.S. Cl. ........................ 514/316; 546/186
(58) Field of Classification Search ................ 514/316; 546/186
See application file for complete search history.

(56) References Cited

U.S. PATENT DOCUMENTS

| 4,405,644 A | 9/1983 | Kabbe et al. .................. 564/48 |
| 4,623,662 A | 11/1986 | DeVries ...................... 514/596 |

FOREIGN PATENT DOCUMENTS

| WO | WO 96/16542 | 6/1996 |
| WO | WO 00/27845 | 5/2000 |

OTHER PUBLICATIONS

Ko et al. "Preparation of ureidocyclohexaylmethyl . . . " CA 142:74455 (2004).*
Bonjouklian et al. "Preparation of N-isoxazoloquinolinyl . . . " Ca 135:472724 (2001).*
Murray et al. "Preparation of heteroaryl ureas . . . " CA 143:153365 (2005).*
Kushi et al. "Obesity and mild hyperinsulinemia . . . " CA 130:192212 (1999).*
Mashiko et al. "Characterization of Neuropeptide Y . . . " Endocrinology 144(5)1793-1801 (2003).*
Merck Mannual on "metabolic disorder" from web (2006).*
Billington et al., Am J. Physiol., 260, R321, 1991.
Gehlert, D., Proc. Soc. Exp. Biol. Med., 218, 7, 1998.
Gerald, C. et al., Nature, 1996, 382, 168.
Hwa, J. et al., Am. J. Physiol., 277 (46), R1428, 1999.
Michel, M. et al., Pharmacol. Rev., 50, 143, 1998.
Stanley, B. and Leibowitz, S., Proc. Natl. Acad. Sci. USA 82: 3940-3943, 1985.
Wahlestedt, C., and Reis, D.J., Ann. Rev. Pharmacol. Toxicol., 32:309-352, 1993.

* cited by examiner

*Primary Examiner*—Celia Chang
(74) *Attorney, Agent, or Firm*—William Y. Lee; Palaiyur S. Kalyanaraman

(57) ABSTRACT

The present invention discloses compounds which, are novel receptor antagonists for NPY Y5 as well as methods for preparing such compounds. In another embodiment, the invention discloses pharmaceutical compositions comprising such NPY Y5 receptor antagonists as well as methods of using them to treat obesity, metabolic disorders, eating disorders such as hyperphagia, and diabetes.

10 Claims, No Drawings

NEUROPEPTIDE Y Y5 RECEPTOR ANTAGONISTS

CROSS REFERENCE TO RELATED APPLICATIONS

This application claims the benefit of U.S. Provisional Application No. 60/308,433 filed on Jul. 26, 2001 and U.S. Ser. No. 10/202,239 filed on Jul. 24, 2002 now U.S. Pat. No. 6,667,319.

FIELD OF THE INVENTION

The present invention relates to neuropeptide Y Y5 receptor antagonists useful in the treatment of obesity and eating disorders, pharmaceutical compositions containing the compounds, and methods of treatment using the compounds.

BACKGROUND OF THE INVENTION

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev., 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y5 receptor subtype. The isolation and characterization of the NPY Y5 receptor subtype has been reported (Gerald, C. et al., Nature, 1996, 382, 168; Gerald, C. et al. WO 96/16542). Additionally, it has been reported that activation of the NPY Y5 receptor by administration of the Y5—selective agonist [D-Trp$^{32}$]NPY to rats stimulates feeding and decreases energy expenditure (Gerald, C. et al., Nature, 1996, 382, 168; Hwa, J. et al., Am. J. Physiol., 277 (46), R1428, 1999). Hence, compounds that block binding of NPY to the NPY Y5 receptor subtype should have utility in the treatment of obesity, disorders such as, bulimia nervosa, anorexia nervosa, and in the treatment of disorders associated with obesity such as type II diabetes, insulin resistance, hyperlipidemia, and hypertension.

PCT patent application WO 00/27845 describes a class of compounds, characterized therein as spiro-indolines, said to be selective neuropeptide Y Y5 receptor antagonists and useful for the treatment of obesity and the complications associated therewith. Urea derivatives indicated as possessing therapeutic activity are described in U.S. Pat. Nos. 4,623,662 (antiatherosclerotic agents) and 4,405,644 (treatment of lipometabolism).

Provisional application, U.S. Ser. No. 60/232,255 describes a class of substituted urea neuropeptide Y Y5 receptor antagonists.

SUMMARY OF THE INVENTION

In one embodiment, this invention provides novel urea compounds having NPY Y5 receptor antagonist activity. In an embodiment of the invention is a compound represented by the structural formula

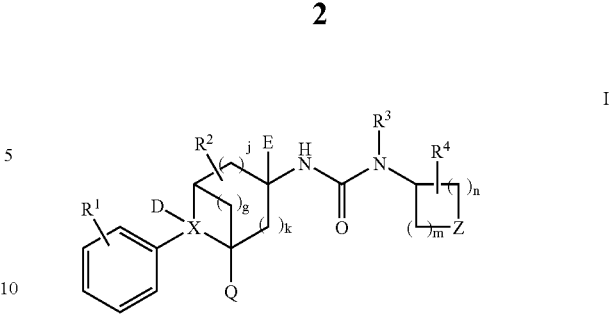

I or a pharmaceutically acceptable salt or solvate thereof, wherein:

X is independently N or C;

Z is independently NR$^8$ or CR$^3$R$^9$;

D is independently H, —OH, -alkyl or substituted -alkyl with the proviso that when X is N, D and the X-D bond are absent;

E is independently H, -alkyl or substituted -alkyl, or D and E can independently be joined together via a —(CH$_2$)$_p$- bridge;

Q is independently H, -alkyl or substituted -alkyl, or D, X, Q and the carbon to which Q is shown attached can jointly form a 3 to 7-membered ring;

g, j, k, m and n can be the same or different and are independently selected;

g is 0 to 3 and when g is 0, the carbons to which (CH$_2$)$_g$ is shown connected are no more linked;

j and k are independently 0 to 3 such that the sum of j and k is 0, 1, 2 or 3;

m and n are independently 0 to 3 such that the sum of m and n is 1, 2, 3, 4 or 5;

p is 1 to 3;

R$^1$ is 1 to 5 substituents which can be the same or different, each R$^1$ being independently selected from the group consisting of hydrogen, hydroxy, halogen, haloalkyl, -alkyl, substituted -alkyl, -cycloalkyl, CN, alkoxy, cycloalkoxy, alkylthio, cycloalkylthio, —NR$^5$R$^6$, —NO$_2$, —CONR$^5$R$^6$, —NR$^5$COR$^6$, —NR$^5$CONR$^5$R$^6$ where the two R$^5$ moieties can be the same or different, —NR$^6$C(O) OR$^7$, —C(O)OR$^6$, —SOR$^7$, —SO$_2$R$^7$, —SO$_2$NR$^5$R$^6$, aryl and heteroaryl;

R$^2$ is 1 to 6 substituents which can be the same or different, each R$^2$ being independently selected from the group consisting of hydrogen, -alkyl, substituted -alkyl, alkoxy, and hydroxy, with the proviso that when X is N and R$^2$ is hydroxy or alkoxy, R$^2$ is not directly attached to a carbon adjacent to X;

R$^3$ is independently hydrogen, -alkyl or substituted -alkyl;

R$^4$ is 1 to 6 substituents which can be the same or different, each R$^4$ being independently selected from hydrogen, -alkyl, substituted -alkyl, alkoxy, and hydroxy, with the proviso that when Z is NR$^8$ and R$^4$ is hydroxy or alkoxy, R$^4$ is not directly attached to a carbon adjacent to the NR$^8$;

R$^5$ and R$^6$ are independently hydrogen, -alkyl, substituted -alkyl or -cycloalkyl;

R$^7$ is independently -alkyl, substituted -alkyl or -cycloalkyl;

R$^8$ is independently selected from the group consisting of hydrogen, -alkyl, substituted -alkyl, -cycloalkyl, -alkylcycloalkyl, aryl, heteroaryl, aralkyl, heteroaralkyl, —SO$_2$R$^{10}$, —SO$_2$NR$^5$R$^{11}$, —C(O)R$^{11}$, —C(O)NR$^5$R$^{11}$ and —C(O) OR$^{10}$;

R$^9$ is independently hydrogen, -alkyl, substituted -alkyl, hydroxy, alkoxy, —NR$^5$R$^{11}$, aryl, or heteroaryl; or R$^3$ and R$^9$ can be joined together and with the carbon to which they are attached form a carbocyclic or heterocyclic ring having 3 to 7 ring atoms;

R$^{10}$ is -alkyl, substituted -alkyl, -cycloalkyl, -alkylcycloalkyl, aryl or heteroaryl; and R$^{11}$ is independently hydrogen, -alkyl, substituted -alkyl, -cycloalkyl, aryl or heteroaryl.

The above statement "when g is 0, the carbons to which (CH$_2$)$_g$ is shown connected are no more linked" means that when g is 0, then the structural component:

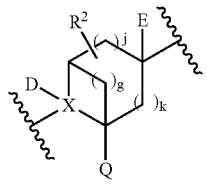

shown in formula I above becomes:

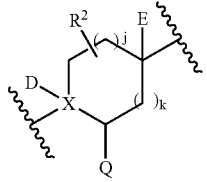

Ureas of formula I or formula III are highly selective, high affinity NPY Y5 receptor antagonists useful for the treatment of obesity.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of formula I or formula III thereof, or a pharmaceutically acceptable salt or solvate of said compound, and a pharmaceutically acceptable carrier.

DETAILED DESCRIPTION

The present invention relates to compounds that are represented by structural formula I or formula III or a pharmaceutically acceptable salt or solvate thereof, wherein the various moieties are as described above. The compounds of formula I or formula III can be administered as racemic mixtures or enantiomerically pure compounds.

In a preferred embodiment of the invention is a compound of formula I or a pharmaceutically acceptable salt or solvate thereof, wherein:

R$^1$ is 1 to 5 substituents which can be the same or different, each R$^1$ being independently selected from the group consisting of Cl, Br, I or F;

X is N;

D is absent and the X-D bond is absent;

E is H;

g is 0;

j is 1;

k is 1;

m is 2;

n is 2;

R$^2$ is H;

R$^3$ is methyl;

R$^4$ is H;

and

Z is NR$^8$, where R$^8$ is independently selected from the group consisting of hydrogen, -alkyl, substituted -alkyl, -cycloalkyl, -alkylcycloalkyl, aryl, heteroaryl, aralkyl, heteroaralkyl, —SO$_2$R$^{10}$, —SO$_2$NR$^5$R$^{11}$, —C(O)R$^{11}$, —C(O)NR$^5$R$^{11}$ and —C(O)OR$^{10}$.

A preferred embodiment of the present invention is a compound of formula II or a pharmaceutically acceptable salt or solvate thereof, wherein:

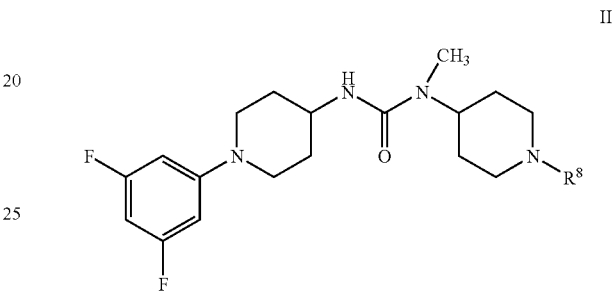

wherein R$^8$ is defined as herein in the Detailed Description in Table 1.

An additional preferred embodiment of the present invention is a compound of formula III or a pharmaceutically acceptable salt or solvate thereof, wherein:

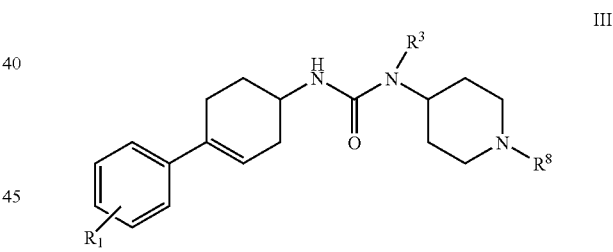

wherein

R$^1$ is 1 to 5 substituents which can be the same or different, each R$^1$ being independently selected from the group consisting of hydrogen, hydroxy, halogen, haloalkyl, -alkyl, substituted -alkyl, -cycloalkyl, CN, alkoxy, cycloalkoxy, alkylthio, cycloalkylthio, —NR$^5$R$^6$, —NO$_2$, —CONR$^5$R$^6$, —NR$^5$COR$^6$, —NR$^5$CONR$^5$R$^6$ where the two R$^5$ moieties can be the same or different, —NR$^6$C(O)OR$^7$, —C(O)OR$^6$, —SOR$^7$, —SO$_2$R$^7$, —SO$_2$NR$^5$R$^6$, aryl and heteroaryl;

R$^3$ is independently hydrogen or -alkyl; and

R$^8$ is independently selected from the group consisting of hydrogen, -alkyl, substituted -alkyl, -cycloalkyl, -alkylcycloalkyl, aryl, heteroaryl, aralkyl, heteroaralkyl, —SO$_2$R$^{10}$, —SO$_2$NR$^5$R$^{11}$, —C(O)R$^{11}$, —C(O)NR$^5$R$^{11}$ and —C(O)OR$^{10}$.

A further preferred group of compounds are compounds of formula III selected from the group consisting of

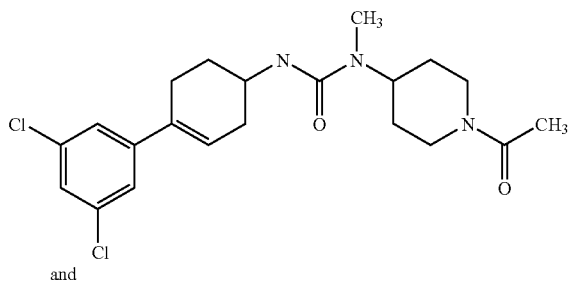

and

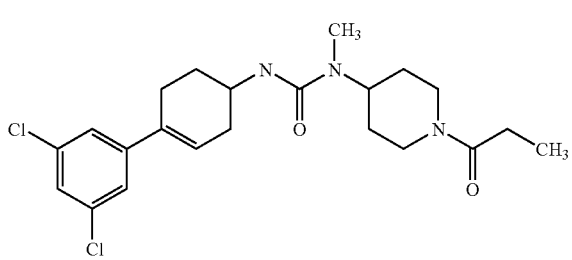

or a pharmaceutically acceptable salt or solvate of said compound.

An additional preferred embodiment of the present invention is a compound of formula IV, wherein

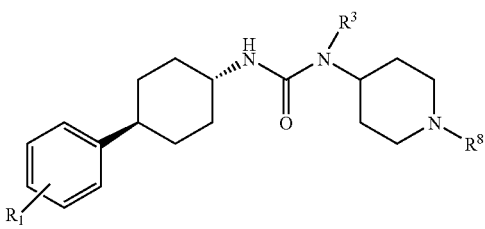

IV or a pharmaceutically acceptable salt or solvate there of, wherein $R^1$ is 1 to 5 substituents which can be the same or different, each $R^1$ being independently selected from the group consisting of hydrogen, hydroxy, halogen, haloalkyl, -alkyl, substituted -alkyl, -cycloalkyl, CN, alkoxy, cycloalkoxy, alkylthio, cycloalkylthio, —$NR^5R^6$, —$NO_2$, —$CONR^5R^6$, —$NR^5COR^6$, —$NR^5CONR^5R^6$ where the two $R^5$ moieties can be the same or different, —$NR^6C(O)OR^7$, —$C(O)OR^6$, —$SOR^7$, —$SO_2R^7$, —$SO_2NR^5R^6$, aryl and heteroaryl;

$R^3$ is independently hydrogen or -alkyl;

and $R^8$ is independently selected from the group consisting of hydrogen, -alkyl, substituted -alkyl, -cycloalkyl, -alkylcycloalkyl, aryl, heteroaryl, aralkyl, heteroaralkyl, —$SO_2R^{10}$, —$SO_2NR^5R^{11}$, —$C(O)R^{11}$, —$C(O)NR^5R^{11}$ and —$C(O)OR^{10}$.

A set of preferred compounds are listed below in the Detailed Description in Tables 2 and 3, among other preferred compounds.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other mammals.

"Mammal" means humans and other animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, -alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and -cycloalkyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, —OCF₃, —OCOalkyl, —OCOaryl, —CF₃, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl.

"Alkylaryl" means an alkyl-aryl-group in which the alkyl and aryl are as previously described. Preferred alkylaryls comprise a lower alkyl group. A non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)-group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)-group in which the aryl group is as previously described. The bond to the parent moiety is through the carbonyl. Non-limiting examples of suitable groups include benzoyl and 1- and 2-naphthoyl.

"Alkoxy" means an alkyl-O-group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O-group in which the aryl group is as previously described. Non-limiting examples of suitable aryloxy groups include phenoxy and naphthoxy. The bond to the parent moiety is through the ether oxygen.

"Alkylthio" means an alkyl-S-group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S-group in which the aryl group is as previously described. Non-limiting examples of suitable arylthio groups include phenylthio and naphthylthio. The bond to the parent moiety is through the sulfur.

"Aralkylthio" means an aralkyl-S-group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—CH$_3$, —C(O)—CH$_2$CH$_3$ and the like.

"Aryloxycarbonyl" means an aryl-O—C(O)-group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)-group. Non-limiting example of a suitable aralkoxycarbonyl group is benzyloxycarbonyl. The bond to the parent moiety is through the carbonyl.

"Alkylsulfonyl" means an alkyl-S(O$_2$)-group. Preferred groups are those in which the alkyl group is lower alkyl. The bond to the parent moiety is through the sulfonyl.

"Alkylsulfinyl" means an alkyl-S(O)-group. Preferred groups are those in which the alkyl group is lower alkyl. The bond to the parent moiety is through the sulfinyl.

"Arylsulfonyl" means an aryl-S(O$_2$)-group. The bond to the parent moiety is through the sulfonyl.

"Arylsulfinyl" means an aryl-S(O)-group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of compound of the present invention effective to treat a mammal (e.g., human) having a disease or condition mediated by Y Y5, and thus producing the desired therapeutic effect.

The compounds of formula I or formula III form salts which are also within the scope of this invention. Reference to a compound of formula I or formula III, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I or formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of formula I or formula III may be formed, for example, by reacting a compound of formula I or formula III with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I or formula III, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers, or racemates of the inventive compounds.

When any variable (e.g., aryl, heterocycle, $R_1$, etc.) occurs more than one time in any constituent or in formula I or formula III, its definition on each occurrence is independent of its definition at every other occurrence. Also, combinations of substituents and/or variables are permissible only if such combinations result in stable compounds.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I or formula III.

Compounds of formula I or formula III can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I or formula III may form pharmaceutically acceptable salts with organic and inorganic acids. For example, pyrido-nitrogen atoms may form salts with strong acids, while tertiary amino groups may form salts with weaker acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

A further group of preferred compounds are those listed below in Table 2.

TABLE 2

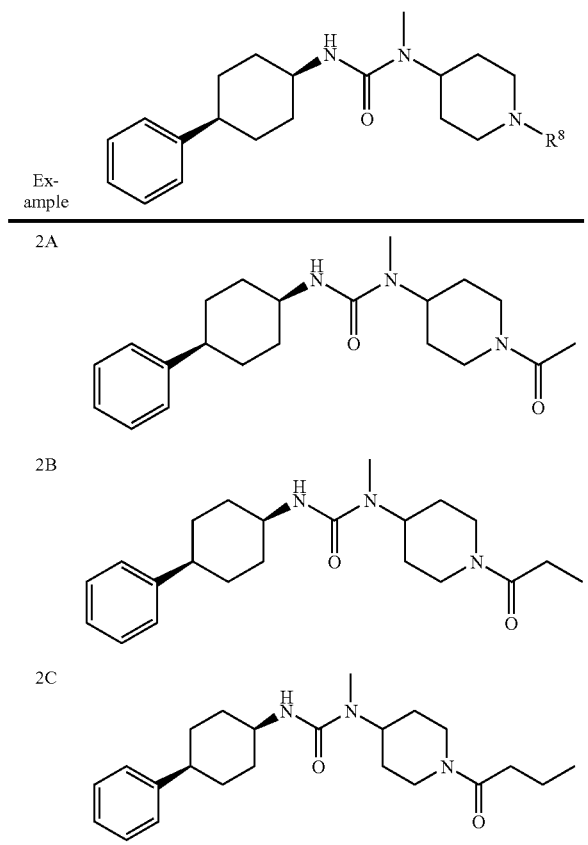

| Example | |
|---|---|
| 2A | |
| 2B | |
| 2C | |

TABLE 2-continued
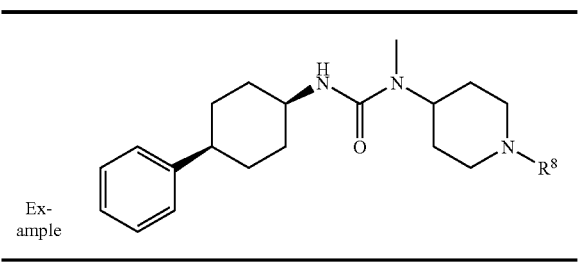
| Example | |
|---|---|
| 2D | 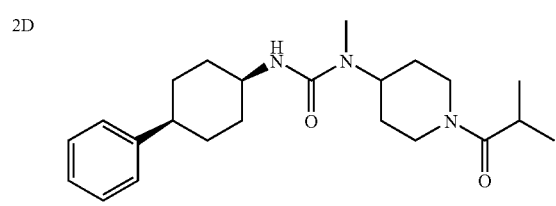 |
| 2E | 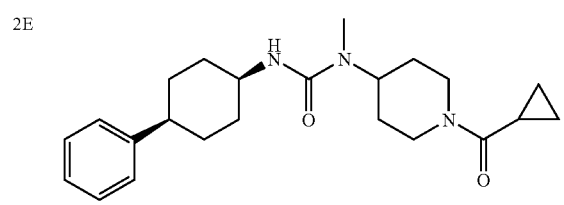 |
| 2F | 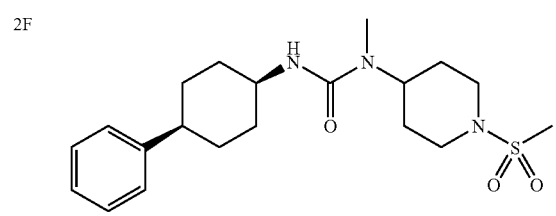 |
| 2G | 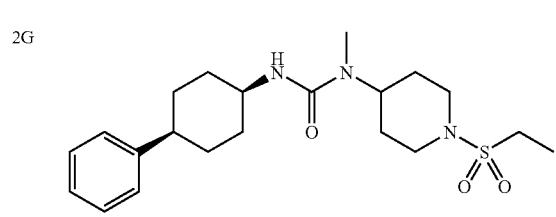 |
| 2H | 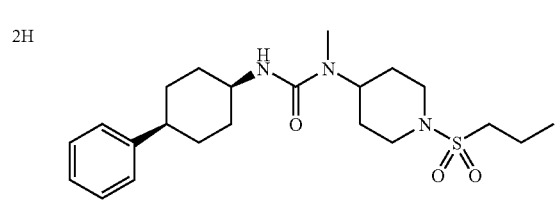 |
| 2I | 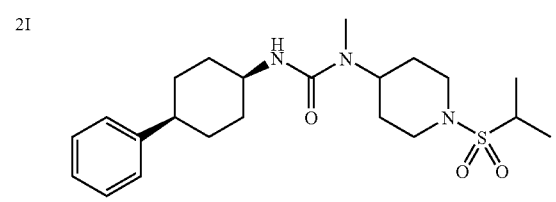 |
TABLE 2-continued
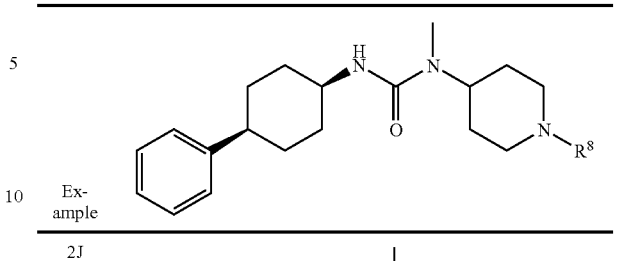
| Example | |
|---|---|
| 2J | 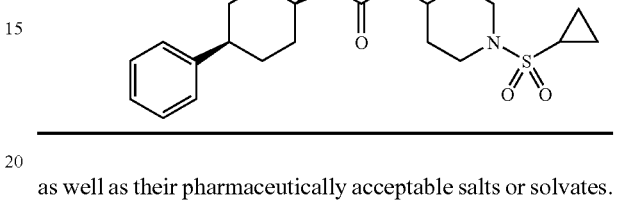 |
as well as their pharmaceutically acceptable salts or solvates.
An even further preferred group of compounds are those listed below in Table 3.
TABLE 3
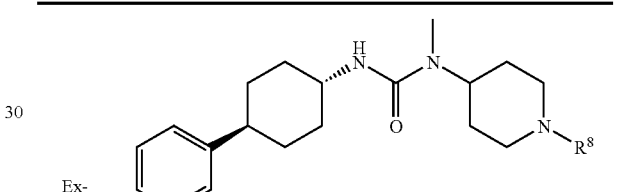
| Example | |
|---|---|
| 3A | 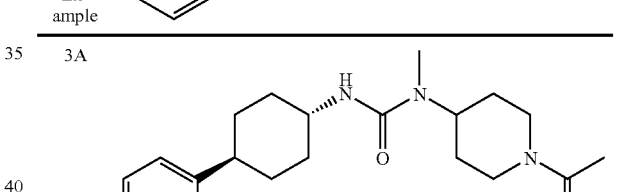 |
| 3B | 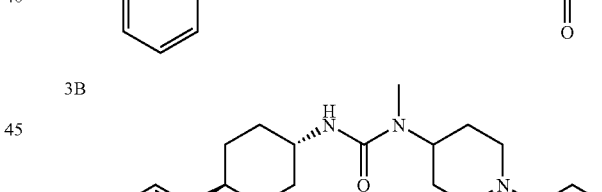 |
| 3C | 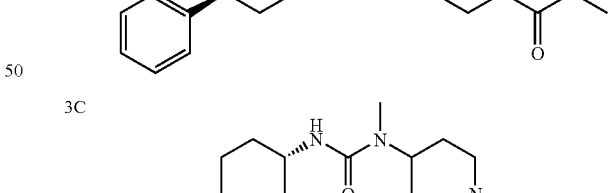 |
| 3D | 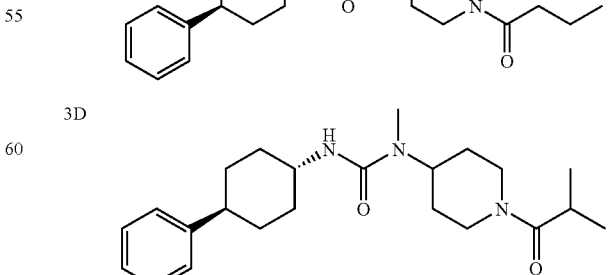 |

TABLE 3-continued
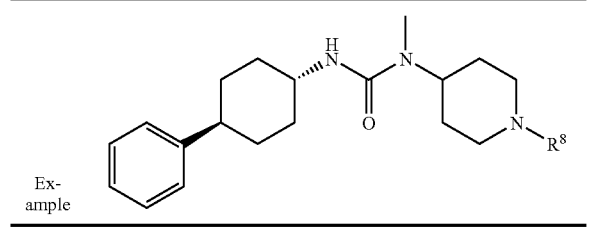
Example 3E
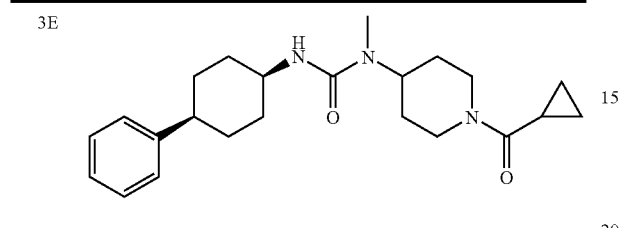
3F
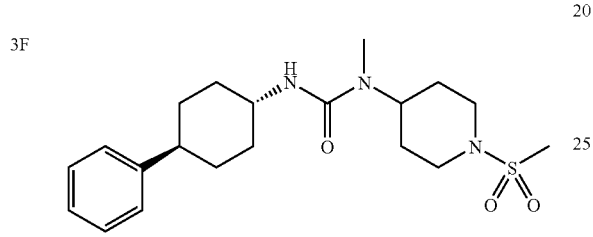
3G
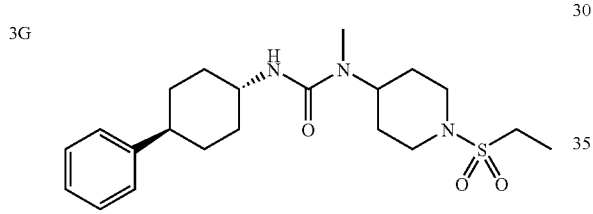
3H
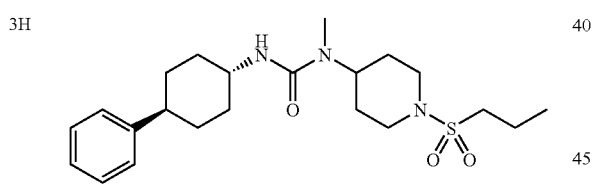
3I
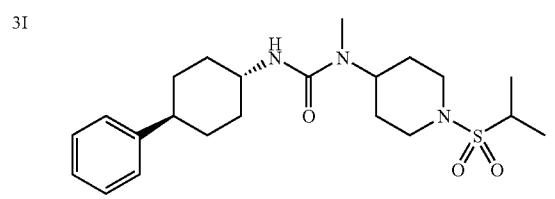
3J
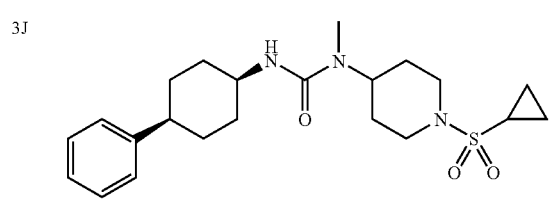
as well as their pharmaceutically acceptable salts or solvates.
An even further group of preferred compounds are compounds from the group consisting of:
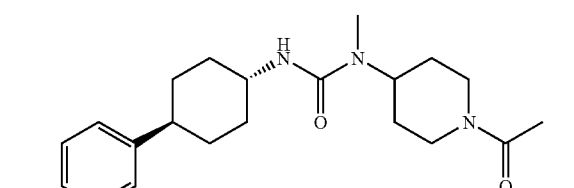
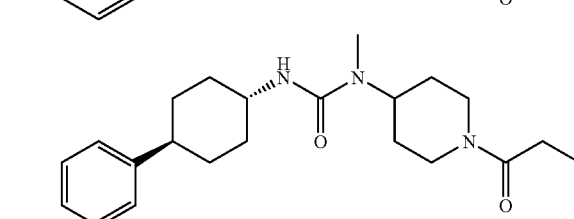
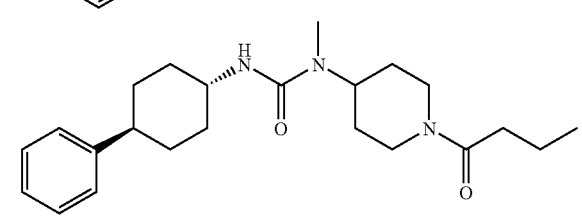
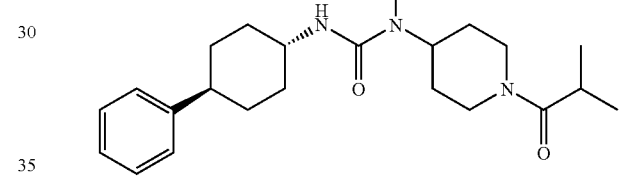
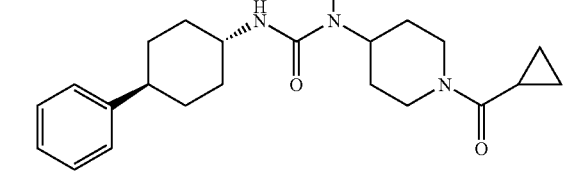
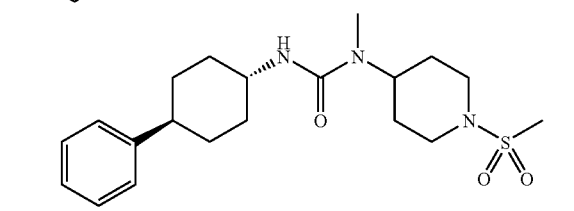
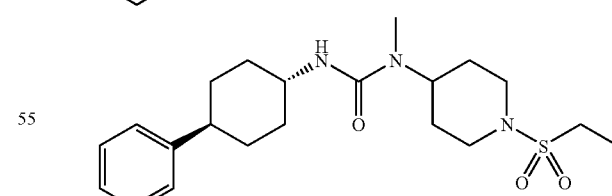
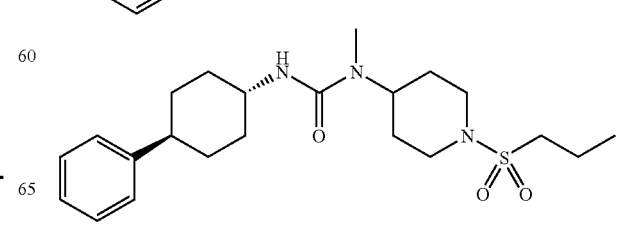

-continued
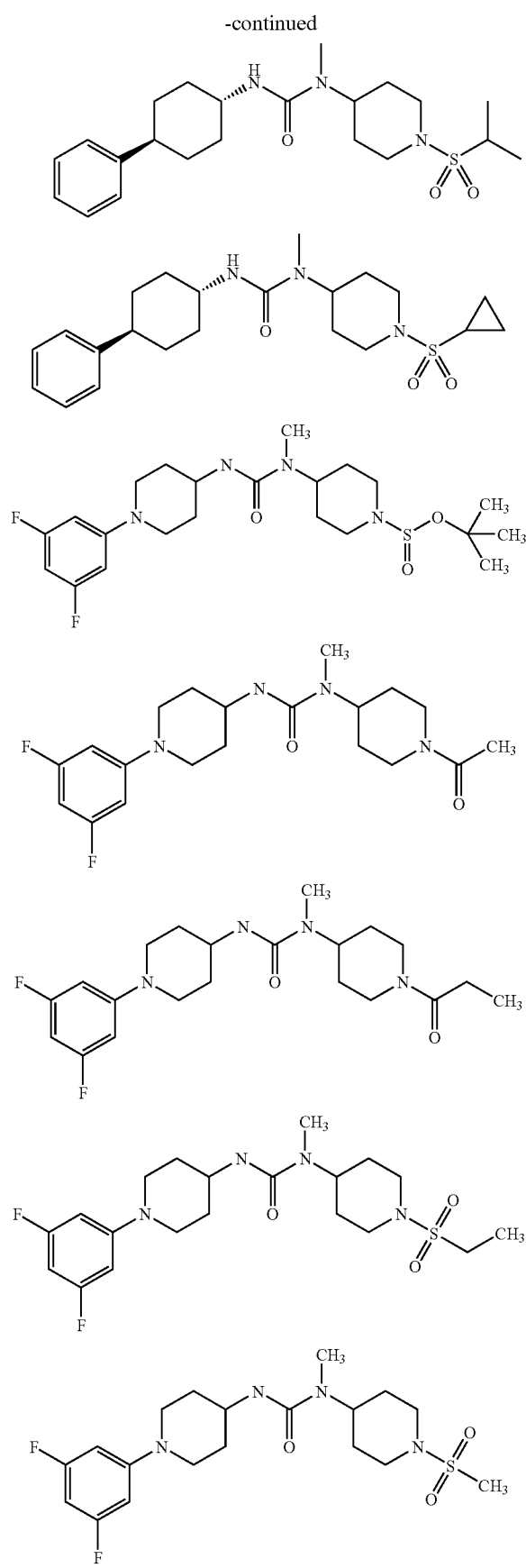
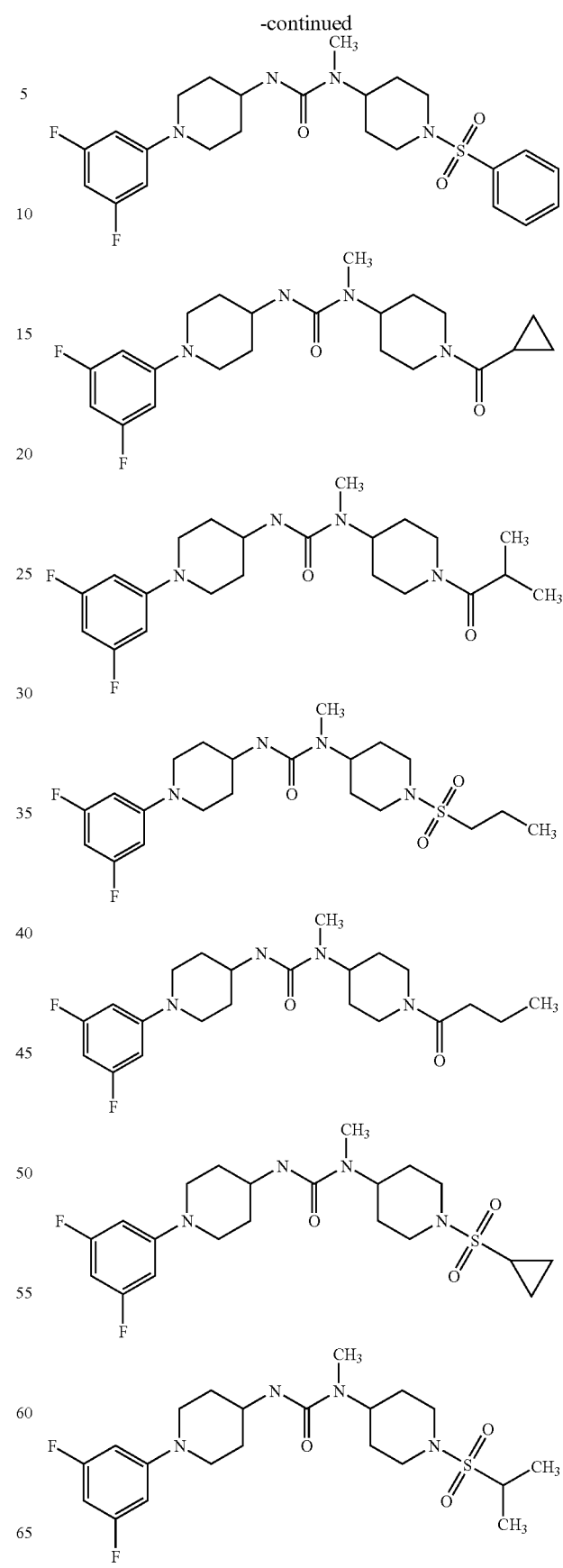

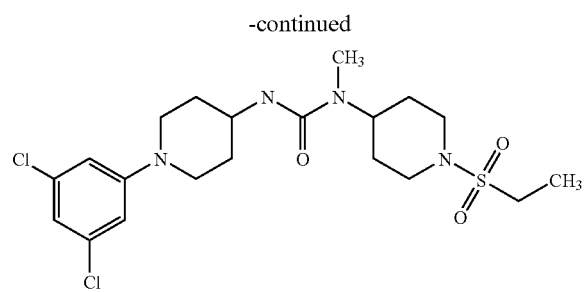
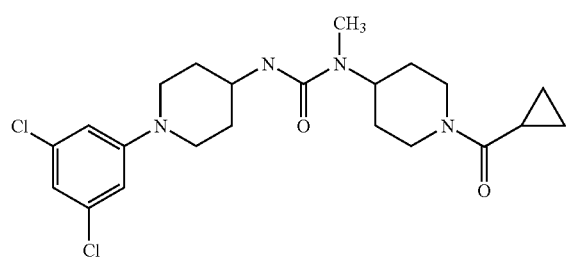
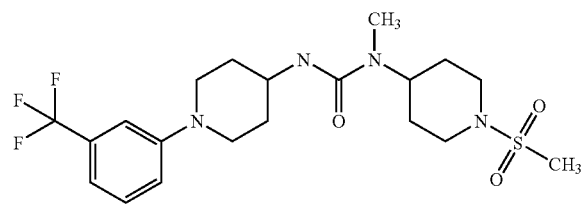
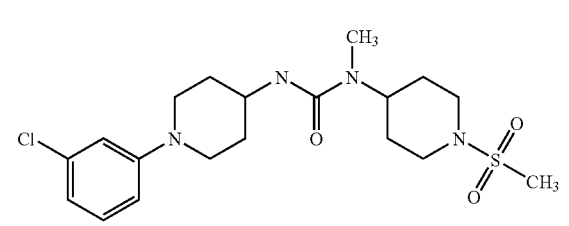
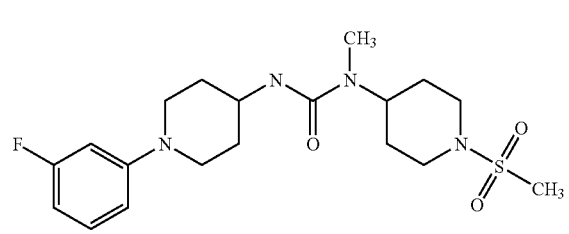
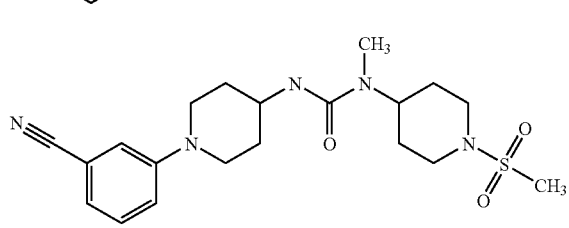
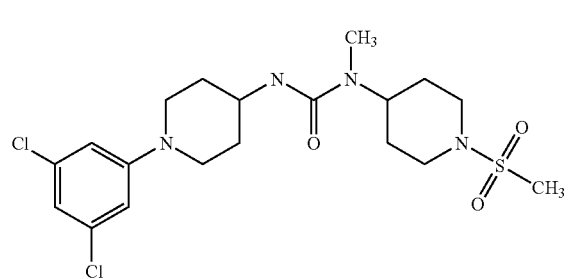
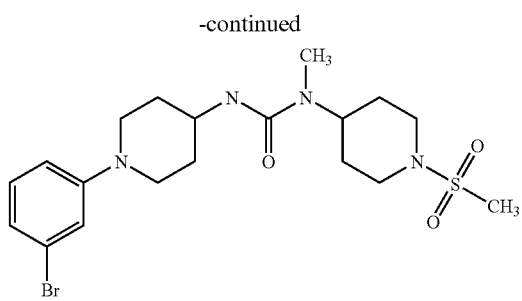
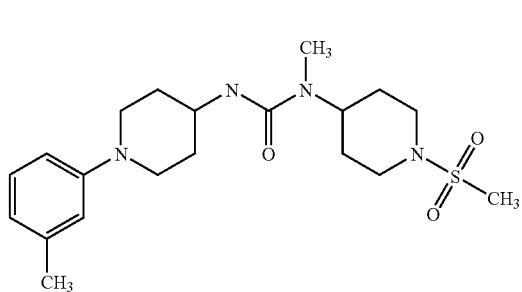
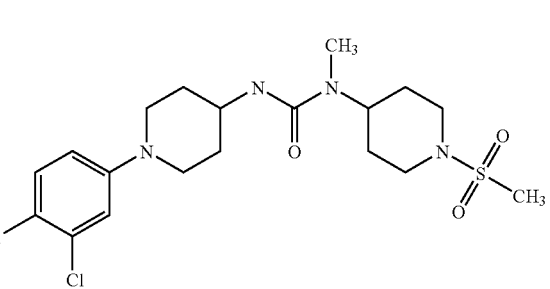
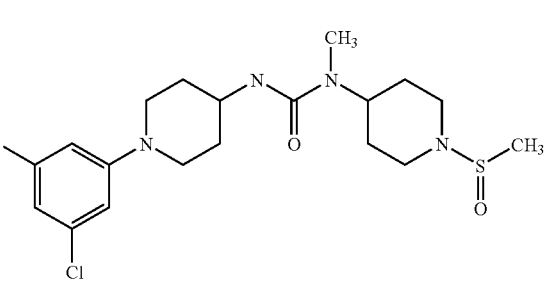
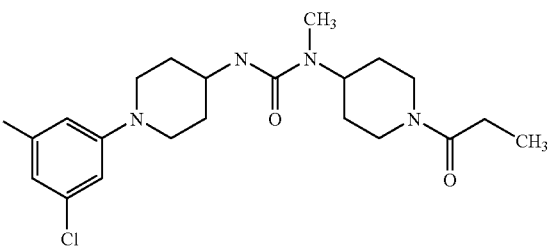
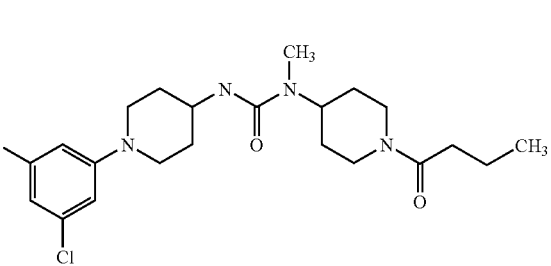

-continued
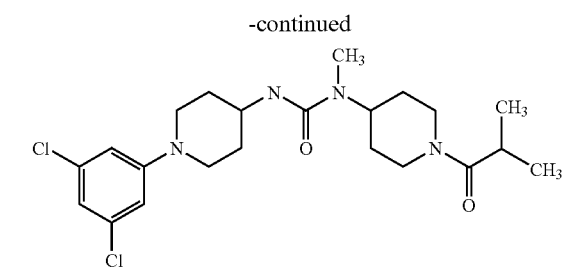
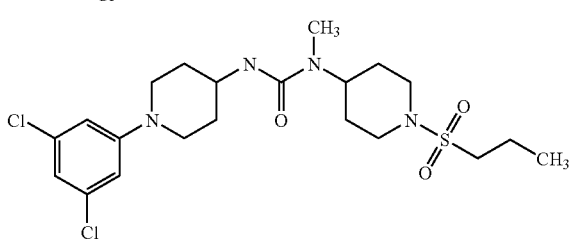
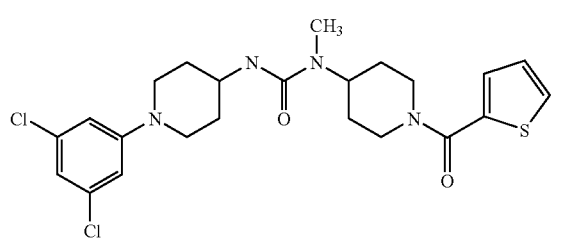
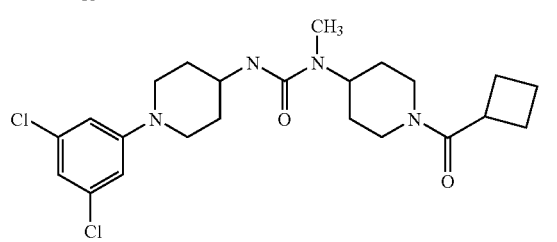
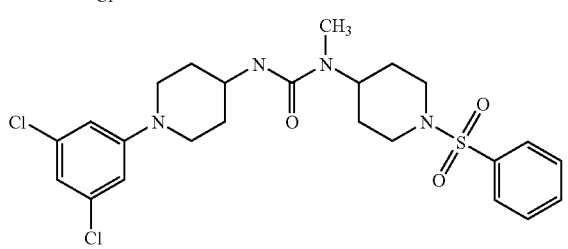
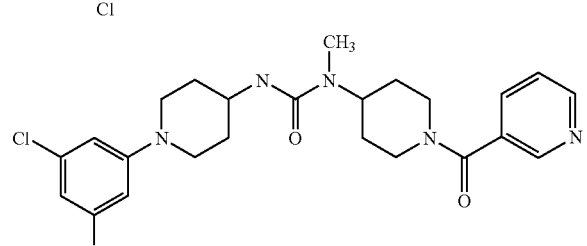
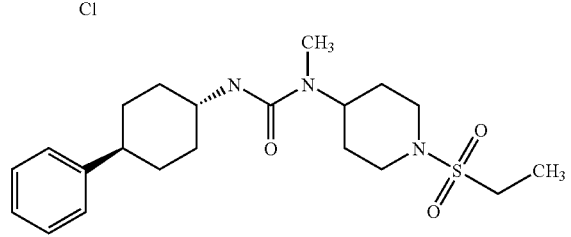
-continued
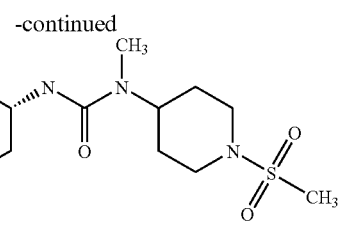
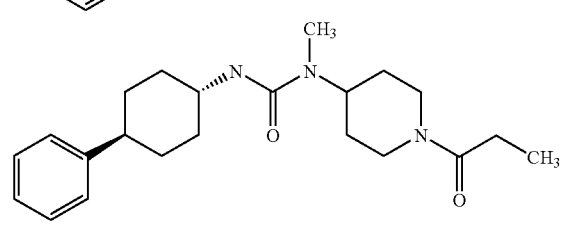
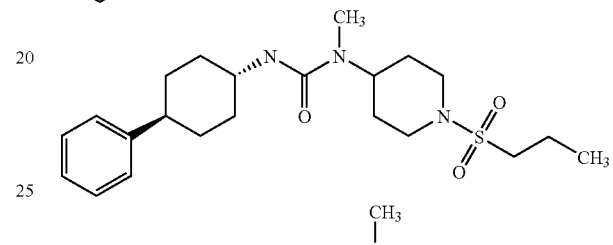
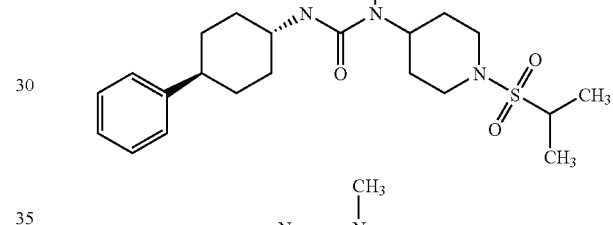
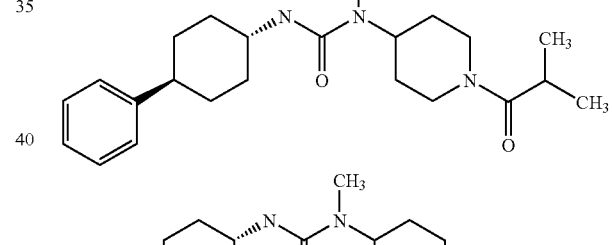
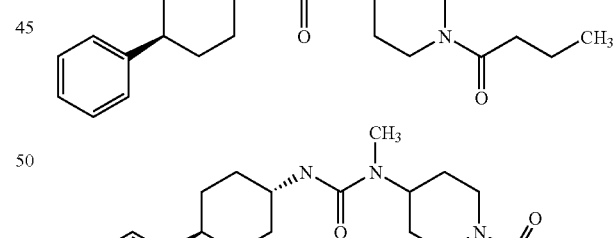
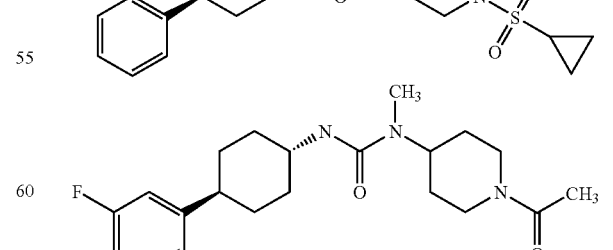

-continued
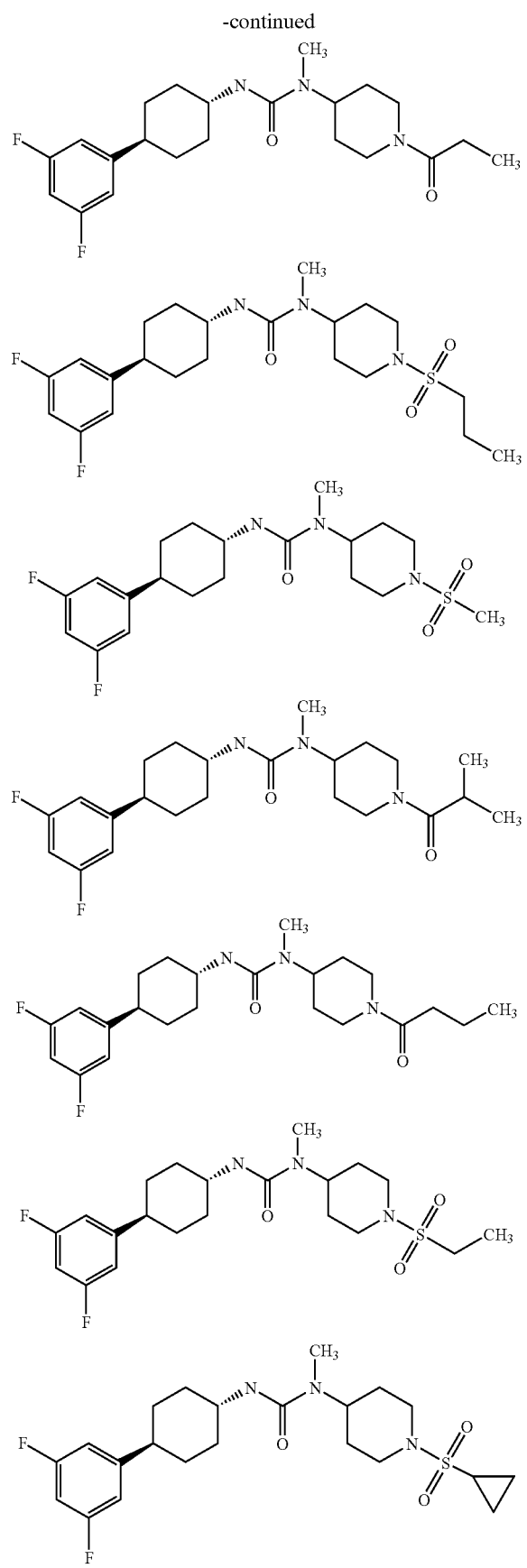
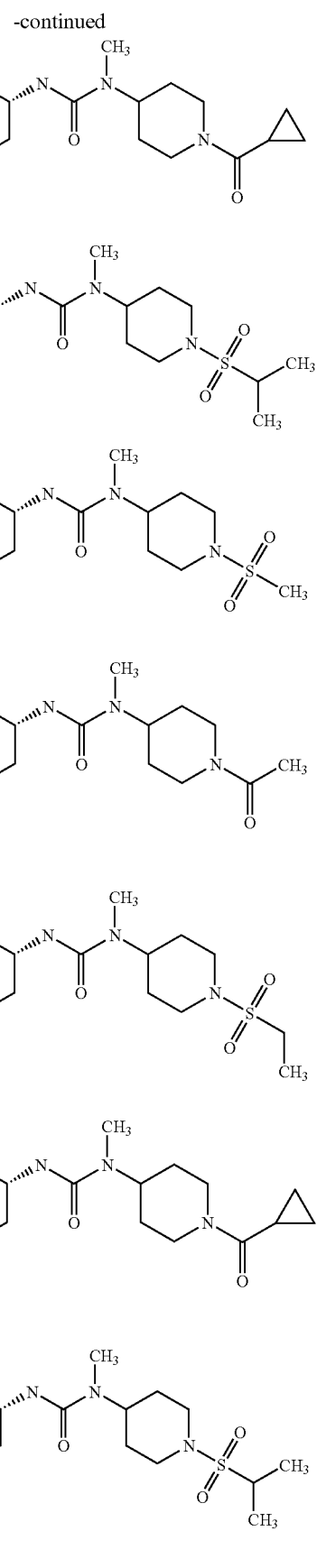

-continued
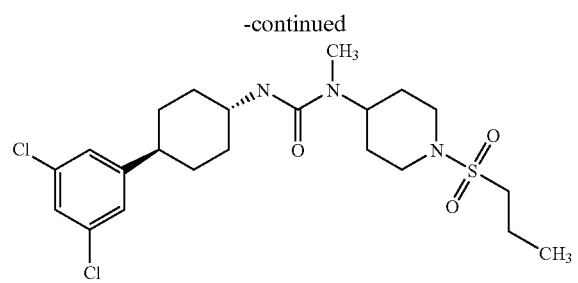
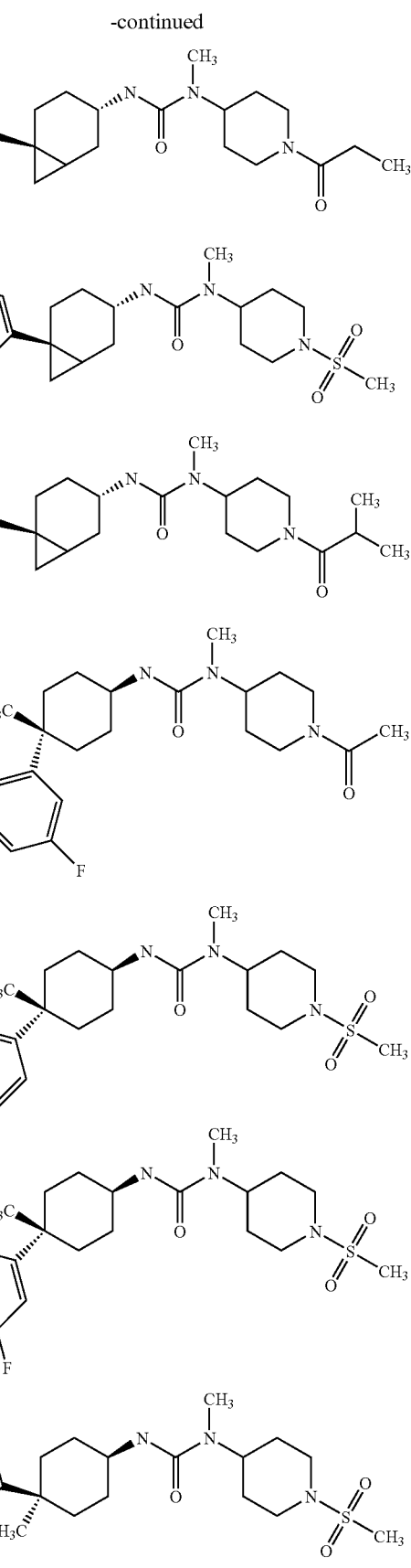

-continued
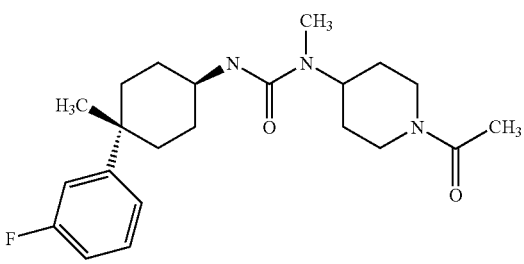
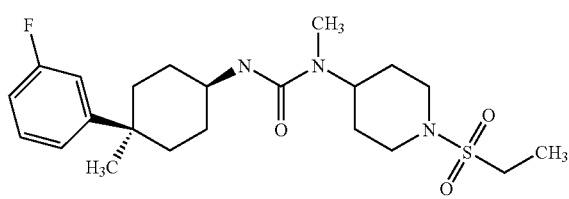
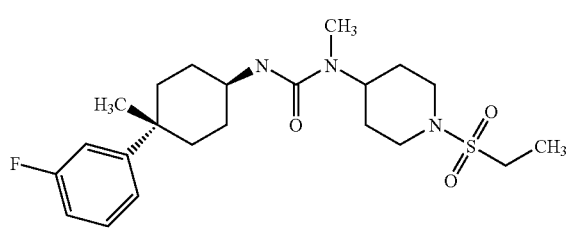
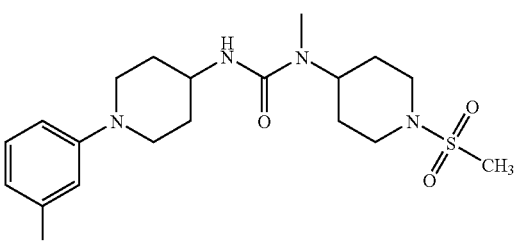
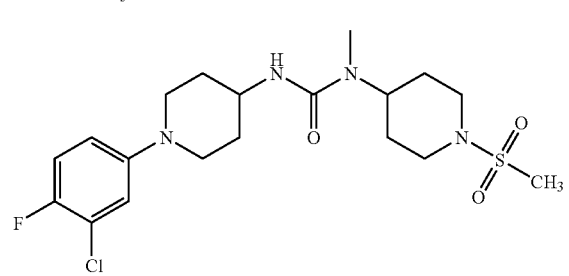
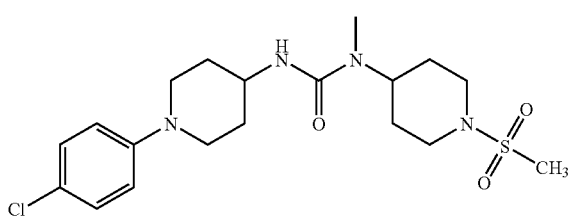
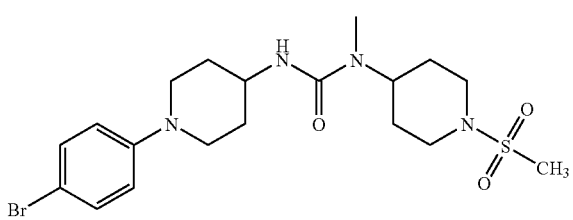
-continued
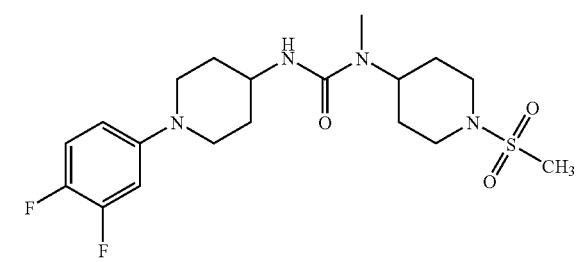
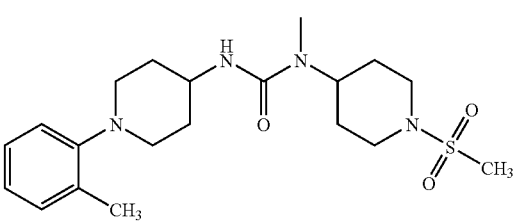
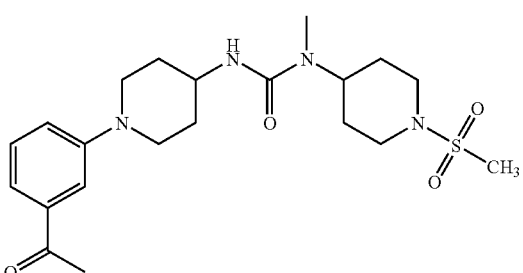
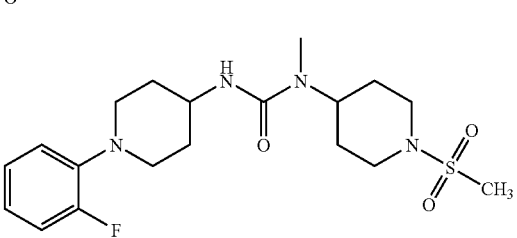
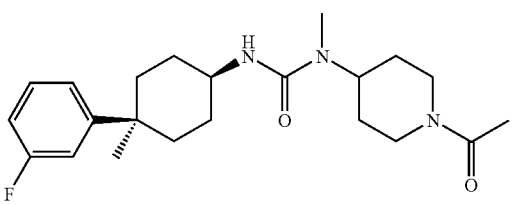
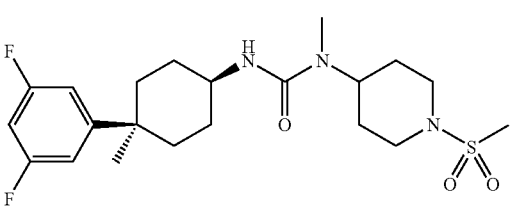
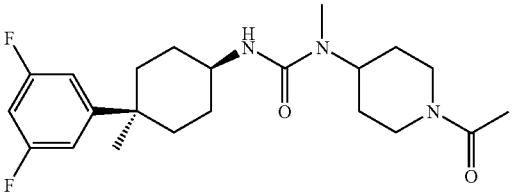

-continued

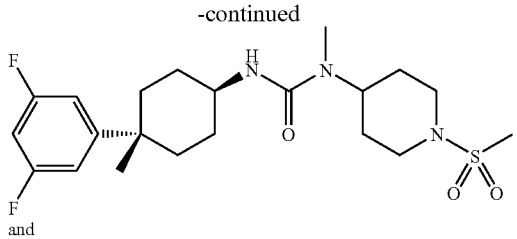
and

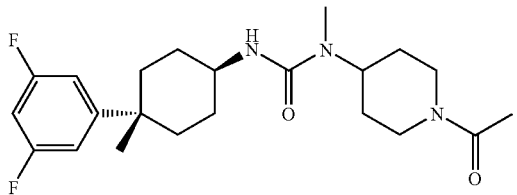

as well as their pharmaceutically acceptable salts or solvates.

Another aspect of this invention is a method of treating a mammal (e.g., human) having a disease or condition mediated by the neuropeptide Y Y5 receptor by administering a therapeutically effective amount of a compound of formula I or formula III, or a pharmaceutically acceptable salt of said compound to the mammal.

A dosage for the invention is about 0.001 to 30 mg/kg/day of the formula I or formula III compound. An additional dosage range is about 0.001 to 3 mg/kg/day of a compound of formula I or formula III, or a pharmaceutically acceptable salt of said compound.

Another aspect of this invention is directed to a method of treating obesity comprising administering to a mammal in need of such treatment a therapeutically effective amount of a compound of formula I or formula III or a pharmaceutically acceptable salt of said compound.

Another aspect of this invention is directed to a method for treating metabolic and eating disorders such as bulimia and anorexia comprising administering to a mammal a therapeutically effective amount of a compound of formula I or formula III, or a pharmaceutically acceptable salt of said compound.

Another aspect of this invention is directed to a method for treating hyperlipidemia comprising administering to a mammal a therapeutically effective amount of a compound of formula I or formula III, or a pharmaceutically acceptable salt of said compound.

Another aspect of this invention is directed to a method for treating cellulite and fat accumulation comprising administering to a mammal a therapeutically effective amount of a compound of formula I or formula III, or a pharmaceutically acceptable salt of said compound.

Another aspect of this invention is directed to a method for treating Type II diabetes comprising administering to a mammal a therapeutically effective amount of a compound of formula I or formula III or a pharmaceutically acceptable salt of said compound.

In addition to the "direct" effect of the compounds of this invention on the neuropeptide Y Y5 receptor subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise an amount of a compound of formula I or formula III, or a pharmaceutically acceptable salt of said compound and a pharmaceutically acceptable carrier.

This invention is also directed to pharmaceutical compositions for the treatment of obesity which comprise an obesity treating amount of a compound of formula I or formula III, or a pharmaceutically acceptable salt of said compound or of said and a pharmaceutically acceptable carrier therefor.

Compounds of formula I or formula III can be produced by processes known to those skilled in the art using either solution phase or solid phase synthesis as shown in the following reaction schemes, in the preparations and examples below.

Compounds of formula I where X is N, D is absent, A is absent, E is H, $R^2$ is H, $R^4$ is H, j is 1, k is 1, m is 2, n is 2, and Z is $NR^8$ can be prepared by Scheme 1, as follows:

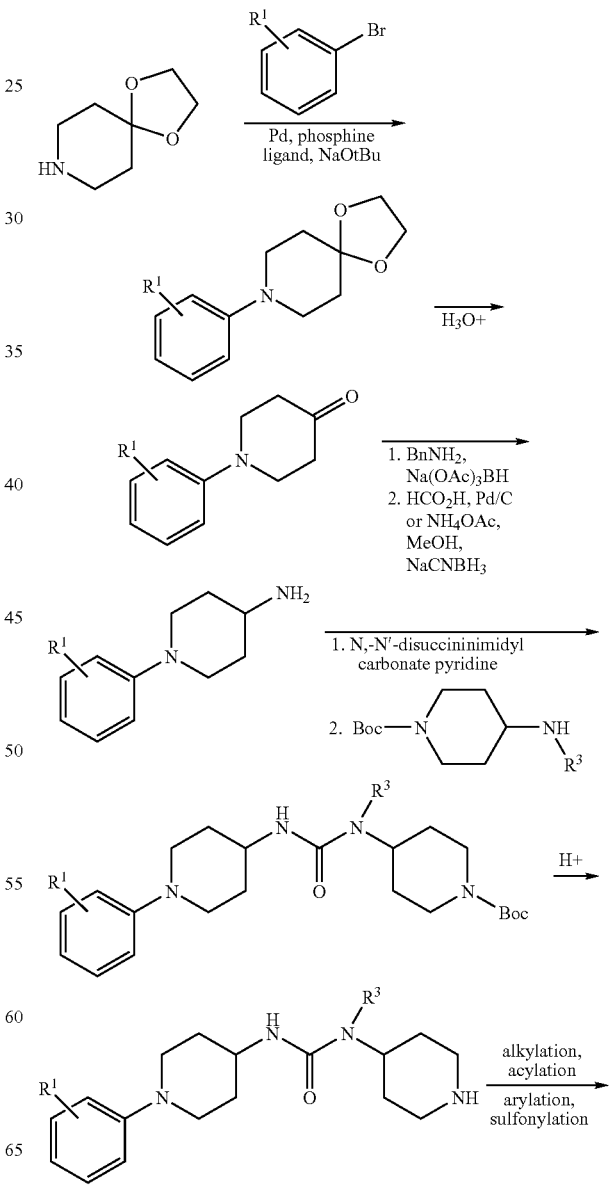

-continued
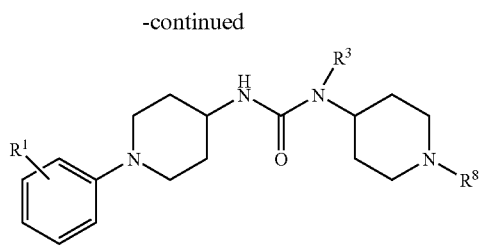
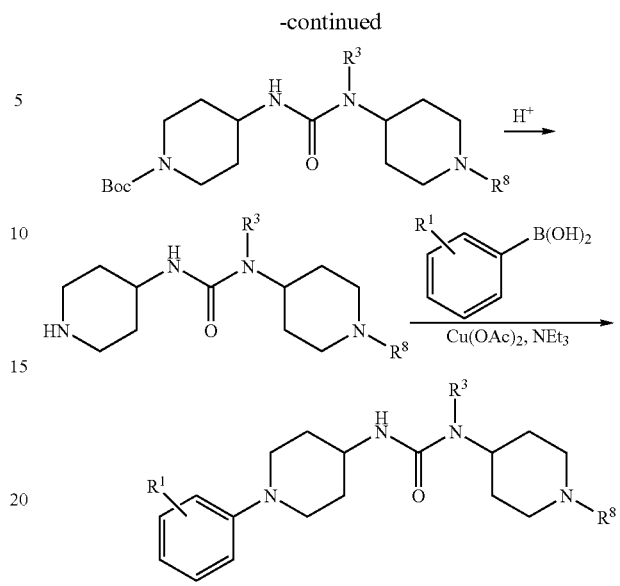
Compounds of formula I wherein X is C, D is H, A is absent, E is H, $R^2$ is H, $R^4$ is H, j is 1, k is 1, m is 2, n is 2 and Z is $NR^8$ can be prepared by Scheme 4, as follows:
Scheme 2
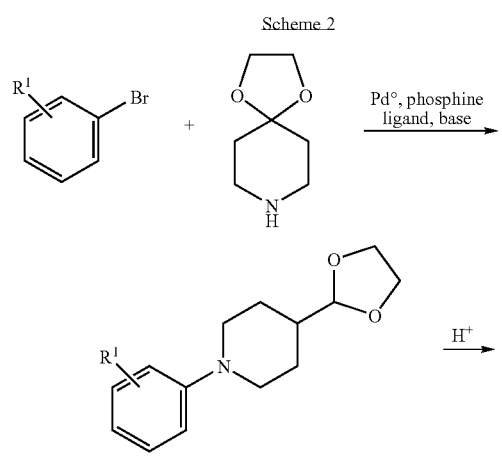
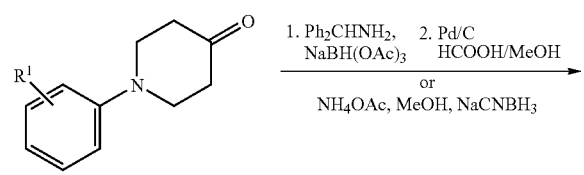
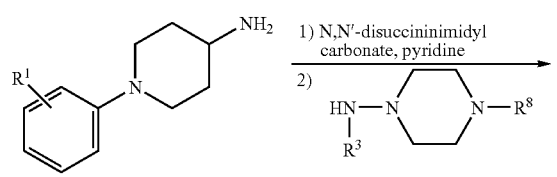
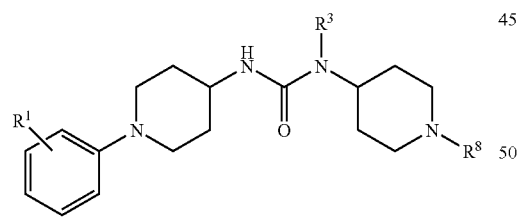
Scheme 4
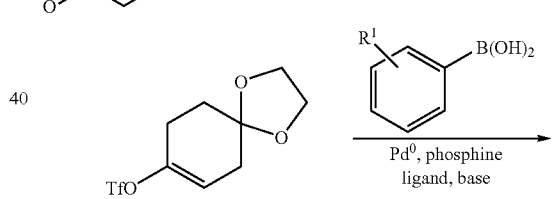
Scheme 3
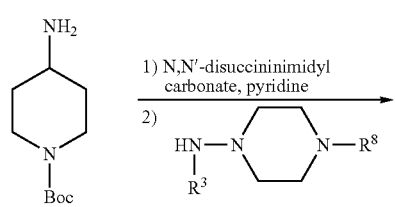
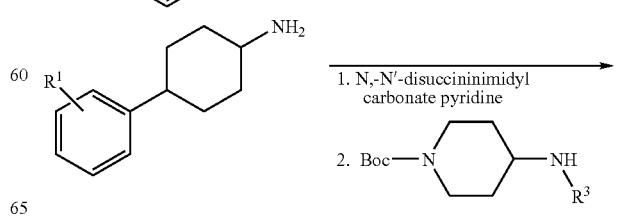

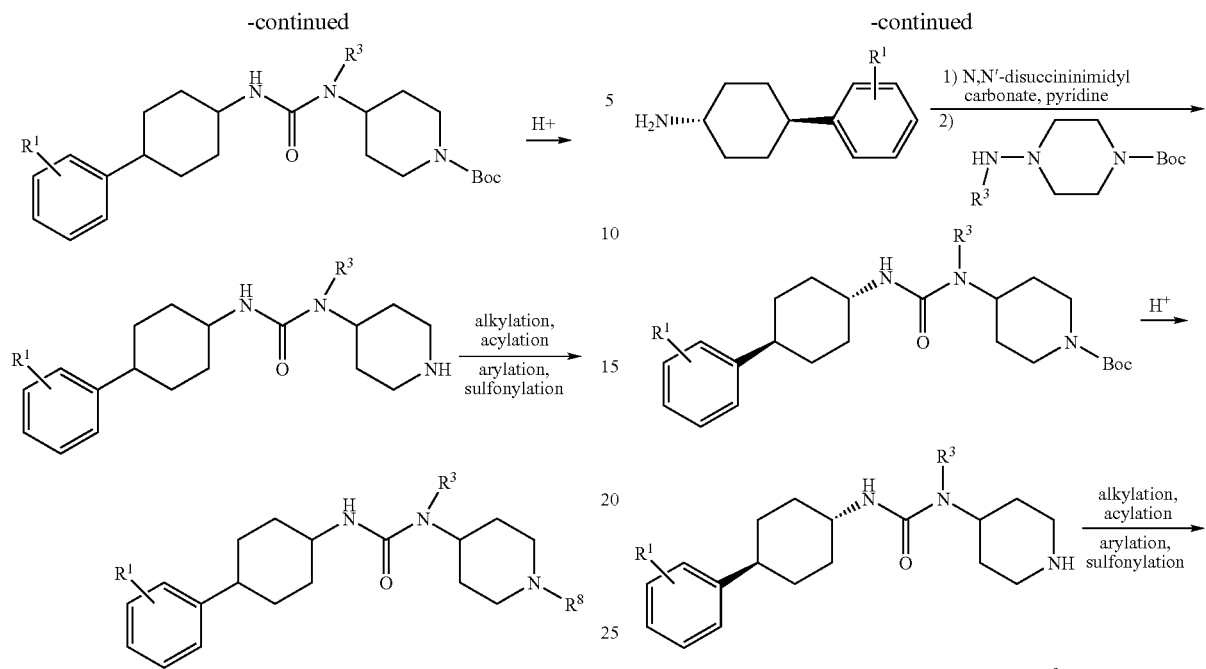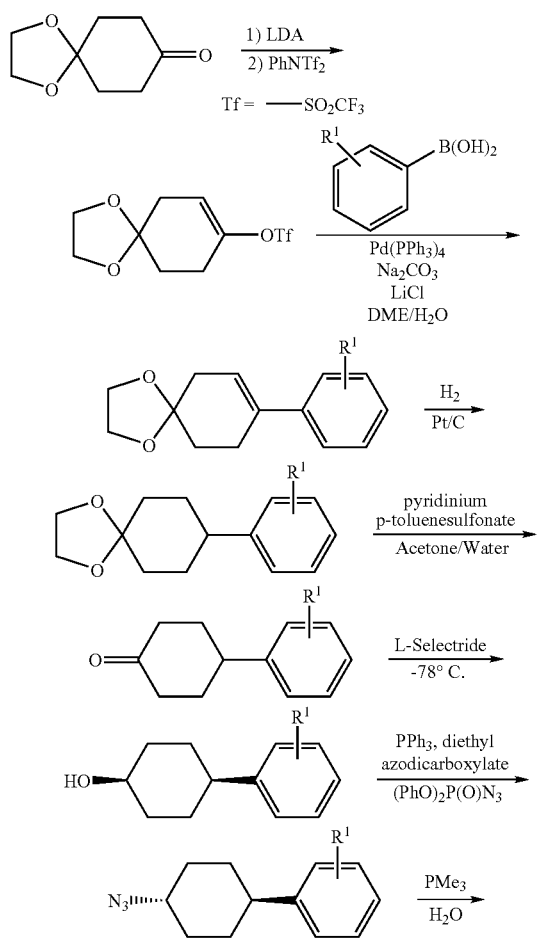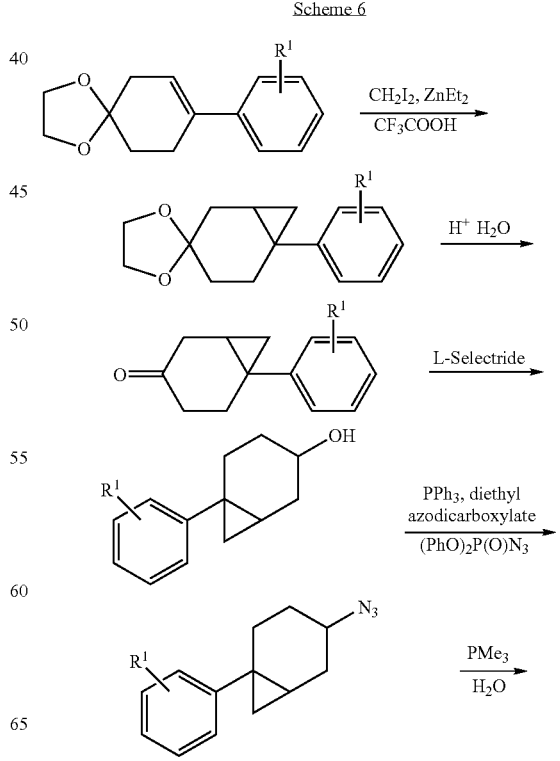

-continued
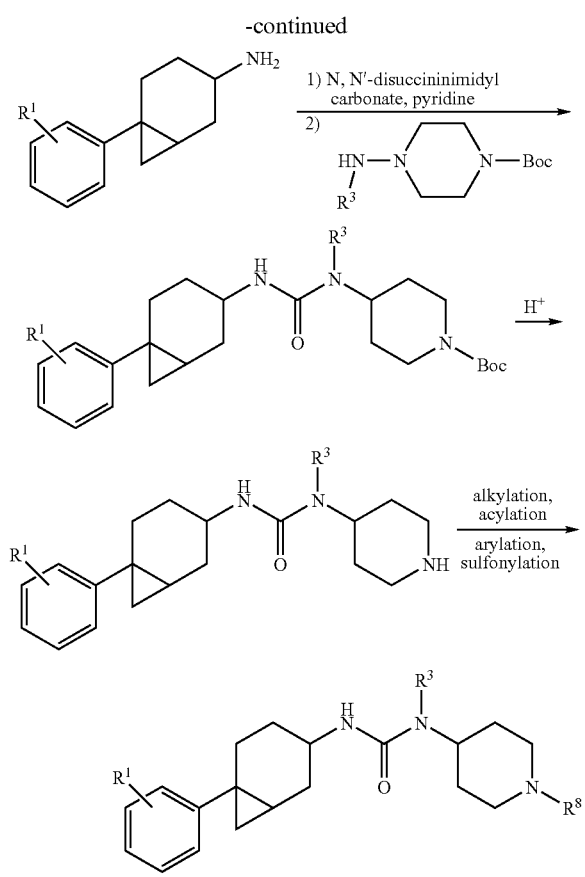
Scheme 7
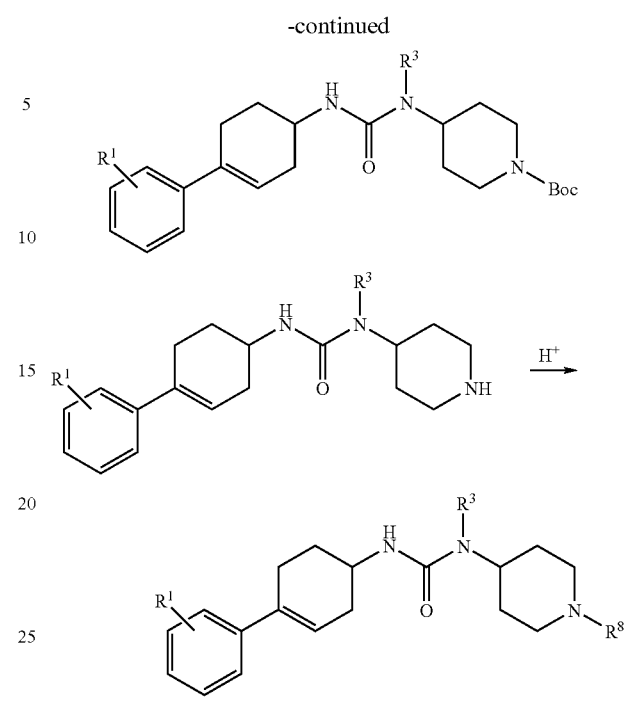
Scheme 8
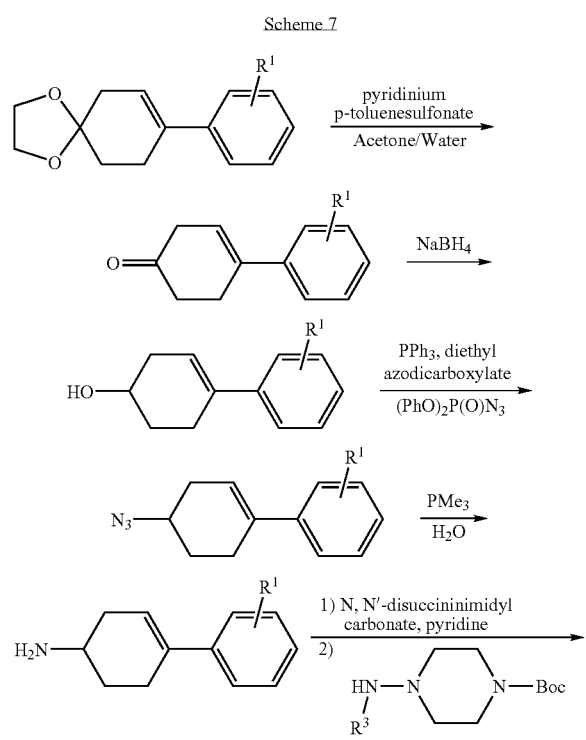

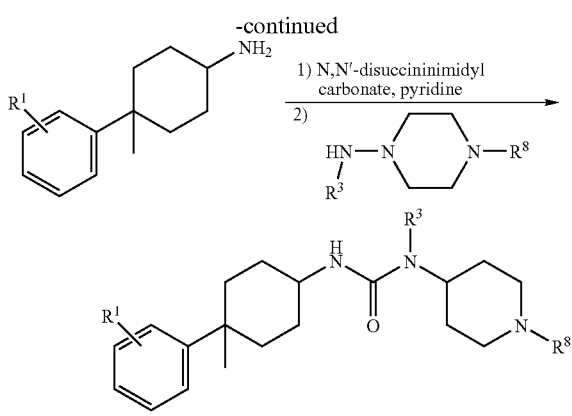

Combinatorial libraries of compounds of formula I can also be prepared using solid phase chemistry as shown in the schemes above.

Alternative mechanistic pathways and analogous structures within the scope of the invention would be apparent to those skilled in the art.

Starting materials are prepared by known methods and/or methods described in the Preparations.

The compounds of formula I or formula III exhibit Y Y5 receptor antagonizing activity, which has been correlated with pharmaceutical activity for treating metabolic disorders, such as obesity, eating disorders such as hyperphagia, and diabetes.

The compounds of formula I or formula III display pharmacological activity in a test procedure designed to demonstrate Y Y5 receptor antagonist activity. The compounds are non-toxic at pharmaceutically therapeutic doses.

cAMP Assay

HEK-293 cells expressing the Y5 receptor subtype were maintained in Dulbecco's modified Eagles' media (Gico-BRL) supplemented with 10% FCS (ICN), 1% penicillin-streptomycin and 200 μg/ml Geneticin®(GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then pre-incubated with approximately 150 μl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-587) with or without the antagonist compound of interest at 37° C. After 20 minutes the 1 mM IBMX-HH assay buffer (±antagonist compound) was removed and replaced with assay buffer containing 1.5 μM (CHO cells) or 5 μM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 μl ethanol. The tissue culture plates were agitated on a platform shaker for 15 minutes, after which the plates were transferred to a warm bath in order to evaporate the ethanol. Upon bringing all wells to dryness, the cell residues were re-solubilized with 250 μl FlashPlate®) assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control.

All data points were determined in triplicate and $EC_{50}$'s (nM) were calculated using a nonlinear (sigmoidal) regression equation (GraphPad Prism™). The $K_B$ of the antagonist compound was estimated using the following formula:

$$K_B=[B]/(1-\{[A']/[A]\})$$

where

[A] is the $EC_{50}$ of the agonist (NPY) in the absence of antagonist,

[A'] is the $EC_{50}$ of the agonist (NPY) in the presence of antagonist, and

[B] is the concentration of the antagonist.

NPY Receptor Binding Assay

Human NPY Y5 receptors were expressed in CHO cells. Binding assays were performed in 50 mM HEPES, pH 7.2, 2.5 mM $CaCl_2$, 1 mM $MgCl_2$ and 0.1% BSA containing 5-10 μg of membrane protein and 0.1 nM $^{125}$L-peptide YY in a total volume of 200 μl. Non-specific binding was determined in the presence of 1 μM NPY. The reaction mixtures were incubated for 90 minutes at room temperature then filtered through Millipore MAFC glass fiber filter plates which had been pre-soaked in 0.5% polyethyleneimine. The filters were washed with phosphate-buffered saline, and radioactivity was measured in a Packard TopCount scintillation counter.

For the compounds of this invention, a range of NPY Y5 receptor binding activity (Ki values) of from about 0.2 nM to about 2,000 nM was observed. Compounds of this invention preferably have a binding activity in the range of from about 0.2 nM to about 1,000 nM, more preferably from about 0.2 to about 100 nM, and most preferably from about 0.2 to about 10 nM.

Yet another aspect of this invention are combinations of a compound of formula I or formula III, or a pharmaceutically acceptable salt of said compound and other compounds as described below.

One such aspect of this invention is a method for treating obesity comprising administering to a mammal (e.g., a female or male human)

a. an amount of a first compound, said first compound being a formula I or formula III compound, or a pharmaceutically acceptable salt of said compound; and b. an amount of a second compound, said second compound being an anti-obesity and/or anorectic agent such as a 3 agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a formula I or formula III compound, or a pharmaceutically acceptable salt of said compound a second compound, said second compound being an anti-obesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a formula I or formula III compound, or a pharmaceutically acceptable salt of said compound and a pharmaceutically acceptable carrier, vehicle or diluent in a first unit dosage form;

b. an amount of an anti-obesity and/or anorectic agent such as a $\beta_3$ agonist, a thyromimetic agent, an anorectic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a mammal (e.g., a female or male human)

a. an amount of a first compound, said first compound being a formula I or formula III compound, or a pharmaceutically acceptable salt of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a formula I or formula III compound, or a pharmaceutically acceptable salt of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a formula I or formula III compound, or a pharmaceutically acceptable salt of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The invention disclosed herein is exemplified by the following preparations and examples which should not be construed to limit the scope of the disclosure. Alternative mechanistic pathways and analogous structures will be apparent to those skilled in the art.

Where NMR data are presented, ¹H spectra were obtained on either a Varian VXR-200 (200 MHz, ¹H), Varian Gemini-300 (300 MHz) or XL-400 (400 MHz) and are reported as ppm down field from Me₄Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH₃CN, 5 min—95% CH₃CN, 7 min—95% CH₃CN, 7.5 min—10% CH₃CN, 9 min—stop. The retention time and observed parent ion are given.

The following constituents, solvents and reagents may be referred to by their abbreviations in parenthesis:
PTLC (preparative thin-layer chromatography);
N-Phenyltrifluoromethanesulfonimide (NPhTf₂);
trifluoromethanesulfonyloxy (TfO);
sodium triacetoxyborohydride (Na(OAc)₃BH);
sodium t-butoxide (NaOtBu);
lithium diisopropylamide (LDA);
dppp [1,3-bis(diphenylphosphino)propane];
THF (tetrahydrofuran);
DME (1,2-dimethoxyethane);
EtOAc (ethyl acetate);
Et₃N (triethylamine);
MeOH (methanol);
room temperature (r.t.);
and tert-butoxycarbonyl (Boc).

EXPERIMENTAL DETAILS

Example 1A

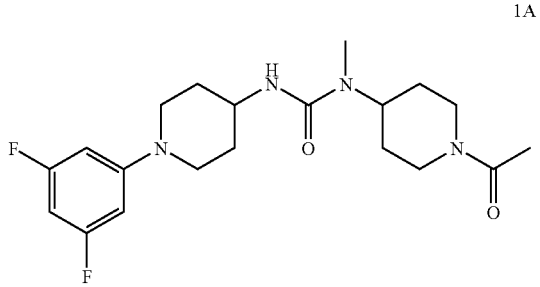

1A

Step 1. Synthesis of 14

14

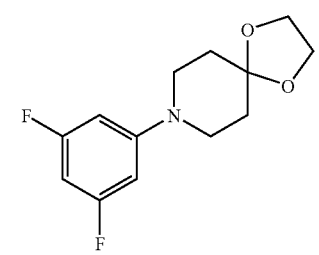

To a solution of 1-bromo-3,5-difluorobenzene (1.76 g, 9.14 mmol), 1,4-dioxa-azaspiro(4,5)decane (1.41 g, 9.8 mmol), Pd(OAc)₂ (0.096 g, 0.43 mmol), dppp (0.21 g, 0.50 mmol) in anhydrous toluene (5 ml) was added NaOtBu (2.04 g, 21.2 mmol). The reaction mixture was degassed with nitrogen, then sealed and heated at 90° C. for 16 hours. The mixture was diluted with CH₂Cl₂ (50 ml) and filtered. The filtrate was concentrated in vacuo and the residue was separated by flash column chromatography (hexane:EtOAc 100:0→95:5, v/v) to give 14 (2.0 g, 86%). MS m/e 256 (M+H)⁺.

Step 2. Synthesis of 15

15

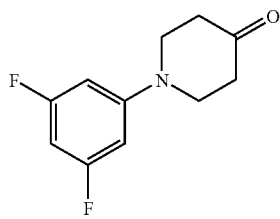

To a solution of 14 (0.1 g, 0.04 mmol) in THF (4 ml) was added 5N HCl (4 ml). The reaction mixture was stirred at room temperature for 16 hours. The mixture was adjusted to pH 10 with saturated sodium bicarbonate solution and extracted with CH₂Cl₂ (2×15 ml). The combined organic layer was washed with brine (30 ml), separated and dried over magnesium sulfate. The concentrated residue was separated by PTLC (hexane:EtOAc 4:1, v/v) to give 15 (0.065 g, 79%). MS m/e 212 (M+H)⁺.

Step 3. Synthesis of 16

16

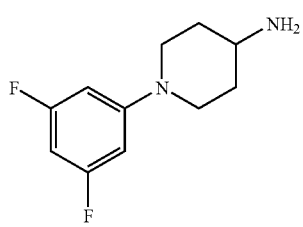

To a solution of 15 (0.80 g, 3.8 mmol), benzylamine (0.64 g, 6.0 mmol) in DME (50 ml) was added Na(OAc)₃BH (1.6 g, 7.5 mmol). After the reaction mixture was stirred at room temperature for 16 hours, 1N NaOH (50 ml) and CH₂Cl₂ (50 ml) were added. The organic layer was separated, washed with water (50 ml) and brine (50 ml), then dried over magnesium sulfate. The concentrated residue was dissolved in MeOH (100 ml). Formic acid (4.50 ml, 119 mmol) and 10% Pd/C (1 g, 0.9 mmol) were added. The reaction mixture was stirred at room temperature for 16 hours. The mixture was filtered via celite. The filtrate was concentrated and diluted with CH₂Cl₂ (50 ml) and 1N NaOH (50 ml). The organic layer was washed with brine (50 ml), dried over magnesium sulfate, and concentrated in vacuo to give 16 (0.66 g, 82%). MS m/e 213 (M+H)⁺.

Step 4. Synthesis of 17

17

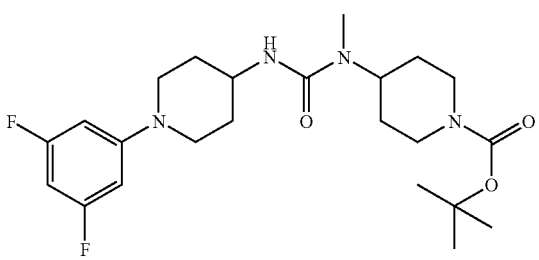

To a solution of 16 (0.21 g, 1.0 mmol) in THF (5 ml) was added pyridine (0.25 ml, 3.0 mmol). The mixture was cooled in an ice water-bath, and N, N'-disuccinimidyl carbonate (0.28 g, 1.1 mmol) was added at 0° C. The mixture was stirred at room temperature for 3.5 hours, then cooled in an ice water-bath, and a solution of 1-tert-butoxycarbonyl-4-methylaminopiperidine, prepared via the procedure of WO 02/22492, page 17) (0.24 g, 1.1 mmol) in THF (1 ml) was added at 0° C. The reaction mixture was stirred at room temperature for 16 hours. The concentrated residue was diluted with CH$_2$Cl$_2$ (50 ml), then washed with 1N NaOH (50 ml), water (50 ml), and brine (50 ml). The organic layer was separated and dried over potassium carbonate. The concentrated residue was separated by PTLC (CH$_2$Cl$_2$: MeOH 20:1, v/v) to give 17 (0.36 g, 80%). MS m/e 453 (M+H)$^+$.

Step 5. Synthesis of 18

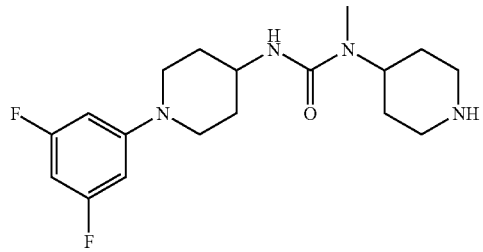

To a solution of 17 (0.33 g, 0.73 mmol) in CH$_2$Cl$_2$ (9 ml) was added trifluoroacetic acid (1 ml). The reaction mixture was stirred at room temperature for 16 hours. The concentrated residue was diluted with CH$_2$Cl$_2$ (50 ml) and washed with 1N NaOH (50 ml). The organic layer was separated and dried over magnesium sulfate. The concentrated residue was separated by flash column chromatography (1:9 MeOH/CH$_2$Cl$_2$→1:4 2M ammonia in MeOH/CH$_2$Cl$_2$) to give 18 (0.22 g, 86%). MS m/e 353 (M+H)$^+$.

Step 6

To a solution of 18 (0.050 g, 0.14 mmol) in CH$_2$Cl$_2$ (2 ml) was added acetic anhydride (0.030 ml, 0.32 mmol) and Et$_3$N (0.20 ml, 1.4 mmol). The reaction mixture was stirred at room temperature for 16 hours. PS-Trisamine resin (100 mg) was added, and the mixture was stirred for 16 hours. The mixture was filtered and washed with 4:1 MeOH/CH$_2$Cl$_2$ (50 ml). The filtrate was concentrated and the residue was separated by PTLC (CH$_2$Cl$_2$: MeOH 20:1, v/v) to give 1A (0.057 g, 94%).

Reaction of 18 with propanoyl chloride by the same procedure afforded Example 1B.

Example 1C

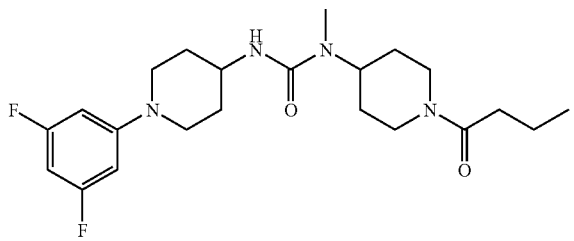

To a solution of 18 (0.050 g, 0.14 mmol) and Et$_3$N (0.20 ml, 1.4 mmol) in CH$_2$Cl$_2$ (2 ml) was added butyryl chloride (0.040 ml, 0.38 mmol) at 0° C. The reaction mixture was stirred at room temperature for 10 minutes. The concentrated residue was separated by PTLC (CH$_2$Cl$_2$:MeOH 10:1, v/v) to give 1C (0.058 g, 91%).

Using the procedure of Example 1C and the appropriate acid chloride, Examples 1D and 1E were prepared.

Example 1F

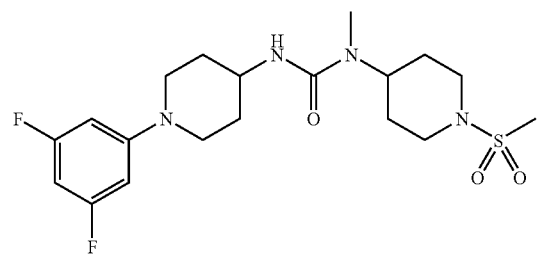

To a solution of 18 (0.050 g, 0.14 mmol) and Et$_3$N (0.20 ml, 1.4 mmol) in CH$_2$Cl$_2$ (2 ml) was added methanesulfonyl chloride (0.040 ml, 0.52 mmol) at 0° C. The reaction mixture was stirred at room temperature for 10 minutes. The concentrated residue was separated by PTLC (CH$_2$Cl$_2$:MeOH 10:1, v/v) to give 1F (0.052 g, 86%).

Using the same procedure, reaction of 18 with the appropriate sulfonyl chloride afforded 1G, 1H, 1I, 1J, and 1K.

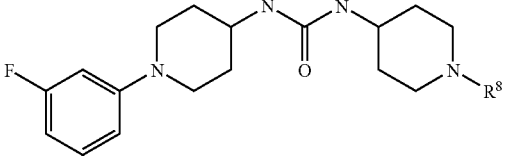

| Example | | $^1$H NMR | MS (M + H)$^+$ |
|---|---|---|---|
| 1A | 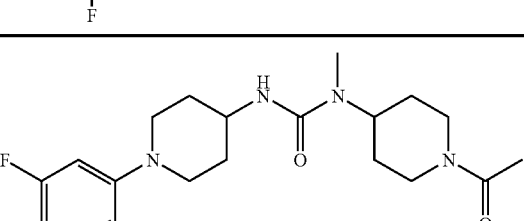 | (CDCl$_3$) δ 6.35 (m, 2H), 6.20 (m, 1H), 4.70 (m, 1H), 4.42 (m, 1H), 4.29 (m, 1H), 3.84 (m, 2H), 3.61 (m, 2H), 3.12 (m, 1H), 2.90 (m, 2H), 2.66 (s, 3H), 2.55 (m, 1H), 2.07 (s, 3H), 2.03 (m, 2H), 1.68 (m, 2H), 1.48 (m, 4H). | 395 |

-continued

| Example | | ¹H NMR | MS (M + H)⁺ |
|---|---|---|---|
| 1B | | (CDCl₃) δ 6.36 (m, 2H), 6.20 (m, 1H), 4.76 (m, 1H), 4.43 (m, 1H), 4.25 (m, 1H), 3.88 (m, 2H), 3.62 (m, 2H), 3.10 (m, 1H), 2.91 (m, 2H), 2.67 (s, 3H), 2.59 (m, 1H), 2.34 (q, J = 7.6 Hz, 2H), 2.04 (m, 2H), 1.70 (m, 2H), 1.50 (m, 4H), 1.13 (t, J = 7.6 Hz, 3H). | 409 |
| 1C | | (CDCl₃) δ 6.38 (m, 2H), 6.22 (m, 1H), 4.78 (m, 1H), 4.42 (m, 1H), 4.21 (m, 1H), 3.90 (m, 2H), 3.63 (m, 2H), 3.10 (m, 1H), 2.91 (m, 2H), 2.68 (s, 3H), 2.58 (m, 1H), 2.31 (q, J = 6.8 Hz, 2H), 2.06 (m, 2H), 1.78-1.58 (m, 4H), 1.58-1.42 (m, 4H), 0.99 (t, J = 7.6 Hz, 3H). | 423 |
| 1D | | (CDCl₃) δ 6.36 (m, 2H), 6.21 (m, 1H), 4.78 (m, 1H), 4.42 (m, 1H), 4.21 (m, 1H), 3.98 (m, 1H), 3.83 (m, 1H), 3.63 (m, 2H), 3.10 (m, 1H), 2.90 (m, 2H), 2.78 (m, 1H), 2.67 (s, 3H), 2.56 (m, 1H), 2.06 (m, 2H), 1.80-1.60 (m, 2H), 1.60-1.40 (m, 4H), 1.11 (d, J = 7.2 Hz, 6H). | 423 |
| 1E | | (CDCl₃) δ 6.34 (m, 2H), 6.20 (m, 1H), 4.70 (m, 1H), 4.42 (m, 1H), 4.27 (m, 2H), 3.82 (m, 1H), 3.60 (m, 2H), 3.18 (m, 1H), 2.90 (m, 2H), 2.67 (s, 3H), 2.60 (m, 1H), 2.04 (m, 2H), 1.73 (m, 2H), 1.64 (m, 1H), 1.47 (m, 4H), 0.95 (m, 2H), 0.73 (m, 2H). | 421 |
| 1F | | (CDCl₃) δ 6.37 (m, 2H), 6.20 (m, 1H), 4.40 (m, 1H), 4.22 (m, 1H), 3.90 (m, 3H), 3.64 (m, 2H), 2.90 (m, 2H), 2.78 (s, 3H), 2.75 (m, 2H), 2.71 (s, 3H), 2.08 (m, 2H), 1.74 (m, 4H), 1.50 (m, 2H). | 431 |

-continued

| Example | F | ¹H NMR | MS (M + H)⁺ |
|---|---|---|---|
| 1G | (ethylsulfonyl piperidine urea with 3,5-difluorophenyl piperidine) | (CDCl₃) δ 6.34 (m, 2H), 6.20 (m, 1H), 4.38 (m, 1H), 4.27 (m, 1H), 3.90 (m, 3H), 3.62 (m, 2H), 3-2.8 (m, 6H), 2.69 (s, 3H), 2.05 (m, 2H), 1.69 (m, 4H), 1.47 (m, 2H), 1.34 (t, J = 7.6 Hz, 3H). | 445 |
| 1H | (n-propylsulfonyl piperidine urea with 3,5-difluorophenyl piperidine) | (CDCl₃) δ 6.36 (m, 2H), 6.21 (m, 1H), 4.38 (m, 1H), 4.23 (m, 1H), 3.88 (m, 3H), 3.62 (m, 2H), 3.00-2.80 (m, 6H), 2.70 (s, 3H), 2.04 (m, 2H), 1.85 (m, 2H), 1.73 (m, 4H), 1.48 (m, 2H), 1.05 (t, J = 7.6 Hz, 3H). | 459 |
| 1I | (isopropylsulfonyl piperidine urea with 3,5-difluorophenyl piperidine) | (CDCl₃) δ 6.35 (m, 2H), 6.21 (m, 1H), 4.40 (m, 1H), 4.23 (m, 1H), 3.90 (m, 3H), 3.62 (m, 2H), 3.16 (m, 1H), 2.94 (m, 4H), 2.70 (s, 3H), 2.04 (m, 2H), 1.67 (m, 4H), 1.48 (m, 2H), 1.32 (d, J = 6.4 Hz, 6H). | 459 |
| 1J | (cyclopropylsulfonyl piperidine urea with 3,5-difluorophenyl piperidine) | (CDCl₃) δ 6.36 (m, 2H), 6.23 (m, 1H), 4.40 (m, 1H), 4.22 (m, 1H), 3.88 (m, 3H), 3.64 (m, 2H), 3.00-2.80 (m, 4H), 2.71 (s, 3H), 2.25 (m, 1H), 2.05 (m, 2H), 1.73 (m, 4H), 1.49 (m, 2H), 1.17 (m, 2H), 0.98 (m, 2H). | 457 |
| 1K | (phenylsulfonyl piperidine urea with 3,5-difluorophenyl piperidine) | (CDCl₃) δ 7.75 (m, 2H), 7.59 (m, 1H), 7.57 (m, 2H), 6.34 (m, 2H), 6.20 (m, 1H), 4.22 (m, 1H), 4.18 (m, 1H), 3.88 (m, 2H), 3.80 (m, 1H), 3.60 (m, 2H), 2.87 (m, 2H), 2.66 (s, 3H), 2.33 (m, 2H), 1.99 (m, 2H), 1.80-1.60 (m, 4H), 1.45 (m, 2H). | 493 |

Example 2A

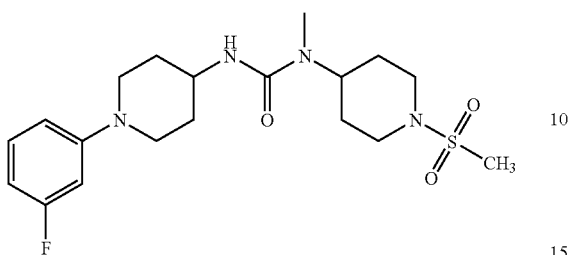

Step 1. Synthesis of 1-Methylsulfonyl-4-piperidone

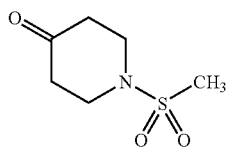

To a stirred solution of 4-piperidone hydrate hydrochloride (40.00 g, 0.260 mol) and THF (320 ml) was added $CH_3SO_2Cl$ (31.0 ml, 0.402 mol) and 15% aq. NaOH (156 ml) such that the temperature of the reaction mixture was maintained at 26-32° C. After this addition, the reaction mixture was stirred at RT for 2 hours and transferred to a separatory funnel. The organic layer was collected and the aqueous layer was extracted with THF (2×250 ml). The combined organic layers were dried over $Na_2SO_4$. After filtration, the concentrated residue was washed with hexane to give the product (46.0 g, 100%). $^1H$ NMR (CDCl$_3$) δ 3.59 (t, J=6.00 Hz, 4H), 2.89 (s, 15 3H), 2.59 (t, J=5.6 Hz, 4H).

Step 2. Synthesis of N-Methyl-1-(methylsulfonyl)-4-piperidineamine

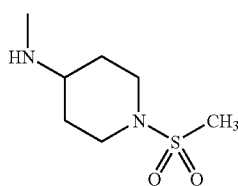

1-Methylsuylfonyl-4-piperidone (40.00 g, 0.226 mol), $CH_3CN$ (240 ml) and 40% $CH_3NH_2$ (20.4 ml, 0.263 mol) were added to a round bottom flask, and the mixture was stirred at room temperature for 1 hour. To another round bottom flask, $NaBH(OAc)_3$ (60.00 g, 0.283 mol) and 120 ml of $CH_3CN$ were added. This solution was stirred at −10° C., to which the first mixture (derived from 1-methylsulfonyl-4-piperidone) was added slowly via an additional funnel. After the addition, the reaction was allowed to warm to room temperature and stirred overnight. The reaction mixture was concentarted to a small volume, to which 1N aq. NaOH (282 ml) was added. This resulting solution was extracted with $CH_2Cl_2$ (3×500 ml) followed by extraction with toluene until no product remained in the extraction solution. The combined organic layers were dried over $Na_2SO_4$. After filtration, the solution was concentrated in vacuo to give the product (29.0 g, 63%). $^1H$ NMR (CDCl$_3$) δ 3.66 (m, 2H), 2.84 (m, 2H), 2.76 (s, 3H), 2.52 (m, 1H), 2.42 (s, 3H), 1.96 (m, 2H), 1.45 (m, 2H). MS m/e 193 (M+H)$^+$.

Step 3. Synthesis of 19

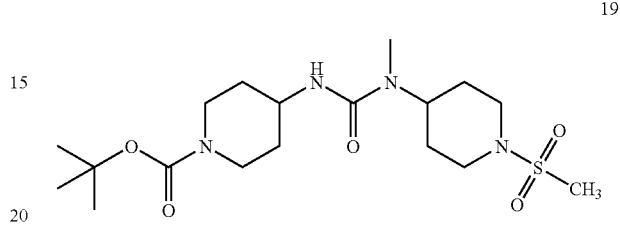

To a solution of 4-amino-N-Boc-piperidine (3.60 g, 18.0 mmol) and pyridine (5.0 ml, 61 mmol) in THF (70 ml) in an ice-water bath was added N, N'-disuccinimidyl carbonate (5.06 g, 19.8 mmol). The mixture was stirred at RT for 2 hours and cooled in an ice-water bath. N-Methyl-1-(methylsulfonyl)-4-piperidineamine (3.62 g, 18.9 mmol) was added and the mixture was stirred at RT for 16 hours. The mixture was diluted with $CH_2Cl_2$ (300 ml) and washed with 1N NaOH (200 ml), 1N HCl (100 ml), water, and brine sequentially. The organic portion was dried (MgSO$_4$), concentrated, and purified by chromatography ($CH_3OH:CH_2Cl_2$ 2:100) to give 19 (4.80 g, 64%). MS m/e 419 (M+H)$^+$.

Step 4. Synthesis of 20

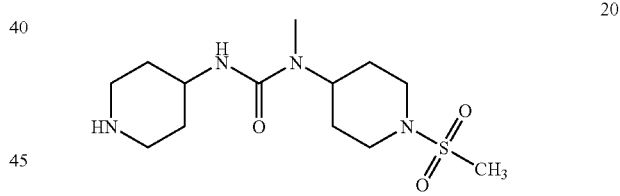

A mixture of 19 (4.80 g, 11.5 mmol) and 4N HCl/dioxane (100 ml) in THF (100 ml) was stirred at RT for 40 hours. The mixture was concentrated and the residue was purified by chromatography ($CH_3OH:CH_2Cl_2$ 1:10 gradient to 2M NH$_3$/ $CH_3OH:CH_2Cl_2$ 1:1) to give 20 (1.90 g, 52%). MS m/e 319 (M+H)$^+$.

Step 5

A mixture of 20 (0.096 g, 0.30 mmol), 3-fluorophenylboronic acid (0.063 g, 0.45 mmol), copper(II) acetate (0.055 g, 0.30 mmol), and pyridine (0.048 g, 0.61 mmol) in $CH_2Cl_2$ (2.5 ml) was stirred at RT for 17 hours. The mixture was diluted with $CH_2Cl_2$ (20 ml) and washed with water and aqueous sodium bicarbonate. The organic portion was dried ($K_2CO_3$), concentrated, and purified by PTLC ($CH_3OH$: $CH_2Cl_2$ 1:10) to give 2A (0.024 g, 19%).

Using essentially the same procedure, examples 2B through 2R were prepared.

| Example | | ¹H NMR | MS (M + H)⁺ |
|---|---|---|---|
| 2A |  | (CDCl₃) δ 7.16 (m, 1H), 6.69 (m, 1H), 6.60 (m, 1H), 6.51 (m, 1H), 4.38 (m, 1H), 4.25 (m, 1H), 3.88 (m, 3H), 3.64 (m, 2H), 2.90 (m, 2H), 2.79 (s, 3H), 2.75 (m, 2H), 2.71 (s, 3H), 2.06 (m, 2H), 1.74 (m, 4H), 1.53 (m, 2H). | 413 |
| 2B | 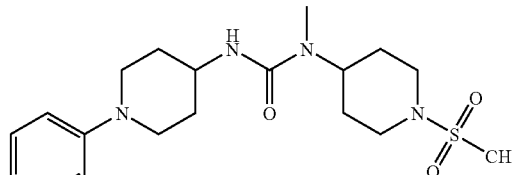 | (CDCl₃) δ 7.14 (m, 1H), 6.87 (m, 1H), 6.78 (m, 2H), 4.36 (m, 1H), 4.27 (m, 1H), 3.86 (m, 3H), 3.63 (m, 2H), 2.88 (m, 2H), 2.78 (s, 3H), 2.75 (m, 2H), 2.70 (s, 3H), 2.05 (m, 2H), 1.73 (m, 4H), 1.51 (m, 2H). | 429 |
| 2C | 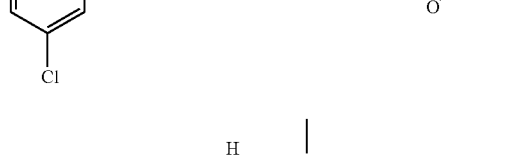 | (CDCl₃) δ 7.33 (m, 1H), 7.05 (m, 3H), 4.37 (m, 1H), 4.27 (m, 1H), 3.87 (m, 3H), 3.69 (m, 2H), 2.91 (m, 2H), 2.78 (s, 3H), 2.75 (m, 2H), 2.71 (s, 3H), 2.09 (m, 2H), 1.74 (m, 4H), 1.53 (m, 2H). | 463 |
| 2D | 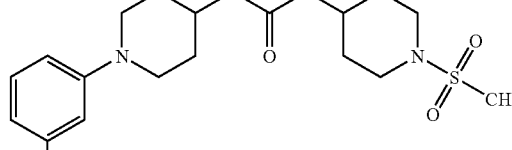 | (CDCl₃) δ 7.30 (m, 1H), 7.10 (m, 3H), 4.38 (m, 1H), 4.26 (m, 1H), 3.88 (m, 3H), 3.67 (m, 2H), 2.93 (m, 2H), 2.79 (s, 3H), 2.76 (m, 2H), 2.72 (s, 3H), 2.07 (m, 2H), 1.74 (m, 4H), 1.52 (m, 2H). | 420 |
| 2E | 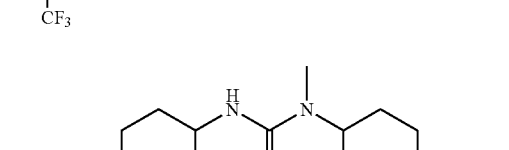 | (CDCl₃) δ 7.25 (m, 2H), 6.94 (m, 2H), 6.84 (m, 1H), 4.37 (m, 1H), 4.26 (m, 1H), 3.86 (m, 3H), 3.63 (m, 2H), 2.88 (m, 2H), 2.78 (s, 3H), 2.75 (m, 2H), 2.71 (s, 3H), 2.05 (m, 2H), 1.75 (m, 4H), 1.56 (m, 2H). | 395 |
| 2F | 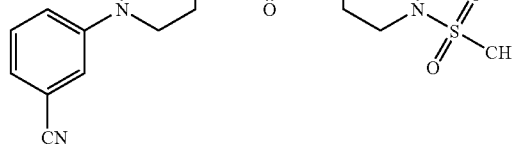 | (CDCl₃) δ 7.15 (t, J = 8.2 Hz, 1H), 6.54 (m, 1H), 6.48 (m, 1H), 6.39 (m, 1H), 4.37 (m, 1H), 4.26 (m, 1H), 3.87 (m, 3H), 3.78 (s, 3H), 3.64 (m, 2H), 2.91 (m, 2H), 2.78 (s, 3H), 2.75 (m, 2H), 2.71 (s, 3H), 2.04 (m, 2H), 1.74 (m, 4H), 1.54 (m, 2H). | 425 |

| Example | | ¹H NMR | MS (M + H)⁺ |
|---|---|---|---|
| 2G | [structure: 1-(3,5-dichlorophenyl)piperidin-4-yl urea with N-methyl-4-(methylsulfonyl)piperidine] | (CDCl₃) δ 6.76 (m, 3H), 4.37 (m, 1H), 4.24 (m, 1H), 3.88 (m, 3H), 3.63 (m, 2H), 2.91 (m, 2H), 2.82 (s, 3H), 2.75 (m, 2H), 2.71 (s, 3H), 2.05 (m, 2H), 1.74 (m, 4H), 1.48 (m, 2H). | 463 |
| 2H | [structure: 1-(4-fluorophenyl)piperidin-4-yl urea analog] | (CDCl₃) δ 6.93 (m, 4H), 4.37 (m, 1H), 4.27 (m, 1H), 3.87 (m, 2H), 3.81 (m, 1H), 3.50 (m, 2H), 2.84 (m, 2H), 2.78 (s, 3H), 2.75 (m, 2H), 2.72 (s, 3H), 2.05 (m, 2H), 1.74 (m, 4H), 1.59 (m, 2H). | 413 |
| 2I | [structure: 1-(3-bromophenyl)piperidin-4-yl urea analog] | (CDCl₃) δ 7.09 (m, 2H), 6.97 (m, 1H), 6.88 (m, 1H), 4.37 (m, 1H), 4.30 (m, 1H), 3.87 (m, 3H), 3.63 (m, 2H), 2.91 (m, 2H), 2.78 (s, 3H), 2.75 (m, 2H), 2.71 (s, 3H), 2.06 (m, 2H), 1.75 (m, 4H), 1.58 (m, 2H). | 473 |
| 2J | [structure: 1-(3-chloro-4-fluorophenyl)piperidin-4-yl urea analog] | (CDCl₃) δ 7.03 (m, 1H), 6.95 (m, 1H), 6.81 (m, 1H), 4.37 (m, 1H), 4.27 (m, 1H), 3.87 (m, 2H), 3.81 (m, 1H), 3.52 (m, 2H), 2.85 (m, 2H), 2.78 (s, 3H), 2.75 (m, 2H), 2.72 (s, 3H), 2.07 (m, 2H), 1.74 (m, 4H), 1.57 (m, 2H). | 447 |
| 2K | [structure: 1-(4-chlorophenyl)piperidin-4-yl urea analog] | (CDCl₃) δ 7.18 (m, 2H), 6.87 (m, 2H), 4.36 (m, 1H), 4.28 (m, 1H), 3.87 (m, 3H), 3.58 (m, 2H), 2.86 (m, 2H), 2.77 (s, 3H), 2.74 (m, 2H), 2.70 (s, 3H), 2.05 (m, 2H), 1.73 (m, 4H), 1.56 (m, 2H). | 429 |
| 2L | [structure: 1-(4-bromophenyl)piperidin-4-yl urea analog] | (CDCl₃) δ 7.32 (m, 2H), 6.82 (m, 2H), 4.37 (m, 1H), 4.27 (m, 1H), 3.85 (m, 3H), 3.59 (m, 2H), 2.87 (m, 2H), 2.78 (s, 3H), 2.74 (m, 2H), 2.71 (s, 3H), 2.06 (m, 2H), 1.73 (m, 4H), 1.56 (m, 2H). | 473 |

-continued

| Example | | ¹H NMR | MS (M + H)⁺ |
|---|---|---|---|
| 2M | [structure: 1-(3,4-difluorophenyl)piperidin-4-yl urea linked to 1-(methylsulfonyl)piperidin-4-yl, N-methyl] | (CDCl₃) δ 7.02 (m, 1H), 6.74 (m, 1H), 6.62 (m, 1H), 4.37 (m, 1H), 4.27 (m, 1H), 3.87 (m, 2H), 3.81 (m, 1H), 3.52 (m, 2H), 2.86 (m, 2H), 2.78 (s, 3H), 2.75 (m, 2H), 2.72 (s, 3H), 2.08 (m, 2H), 1.74 (m, 4H), 1.56 (m, 2H). | 431 |
| 2N | [structure: 1-(3-methylphenyl)piperidin-4-yl urea linked to 1-(methylsulfonyl)piperidin-4-yl, N-methyl] | (CDCl₃) δ 7.15 (m, 1H), 6.74 (m, 3H), 4.33 (m, 2H), 3.87 (m, 3H), 3.62 (m, 2H), 2.89 (m, 2H), 2.78 (s, 3H), 2.75 (m, 2H), 2.72 (s, 3H), 2.31 (s, 3H), 2.08 (m, 2H), 1.75 (m, 4H), 1.61 (m, 2H). | 409 |
| 2O | [structure: 1-(3,4-dichlorophenyl)piperidin-4-yl urea linked to 1-(methylsulfonyl)piperidin-4-yl, N-methyl] | (CDCl₃) δ 7.26 (m, 1H), 7.00 (m, 1H), 6.79 (m, 1H), 4.37 (m, 1H), 4.27 (m, 1H), 3.87 (m, 3H), 3.60 (m, 2H), 2.90 (m, 2H), 2.78 (s, 3H), 2.75 (m, 2H), 2.71 (s, 3H), 2.08 (m, 2H), 1.74 (m, 4H), 1.56 (m, 2H). | 463 |
| 2P | [structure: 1-(naphthalen-2-yl)piperidin-4-yl urea linked to 1-(methylsulfonyl)piperidin-4-yl, N-methyl] | (CDCl₃) δ 7.72 (m, 3H), 7.40 (m, 1H), 7.28 (m, 2H), 7.18 (m, 1H), 4.34 (m, 2H), 3.88 (m, 3H), 3.77 (m, 2H), 2.99 (m, 2H), 2.78 (s, 3H), 2.75 (m, 2H), 2.72 (s, 3H), 2.13 (m, 2H), 1.74 (m, 4H), 1.65 (m, 2H). | 445 |
| 2Q | [structure: 1-(2-methylphenyl)piperidin-4-yl urea linked to 1-(methylsulfonyl)piperidin-4-yl, N-methyl] | (CDCl₃) δ 7.18 (m, 2H), 7.00 (m, 2H), 4.35 (m, 2H), 3.85 (m, 3H), 3.12 (m, 2H), 2.80 (s, 3H), 2.77 (m, 2H), 2.74 (s, 3H), 2.31 (s, 3H), 2.06 (m, 2H), 1.75 (m, 4H), 1.65 (m, 2H). | 409 |
| 2R | [structure: 1-(3-acetylphenyl)piperidin-4-yl urea linked to 1-(methylsulfonyl)piperidin-4-yl, N-methyl] | (CDCl₃) δ 7.59 (m, 1H), 7.44 (m, 1H), 7.35 (m, 1H), 7.24 (m, 1H), 4.34 (m, 2H), 3.89 (m, 3H), 3.71 (m, 2H), 2.97 (m, 2H), 2.80 (s, 3H), 2.76 (m, 2H), 2.72 (s, 3H), 2.61 (s, 3H), 2.10 (m, 2H), 1.74 (m, 4H), 1.62 (m, 2H). | 437 |

Example 3

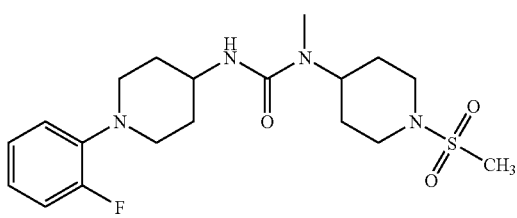

Step 1. Synthesis of 21

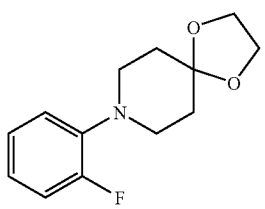

A mixture of 2-bromofluorobenzene (3.04 g, 17.4 mmol), 1,4-dioxa-8-azaspiro(4.5)decane (2.13 g, 14.9 mmol), palladium dibenzylideneacetone (0.657 g, 0.717 mmol), 2,2'-bis(diphenylphosphino)-1,1'-binaphthyl (0.678 g, 1.09 mmol), and sodium t-butoxide (3.54 g, 36.8 mmol) in toluene (20 ml) was heated to 95° C. for 16 hours. The mixture was diluted with $CH_2Cl_2$ (50 ml) and filtered. The filtrate was evaporated and purified by column chromatography ($CH_2Cl_2$ gradient to $CH_3OH:CH_2Cl_2$ 1:500) to give 21 (3.27 g, 93%). MS m/e 238 $(M+H)^+$.

Step 2. Synthesis of 22

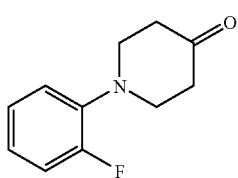

A mixture of 21 (3.27 g, 13.8 mmol) in THF (50 ml) and aqueous 5N HCl (50 ml) was stirred at RT for 16 hours and then at 85° C. for 4 hours. The volatiles were removed under reduced pressure and the residue was partitioned between $CH_2Cl_2$ (2×100 ml) and aqueous ammonium hydroxide (80 ml). The combined organic portion was dried ($MgSO_4$), evaporated, and purified by column chromatography (Hexanes gradient to EtOAc:Hexanes 2:100) to give 22 (1.54 g, 58%). MS m/e 194 $(M+H)^+$.

Step 3. Synthesis of 23

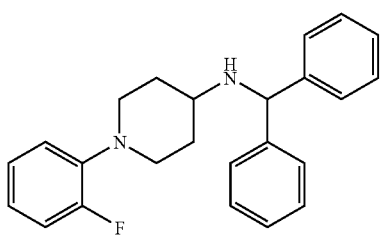

A mixture of 22 (1.54 g, 8.00 mmol), aminodiphenylmethane (1.43 g, 7.48 mmol), and sodium triacetoxyborohydride (2.57 g, 12.1 mmol) in dichloroethane (20 ml) was stirred at RT for 16 hours. The mixture was diluted with $CH_2Cl_2$ (80 ml) and washed with 1N NaOH (40 ml). The organic portion was dried ($MgSO_4$), evaporated, and purified by column chromatography (Hexanes gradient to EtOAc:Hexanes 4:100) to give 23 (2.41 g, 90%). MS m/e 361 $(M+H)^+$.

Step 4. Synthesis of 24

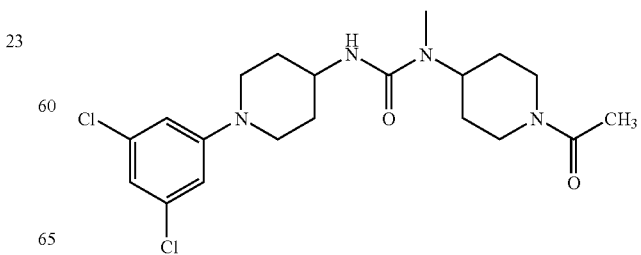

A mixture of 23 (2.41 g, 6.70 mmol), formic acid (4.4 ml), and 10% Pd/C (1.12 g) in $CH_3OH$ (100 ml) was stirred for 3 hours. The mixture was filtered through a celite pad and the filtrate was evaporated to dryness. The residue was partitioned between $CH_2Cl_2$ (100 ml) and aqueous ammonium hydroxide (50 ml). The organic portion was dried ($MgSO_4$), evaporated, and purified by column chromatography ($CH_2Cl_2$ gradient to $CH_3OH:CH_2Cl_2$ 1:4) to give 24 (1.15 g, 88%). MS m/e 195 $(M+H)^+$.

Step 5

A mixture of 24 (0.087 g, 0.45 mmol), N, N'-disuccinimidyl carbonate (0.138 g, 0.538 mmol), and pyridine (0.199 g, 2.52 mmol) in THF (7 ml) was stirred in an ice-water bath for 30 minutes and then at RT for 3 hours. N-Methyl-1-(methylsulfonyl)-4-piperidineamine (0.098 g, 0.51 mmol) was added and the mixture was stirred at RT for 20 hours. The volatiles were removed under reduced pressure and the residue was partitioned between aqueous ammonium chloride (15 ml) and $CH_2Cl_2$ (40 ml). The organic portion was dried ($MgSO_4$), evaporated, and purified by PTLC ($CH_3OH:CH_2Cl_2$ 3:100) to give 3 (0.051 g, 27%). $^1$H-NMR ($CDCl_3$) δ 7.02 (m, 4H), 4.33 (m, 2H), 3.87 (m, 3H), 3.42 (m, 2H), 2.86 (m, 2H), 2.78 (s, 3H), 2.75 (m, 2H), 2.73 (s, 3H), 2.08 (m, 2H), 1.74 (m, 6H). MS m/e 413 $(M+H)^+$.

Example 4A

Step 1. Synthesis of 25

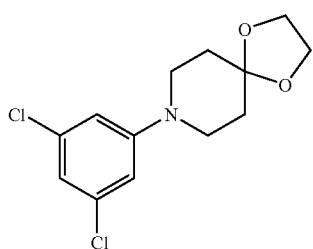

A mixture of 1-bromo-3,5-dichlorobenzene (7.43 g, 32.9 mmol), 1,4-dioxa-8-azaspiro(4.5)decane (3.90 g, 27.2 mmol), palladium dibenzylideneacetone (0.591 g, 0.645 mmol), 2,2'-bis(diphenylphosphino)-1,1'-binaphthyl (0.598 g, 0.960 mmol), and sodium t-butoxide (4.33 g, 45.0 mmol) in toluene (30 ml) was heated to 100° C. for 16 hours. The mixture was diluted with $CH_2Cl_2$ (20 ml) and filtered. The filtrate was concentrated and purified by column chromatography (Hexanes gradient to EtOAc:Hexanes 1:40) to give 25 (6.67 g, 85%). MS m/e 288 $(M+H)^+$.

Step 2. Synthesis of 26

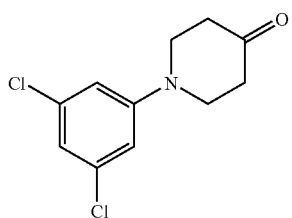

A mixture of 25 (6.67 g, 23.2 mmol) in THF (20 ml) and aqueous 5N HCl (100 ml) was stirred at RT for 64 hours. The mixture was basified with conc. $NH_4OH$ and extracted with $CH_2Cl_2$ (3×200 ml). The combined organic portion was washed with brine, dried ($MgSO_4$), and concentrated to give 26 (5.50 g, 97%). MS m/e 244 $(M+H)^+$.

Step 3. Synthesis of 27

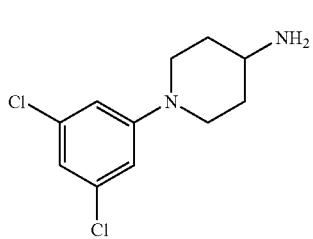

A mixture of 26 (2.44 g, 10.0 mmol), ammonium acetate (76 g, 0.99 mol), and sodium cyanoborohydride (0.500 g, 7.96 mmol) in $CH_3OH$ (200 ml) was stirred at RT for 66 hours. The mixture was concentrated and the residue was partitioned between conc. $NH_4OH$ (150 ml) and $CH_2Cl_2$ (2×150 ml). The combined organic portion was washed with water (150 ml) and brine (150 ml), dried ($K_2CO_3$), concentrated, and purified by column chromatography ($CH_2Cl_2$ gradient to 2M $NH_3/CH_3OH:CH_2Cl_2$ 1:10) to give 27 (1.66 g, 68%). MS m/e 245 $(M+H)^+$.

Step 4. Synthesis of 28

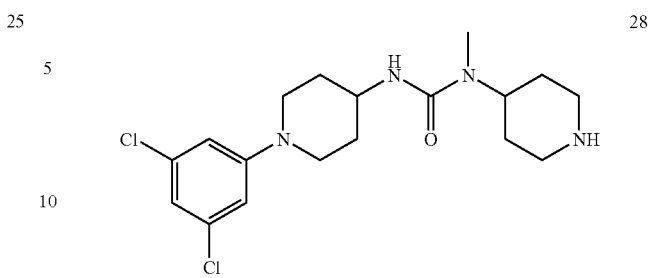

To a solution of 27 (1.23 g, 5.02 mmol) and pyridine (3 ml) in THF (100 ml) in an ice-water bath was added N,N'-disuccinimidyl carbonate (1.54 g, 6.03 mmol). The mixture was stirred at RT for 4 hours and a solution of 4-methylamino-1-Boc-piperidine (1.18 g, 5.51 mmol) was added at 0° C. The reaction was stirred at RT for 16 hours and concentrated. The residue was dissolved in $CH_2Cl_2$ (200 ml), washed with 1N NaOH (150 ml) and brine, dried ($K_2CO_3$) and concentrated. The crude material and trifluoroacetic acid (8 ml) in $CH_2Cl_2$ (72 ml) was stirred at RT for 21 hours. The mixture was concentrated and partitioned between $CH_2Cl_2$ (200 ml) and conc. $NH_4OH$ (50 ml). The organic portion was washed in sodium bicarbonate and brine, dried ($K_2CO_3$), concentrated, and purified by column chromatography ($CH_2Cl_2$ gradient to 2M $NH_3/CH_3OH:CH_2Cl_2$ 1:10) to give 28 (1.20 g, 62%). MS m/e 385 $(M+H)^+$.

Step 5

A mixture of 28 (0.077 g, 0.20 mmol), acetic anhydride (50 µl, 0.53 mmol), and triethylamine (200 µl, 1.42 mmol) in $CH_2Cl_2$ (5 ml) was stirred at RT for 3 hours. 1N NaOH (2 ml) was added and the organic portion was dried ($MgSO_4$), concentrated, and purified by PTLC ($CH_3OH:CH_2Cl_2$ 1:10) to give 4A (0.080 g, 94%).

Using essentially the same procedure, 4B was prepared.

Example 4C

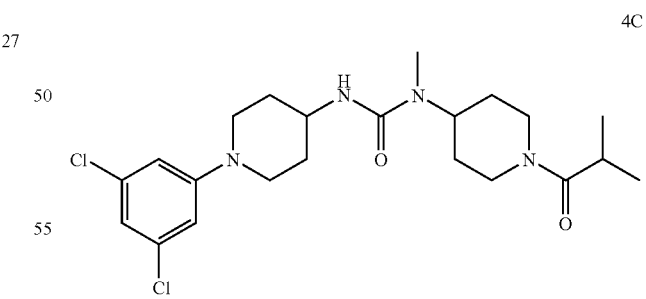

A mixture of 28 (0.077 g, 0.20 mmol), isobutyryl chloride (45 µl, 0.43 mmol), and triethylamine (200 µl, 1.42 mmol) in $CH_2Cl_2$ (5 ml) was stirred at RT for 2 hours. The mixture was washed with 1N NaOH (2 ml), dried ($MgSO_4$), concentrated, and purified by PTLC ($CH_3OH:CH_2Cl_2$ 1:10) to give 4C (0.085 g, 93%).

Using essentially the same procedure, 4D, 4E, 4F, 4G, and 4H were prepared.

Example 4I

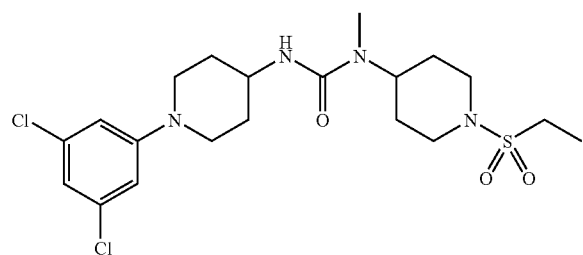

A mixture of 28 (0.077 g, 0.20 mmol), ethanesulfonyl chloride (45 μl, 0.47 mmol), and triethylamine (200 μl, 1.42 mmol) in $CH_2Cl_2$ (5 ml) was stirred at RT for 2 hours. The mixture was washed with 1N NaOH, dried ($MgSO_4$), concentrated, and purified by PTLC ($CH_3OH:CH_2Cl_2$ 1:10) to give 4I (0.082 g, 86%).

Using essentially the same procedure, 4J, 4K, and 4L were prepared.

| Example | | $^1$H NMR | MS (M + H)$^+$ |
|---|---|---|---|
| 4A | | (CDCl$_3$) δ 6.77 (m, 3H), 4.74 (m, 1H), 4.44 (m, 1H), 4.21 (m, 3.86 (m, 2H), 3.63 (m, 2H), 3.15 (m, 1H), 2.93 (m, 2H), 2.68 (s, 3H), 2.58 (m, 1H), 2.11 (s, 3H), 2.08 (m, 2H), 1.68 (m, 2H), 1.53 (m, 4H). | 427 |
| 4B | | (CDCl$_3$) δ 6.75 (m, 3H), 4.75 (m, 1H), 4.43 (m, 1H), 4.22 (m, 1H), 3.89 (m, 2H), 3.63 (m, 2H), 3.09 (m, 1H), 2.92 (m, 2H), 2.68 (s, 3H), 2.58 (m, 1H), 2.35 (q, J = 7.4 Hz, 2H), 2.05 (m, 2H), 1.69 (m, 2H), 1.49 (m, 4H), 1.15 (t, J = 7.4 Hz, 3H). | 441 |
| 4C | | (CDCl$_3$) δ 6.75 (m, 3H), 4.75 (m, 1H), 4.44 (m, 1H), 4.22 (m, 1H), 4.00 (m, 1H), 3.86 (m, 1H), 3.63 (m, 2H), 3.11 (m, 1H), 2.92 (m, 2H), 2.80 (m, 1H), 2.68 (s, 3H), 2.56 (m, 1H), 2.06 (m, 2H), 1.71 (m, 2H), 1.49 (m, 4H), 1.12 (m, 6H). | 455 |
| 4D | | (CDCl$_3$) δ 6.74 (m, 3H), 4.74 (m, 1H), 4.43 (m, 1H), 4.24 (m, 1H), 3.89 (m, 2H), 3.63 (m, 2H), 3.09 (m, 1H), 2.92 (m, 2H), 2.66 (s, 3H), 2.56 (m, 1H), 2.31 (m, 2H), 2.06 (m, 2H), 1.69 (m, 4H), 1.47 (m, 4H), 0.96 (t, J = 7.2 Hz, 3H). | 455 |

-continued

| Example | | ¹H NMR | MS (M + H)⁺ |
|---|---|---|---|
| 4E | | (CDCl₃) δ 6.75 (m, 3H), 4.72 (m, 1H), 4.46 (m, 1H), 4.28 (m, 1H), 4.22 (m, 1H), 3.89 (m, 1H), 3.63 (m, 2H), 3.16 (m, 1H), 2.92 (m, 2H), 2.68 (s, 3H), 2.62 (m, 1H), 2.06 (m, 2H), 1.42-1.78 (m, 7H), 0.97 (m, 2H), 0.75 (m, 2H). | 453 |
| 4F | | (CDCl₃) δ 6.72 (m, 3H), 4.69 (m, 1H), 4.41 (m, 1H), 4.27 (m, 1H), 3.84 (m, 1H), 3.74 (m, 1H), 3.62 (m, 2H), 3.24 (m, 1H), 2.83-3.05 (m, 4H), 2.65 (s, 3H), 2.56 (m, 1H), 2.34 (m, 2H), 1.74-2.20 (m, 5H), 1.65 (m, 2H), 1.46 (m, 4H). | 467 |
| 4G | | (CDCl₃) δ 7.46 (m, 1H), 7.30 (m, 1H), 7.05 (m, 1H), 6.78 (m, 3H), 4.55 (m, 3H), 4.24 (m, 1H), 3.87 (m, 1H), 3.64 (m, 2H), 2.97 (m, 4H), 2.71 (s, 3H), 2.08 (m, 2H), 1.37-1.78 (m, 6H). | 495 |
| 4H | | (CDCl₃) δ 8.66 (m, 2H), 7.77 (m, 1H), 7.37 (m, 1H), 6.75 (m, 3H), 4.81 (m, 1H), 4.51 (m, 1H), 4.25 (m, 1H), 3.84 (m, 2H), 3.63 (m, 2H), 3.18 (m, 1H), 2.89 (m, 3H), 2.71 (s, 3H), 2.05 (m, 2H), 1.4-2.0 (m, 6H). | 490 |
| 4I | | (CDCl₃) δ 6.74 (m, 3H), 4.37 (m, 1H), 4.23 (m, 1H), 3.88 (m, 3H), 3.64 (m, 2H), 2.95 (m, 5H), 2.71 (s, 3H), 2.05 (m, 2H), 1.71 (m, 5H), 1.49 (m, 2H), 1.36 (t, J = 7.4 Hz, 3H). | 477 |
| 4J | | (CDCl₃) δ 6.74 (m, 3H), 4.37 (m, 1H), 4.25 (m, 1H), 3.87 (m, 3H), 3.63 (m, 2H), 2.87 (m, 5H), 2.71 (s, 3H), 2.05 (m, 2H), 1.83 (m, 2H), 1.69 (m, 5H), 1.49 (m, 2H), 1.05 (t, J = 7.8 Hz, 3H). | 491 |

| Example | ¹H NMR | MS (M + H)⁺ |
|---|---|---|
| 4K 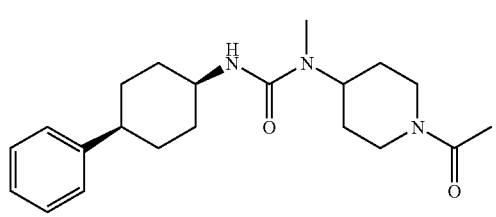 | (CDCl₃) δ 6.74 (m, 3H), 4.39 (m, 1H), 4.24 (m, 1H), 3.90 (m, 3H), 3.61 (m, 2H), 3.16 (m, 1H), 2.93 (m, 4H), 2.71 (s, 3H), 2.05 (m, 2H), 1.68 (m, 4H), 1.49 (m, 2H), 1.33 (d, J = 6.4 Hz, 6H). | 491 |
| 4L | (CDCl₃) δ 7.77 (m, 2H), 7.56 (m, 3H), 6.74 (m, 3H), 4.18 (m, 2H), 3.84 (m, 3H), 3.62 (m, 2H), 2.92 (m, 2H), 2.68 (s, 3H), 2.36 (m, 2H), 2.03 (m, 2H), 1.69 (m, 4H), 1.47 (m, 2H). | 525 |

Example 5A

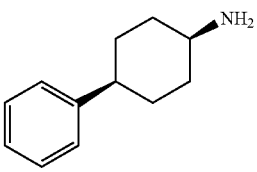

5A

Step 1. Synthesis of 29 and 30

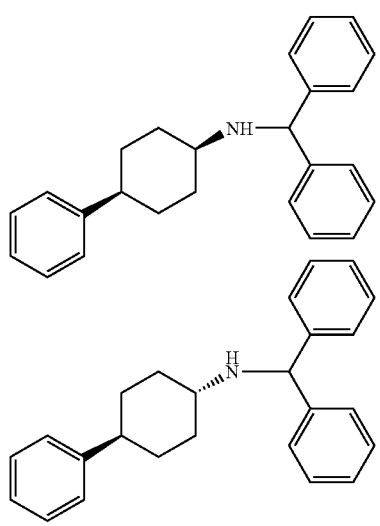

29

30

A mixture of 4-phenylcyclohexanone (1.7 g, 10 mmol) and benzhydrylamine (2.0 g, 11 mmol) in DME (60 ml) was stirred at room temperature for 2 hours. Then Na(OAc)₃BH (3.2 g, 15 mmol) was added. After the reaction mixture was stirred at room temperature for 2 days, 1N NaOH (100 ml) was added. The solution was extracted with CH₂Cl₂ (3×100 ml). The combined organic layer was separated and dried over potassium carbonate. The concentrated residue was separated by flash column chromatography (CH₂Cl₂:hexane 1:9→100:0, v/v) to give 29 (2.13 g) and 30 (0.68 g), total yield being 82%. MS m/e 342 (M+H)⁺.

Step 2. Synthesis of 31

31

To a solution of 29 (1.9 g, 5.6 mmol) in MeOH (100 ml) was added formic acid (4.50 ml, 119 mmol) and 10% Pd/C (1.9 g. 1.8 mmol). The reaction mixture was stirred at room temperature for 16 hours. It was filtered via celite and the celite was washed with 2M ammonia/MeOH. The filtrate was concentrated, then diluted with CH₂Cl₂ (100 ml), and washed with water (50 ml). The aqueous layer was adjusted to pH 11 with ammonia hydroxide solution, then extracted with CH₂Cl₂ (3×100 ml). The combined organic layer was separated, dried over magnesium sulfate and concentrated to give 31 (0.90 g, 92%). MS m/e 176 (M+H)⁺.

Step 3. Synthesis of 32

32

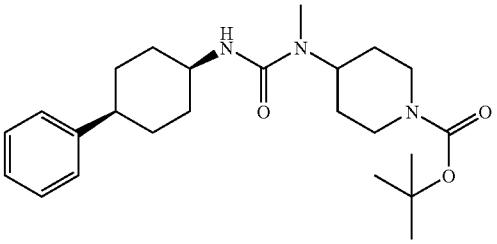

To a solution of 31 (0.90 g, 5.1 mmol) in THF (80 ml) added pyridine (2.0 ml, 24 mmol). The mixture was cooled in an ice water-bath, and N,N'-disuccinimidyl carbonate (1.45 g, 5.66 mmol) was added at 0° C. The mixture was stirred at room temperature for 3.5 hours and cooled to 0° C., 1-tert-butoxycarbonyl-4-methylaminopiperidine (1.15 g, 5.37 mmol) was added. The reaction mixture was stirred at room temperature for 16 hours. The mixture was concentrated to give crude 32 (2.1 g, 96%). MS m/e 416 (M+H)$^+$.

Step 4. Synthesis of 33

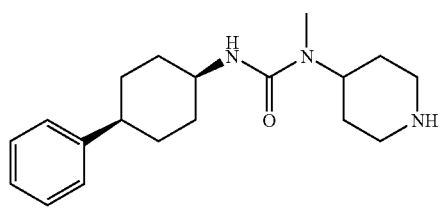

33

A solution of 32 (2.05 g, 4.94 mmol) in 4N HCl/1,4-dioxane (100 ml) was stirred at room temperature for 5 hours. The concentrated residue was washed with ether to give 33 (1.83 g, 100%). MS m/e 316 (M+H)$^+$.

Step 5

To a solution of 33 (0.07 g, 0.2 mmol) and Et$_3$N (0.20 ml, 1.4 mmol) in CH$_2$Cl$_2$ (2 ml) was added acetic anhydride (0.040 ml, 0.43 mmol) at 0° C. and the reaction mixture was stirred for another 1 hour at 0° C. The concentrated residue was separated by PTLC (CH$_2$Cl$_2$:MeOH 20:1, v/v) to give 5A (0.055 g, 77%).

Using essentially the same procedure, 5B was prepared.

Example 5C

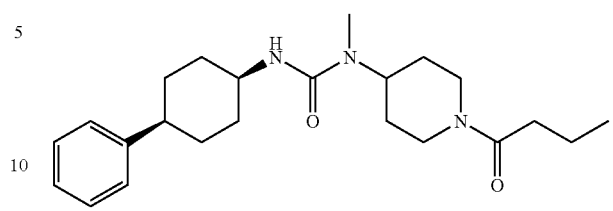

5C

To a solution of 33 (0.07 g, 0.2 mmol) and Et$_3$N (0.20 ml, 1.4 mmol) in CH$_2$Cl$_2$ (2 ml) was added butyryl chloride (0.040 ml, 0.38 mmol) at 0° C. The reaction mixture was stirred at room temperature for 30 minutes. PS-Trisamine resin (100 mg) was added and the mixture was stirred for another 2 hours, then filtered. The filtrate was concentrated and the residue was separated by PTLC (CH$_2$Cl$_2$:MeOH 20:1, v/v) to give 5C (0.055 g, 71%).

Using essentially the same procedure, 5D and 5E were prepared.

Example 5F

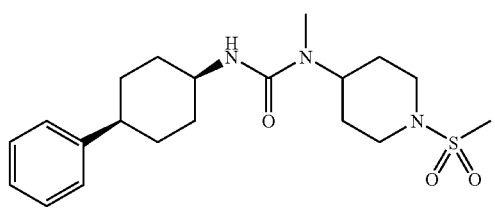

5F

To a solution of 33 (0.07 g, 0.2 mmol) and Et$_3$N (0.20 ml, 1.4 mmol) in CH$_2$Cl$_2$ (2 ml) was added methanesulfonyl chloride (0.040 ml, 0.52 mmol) at 0° C. The reaction mixture was stirred at room temperature for 1 hour. PS-Trisamine (100 mg) was added and the mixture was stirred for another hour. It was filtered and the filtrate was concentrated. The residue was separated by PTLC (CH$_2$Cl$_2$:MeOH 20:1, v/v) to give 5F (0.046 g, 59%).

Using essentially the same procedure, Examples 5G, 5H, 5I, and 5J were prepared.

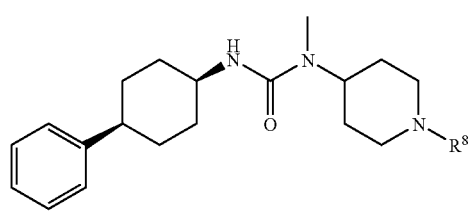

| Example | | $^1$H NMR | MS (M + H)$^+$ |
|---|---|---|---|
| 5A | 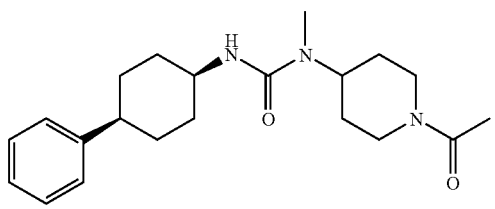 | (CDCl$_3$) δ 7.31 (m, 2H), 7.20 (m, 3H), 4.72 (m, 1H), 4.58 (m, 1H), 4.48 (m, 1H), 4.10 (m, 1H), 3.85 (m, 1H), 3.18 (m, 1H), 2.73 (s, 3H), 2.60 (m, 2H), 2.09 (s, 3H), 1.90-1.44 (m, 11H). | 358 |

-continued

| Example | | ¹H NMR | MS (M + H)⁺ |
|---|---|---|---|
| 5B | | (CDCl₃) δ 7.31 (m, 2H), 7.20 (m, 3H), 4.75 (m, 1H), 4.58 (m, 1H), 4.48 (m, 1H), 4.08 (m, 1H), 3.90 (m, 1H), 3.10 (m, 1H), 2.72 (s, 3H), 2.60 (m, 2H), 2.36 (m, 2H), 1.90-1.40 (m, 11H), 1.12 (m, 3H). | 372 |
| 5C | | (CDCl₃) δ 7.31 (m, 2H), 7.20 (m, 3H), 4.78 (m, 1H), 4.58 (m, 1H), 4.42 (m, 1H), 4.08 (m, 1H), 3.90 (m, 1H), 3.10 (m, 1H), 2.72 (s, 3H), 2.60 (m, 2H), 2.30 (m, 2H), 1.95-1.40 (m, 13H), 0.96 (t, J = 7.6 Hz, 3H). | 386 |
| 5D | | (CDCl₃) δ 7.31 (m, 2H), 7.20 (m, 3H), 4.78 (m, 1H), 4.54 (m, 1H), 4.45 (m, 1H), 4.08 (m, 1H), 3.98 (m, 1H), 3.10 (m, 1H), 2.80 (m, 1H), 2.73 (s, 3H), 2.60 (m, 2H), 1.98-1.40 (m, 11H), 1.11 (dd, J = 6.8 Hz, J = 12 Hz, 6H). | 386 |
| 5E | | (CDCl₃) δ 7.29 (m, 2H), 7.21 (m, 3H), 4.70 (m, 1H), 4.50 (m, 2H), 4.28 (m, 1H), 4.10 (m, 1H), 3.18 (m, 1H), 2.74 (s, 3H), 2.81 (m, 2H), 1.98-1.42 (m, 12H), 0.97 (m, 2H), 0.75 (m, 2H). | 384 |
| 5F | | (CDCl₃) δ 7.32 (m, 2H), 7.22 (m, 3H), 4.57 (m, 1H), 4.40 (m, 1H), 4.08 (m, 1H), 3.88 (m, 2H), 2.80-2.65 (m, 8H), 2.60 (m, 1H), 1.90-1.52 (m, 11H). | 394 |
| 5G | | (CDCl₃) δ 7.30 (m, 2H), 7.21 (m, 3H), 4.58 (m, 1H), 4.40 (m, 1H), 4.05 (m, 1H), 3.90 (m, 2H), 2.94 (m, 3H), 2.86 (m, 1H), 2.76 (s, 3H), 2.60 (m, 1H), 1.98-1.50 (m, 11H), 1.34 (t, J = 7.6 Hz, 3H). | 408 |

-continued

| Example | | $^1$H NMR | MS (M + H)$^+$ |
|---|---|---|---|
| 5H | | (CD$_3$OD) δ 6.93 (m, 4H), 6.82 (m, 1H), 3.88 (m, 1H), 3.60 (m, 1H), 3.48 (m, 2H), 2.97 (m, 1H), 2.65 (m, 2H), 2.55 (m, 2H), 2.47 (s, 3H), 2.30 (m, 1H), 1.60-1.20 (m, 13H), 0.72 (t, J = 7.2 Hz, 3H). | 422 |
| 5I | | (CD$_3$OD) δ 7.26 (m, 4H), 7.18 (m, 1H), 4.22 (m, 1H), 4.00-3.80 (m, 3H), 3.30 (m, 2H), 2.98 (m, 2H), 2.80 (s, 3H), 2.62 (m, 1H), 1.98-1.58 (m, 11H), 1.30 (d, J = 7.2 Hz, 6H). | 422 |
| 5J | | (CD$_3$OD) δ 7.29 (m, 2H), 7.21 (m, 3H), 4.78 (m, 1H), 4.40 (m, 1H), 4.08 (m, 1H), 3.85 (m, 2H), 2.88 (m, 2H), 2.77 (s, 3H), 2.60 (m, 1H), 2.26 (m, 1H), 1.98-1.50 (m, 11H), 1.16 (m, 2H), 0.98 (m, 2H). | 420 |

Example 6A

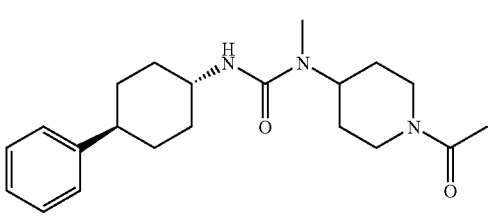

6A

Step 1. Synthesis of 34

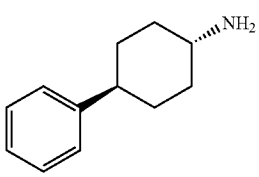

34

A mixture of 30 (2.0 g, 5.8 mmol) and 10% Pd/C (2.0 g) in 4.4% HCOOH/MeOH (100 ml) was stirred at room temperature for 16 hours. The mixture was filtered through a pad of celite and the pad was washed with MeOH. The filtrate was concentrated and the residue was purified by column chromatography (gradient of CH$_2$Cl$_2$ to 1:9 MeOH/CH$_2$Cl$_2$ to 1:5 2M NH$_3$/MeOH in CH$_2$Cl$_2$) to give 34 (0.86 g, 84%). MS m/e 176 (M+H)$^+$.

Step 2. Synthesis of 35

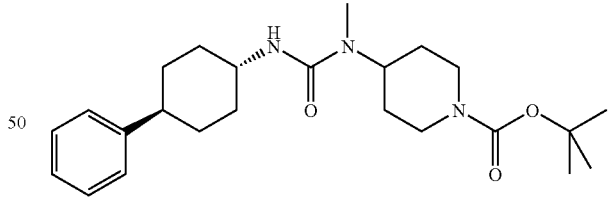

35

To an ice-cold solution of 34 (0.86 g, 4.9 mmol) and pyridine (2.0 ml, 24 mmol) in THF (60 ml) was added N,N'-disuccinimidylcarbonate (1.38 g, 5.39 mmol). The mixture was stirred at room temperature for 3 hours and then cooled in an ice-water bath. 1-tert-Butoxycarbonyl4-methylaminopiperidine (1.10 g, 5.14 mmol) was added and the mixture was stirred at room temperature for 16 hours. The reaction mixture was evaporated to dryness and the residue was partitioned between CH$_2$Cl$_2$ (200 ml) and 1N NaOH (100 ml). The organic layer was washed with water and brine, dried over MgSO$_4$, and concentrated. The crude product was purified by column chromatography (CH$_2$Cl$_2$, then 2:98 MeOH/CH$_2$Cl$_2$) to give 35 (1.8 g, 88%). MS m/e 416 (M+H)$^+$.

Step 3. Synthesis of 36

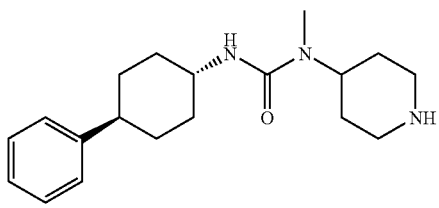

A solution of 35 (1.7 g, 4.1 mmol) in 4N HCl/1,4-dioxane (150 ml) was stirred at room temperature for 3 hours. The concentrated residue was triturated with ether to give 36 (1.38 g, 95%). MS m/e 316 (M+H)$^+$.

Step 4

A solution of 36 (70 mg, 0.22 mmol), acetic anhydride (40 μl, 0.43 mmol), and Et$_3$N (200 μl, 1.43 mmol) in CH$_2$Cl$_2$ (2.5 ml) was stirred at room temperature for 1 hour. The concentrated residue was purified by PTLC (20:1 CH$_2$Cl$_2$/MeOH) to give 6A (60 mg, 76%).

Using essentially the same procedure, 6B was prepared.

Example 6C

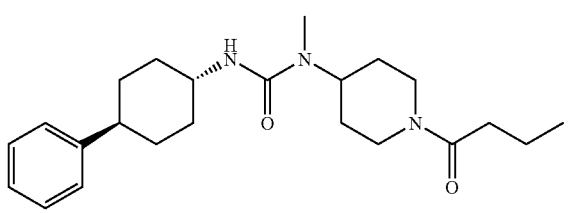

To a solution of 36 (70 mg, 0.22 mmol) and Et$_3$N (200 μl, 1.43 mmol) in CH$_2$Cl$_2$ (2.5 ml) in an ice-water bath was added butyryl chloride (40 μl, 0.38 mmol). The mixture was warmed to room temperature and stirred for 1 hour. PS-Trisamine resin (100 mg) was added and the mixture was stirred for another 2 hours, then filtered. The filtrate was concentrated and the residue was purified by PTLC (10:1 CH$_2$Cl$_2$/MeOH) to give 6C (60 mg, 71%).

Using essentially the same procedure, 6D and 6E were prepared.

Example 6F

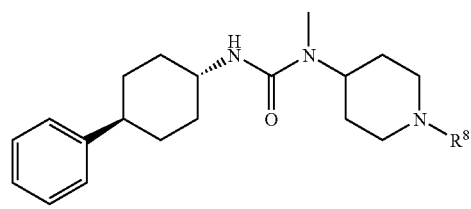

To a solution of 36 (70 mg, 0.22 mmol) and Et$_3$N (200 μl, 1.43 mmol) in CH$_2$Cl$_2$ (2.5 ml) in an ice-water bath was added methanesulfonyl chloride (40 μl, 0.52 mmol). The mixture was stirred at room temperature for 1 hour. PS-Trisamine (100 mg) was added and the mixture was stirred for 2 hours, then filtered. The filtrate was concentrated and the residue was purified by PTLC (10:1 CH$_2$Cl$_2$/MeOH) to give 6F (35 mg, 40%).

Using essentially the same procedure, examples 6G, 6H, 6I, and 6J were prepared.

| Example | | $^1$H NMR | MS (M + H)$^+$ |
|---|---|---|---|
| 6A | 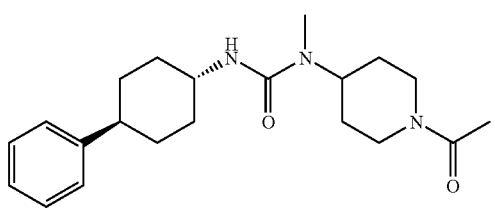 | (CDCl$_3$) δ 7.18-7.31 (m, 5H), 4.73 (m, 1H), 4.47 (m, 1H), 4.20 (m, 1H), 3.87 (m, 1H), 3.74 (m, 1H), 3.15 (m, 1H), 2.69 (s, 3H), 2.59 (m, 1H), 2.48 (m, 1H), 2.14 (m, 2H), 2.10 (s, 3H), 1.94 (m, 2H), 1.4-1.8 (m, 6H), 1.27 (m, 2H). | 358 |

-continued
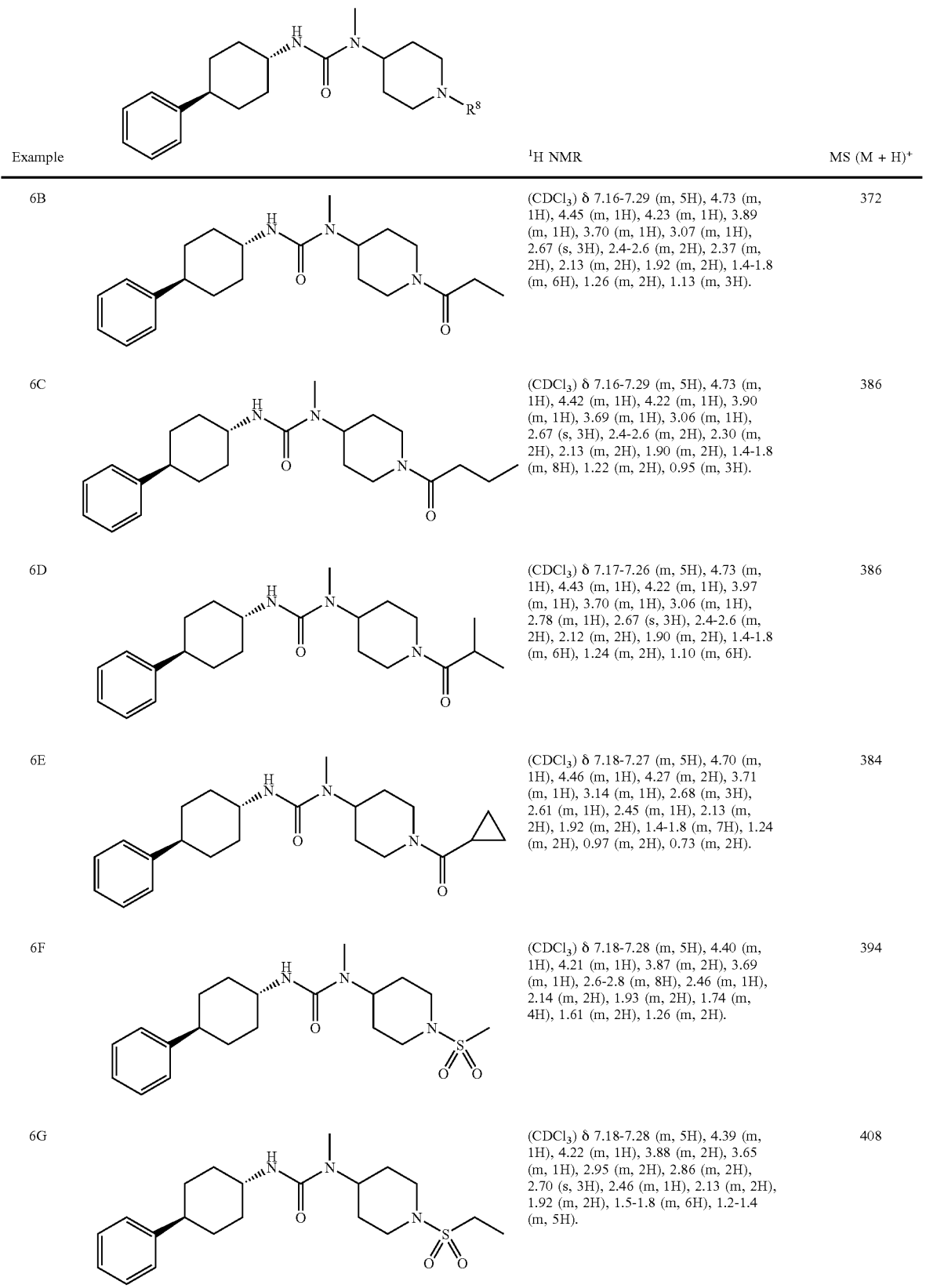
| Example | | ¹H NMR | MS (M + H)⁺ |
|---|---|---|---|
| 6B | | (CDCl₃) δ 7.16-7.29 (m, 5H), 4.73 (m, 1H), 4.45 (m, 1H), 4.23 (m, 1H), 3.89 (m, 1H), 3.70 (m, 1H), 3.07 (m, 1H), 2.67 (s, 3H), 2.4-2.6 (m, 2H), 2.37 (m, 2H), 2.13 (m, 2H), 1.92 (m, 2H), 1.4-1.8 (m, 6H), 1.26 (m, 2H), 1.13 (m, 3H). | 372 |
| 6C | | (CDCl₃) δ 7.16-7.29 (m, 5H), 4.73 (m, 1H), 4.42 (m, 1H), 4.22 (m, 1H), 3.90 (m, 1H), 3.69 (m, 1H), 3.06 (m, 1H), 2.67 (s, 3H), 2.4-2.6 (m, 2H), 2.30 (m, 2H), 2.13 (m, 2H), 1.90 (m, 2H), 1.4-1.8 (m, 8H), 1.22 (m, 2H), 0.95 (m, 3H). | 386 |
| 6D | | (CDCl₃) δ 7.17-7.26 (m, 5H), 4.73 (m, 1H), 4.43 (m, 1H), 4.22 (m, 1H), 3.97 (m, 1H), 3.70 (m, 1H), 3.06 (m, 1H), 2.78 (m, 1H), 2.67 (s, 3H), 2.4-2.6 (m, 2H), 2.12 (m, 2H), 1.90 (m, 2H), 1.4-1.8 (m, 6H), 1.24 (m, 2H), 1.10 (m, 6H). | 386 |
| 6E | | (CDCl₃) δ 7.18-7.27 (m, 5H), 4.70 (m, 1H), 4.46 (m, 1H), 4.27 (m, 2H), 3.71 (m, 1H), 3.14 (m, 1H), 2.68 (m, 3H), 2.61 (m, 1H), 2.45 (m, 1H), 2.13 (m, 2H), 1.92 (m, 2H), 1.4-1.8 (m, 7H), 1.24 (m, 2H), 0.97 (m, 2H), 0.73 (m, 2H). | 384 |
| 6F | | (CDCl₃) δ 7.18-7.28 (m, 5H), 4.40 (m, 1H), 4.21 (m, 1H), 3.87 (m, 2H), 3.69 (m, 1H), 2.6-2.8 (m, 8H), 2.46 (m, 1H), 2.14 (m, 2H), 1.93 (m, 2H), 1.74 (m, 4H), 1.61 (m, 2H), 1.26 (m, 2H). | 394 |
| 6G | | (CDCl₃) δ 7.18-7.28 (m, 5H), 4.39 (m, 1H), 4.22 (m, 1H), 3.88 (m, 2H), 3.65 (m, 1H), 2.95 (m, 2H), 2.86 (m, 2H), 2.70 (s, 3H), 2.46 (m, 1H), 2.13 (m, 2H), 1.92 (m, 2H), 1.5-1.8 (m, 6H), 1.2-1.4 (m, 5H). | 408 |

| Example | | $^1$H NMR | MS (M + H)$^+$ |
|---|---|---|---|
| 6H | | (CDCl$_3$) δ 7.18-7.28 (m, 5H), 4.39 (m, 1H), 4.21 (m, 1H), 3.88 (m, 2H), 3.72 (m, 1H), 2.88 (m, 4H), 2.71 (s, 3H), 2.46 (m, 1H), 2.14 (m, 2H), 1.5-2.0 (m, 10H), 1.26 (m, 2H), 1.04 (m, 3H). | 422 |
| 6I | | (CDCl$_3$) δ 7.19-7.28 (m, 5H), 4.41 (m, 1H), 4.21 (m, 1H), 3.91 (m, 2H), 3.72 (m, 1H), 3.17 (m, 1H), 2.96 (m, 2H), 2.71 (s, 3H), 2.47 (m, 1H), 2.14 (m, 2H), 1.93 (m, 2H), 1.5-1.8 (m, 6H), 1.33 (d, J = 6.8 Hz, 6H), 1.26 (m, 2H). | 422 |
| 6J | | (CDCl$_3$) δ 7.16-7.30 (m, 5H), 4.37 (m, 1H), 4.24 (m, 1H), 3.87 (m, 2H), 3.71 (m, 1H), 2.89 (m, 2H), 2.71 (s, 3H), 2.47 (m, 1H), 2.25 (m, 1H), 2.13 (m, 2H), 1.93 (m, 2H), 1.5-1.8 (m, 6H), 1.28 (m, 2H), 1.15 (m, 2H), 0.98 (m, 2H). | 420 |

Example 7A

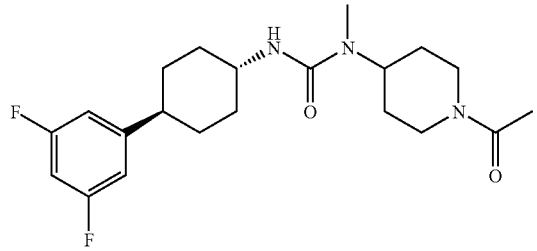

7A

Step 1. Synthesis of 37

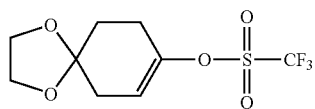

37

To a solution of diisopropylamine (3.75 g, 37.1 mmol) in THF (20 ml) in dry ice-acetone bath was added 2.5 M butyllithium in hexanes (14.4 ml). The mixture was stirred for 10 min and a solution of 1,4-dioxa-spiro[4,5]decan-8-one (5.00 g, 32.0 mmol) in THF (25 ml) was added. After 1 hour, N-phenyltrifluoromethanesulfonimide (11.5 g, 32.3 mmol) in THF (25 ml) was added and the mixture was kept in an ice-water bath. The reaction was allowed to warm to RT slowly and stirred for 16 hours. The volatiles were removed under reduced pressure and the residue was purified by column chromatography (Hexanes gradient to EtOAc:Hexanes 9:1000) to give 37 (6.86 g, 74%). $^1$H-NMR (CDCl$_3$) □ 5.66 (m, 1H), 3.99 (m, 4H), 2.54 (m, 2H), 2.41 (m, 2H), 1.90 (m, 2H).

Step 2. Synthesis of 38

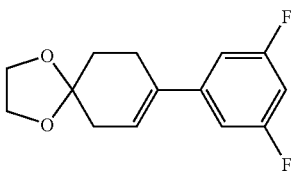

38

A mixture of 37 (4.33 g, 15.0 mmol), 3,5-difluorophenyl boronic acid (3.63 g, 23.0 mmol), lithium chloride (2.60 g, 61.3 mmol), sodium carbonate (6.44 g, 60.8 mmol), and palladium tetrakis(triphenylphosphine) (1.30 g, 1.13 mmol) in DME (50 ml) and water (27 ml) was refluxed under nitrogen for 5 hours. The mixture was cooled down to RT and partitioned between CH$_2$Cl$_2$ (300 ml) and 2N sodium carbonate (200 ml). The aqueous layer was extracted with CH$_2$Cl$_2$ (200 ml) and the combined organic portion was dried, concentrated, and purified by column chromatography (Hexanes gradient to EtOAc:Hexanes 1:40) to give 38 (2.90 g, 90%). $^1$H-NMR (CDCl$_3$) δ 6.87 (m, 2H), 6.65 (m, 1 H), 6.04 (m, 1 H), 4.02 (s, 4H), 2.59 (m, 2H), 2.46 (m, 2H), 1.90 (m, 2H).

Step 3. Synthesis of 39

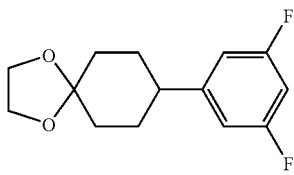

39

A mixture of 38 (0.692 g, 2.75 mmol) and 10% Pd/C (0.100 g) in CH$_3$OH (30 ml) was stirred under 1 atm hydrogen for 4 hours. The mixture was filtered and concentrated to give 39 (0.650 g, 93%). MS m/e 255 (M+H)$^+$.

Step 4. Synthesis of 40

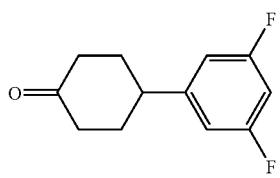

40

A solution of 39 (3.50 g, 13.8 mmol) in THF (60 ml) and 5N HCl (60 ml) was refluxed for 4 hours. The volatiles were removed under reduced pressure and the residue was partitioned between CH$_2$Cl$_2$ and sodium carbonate. The organic portion was dried (MgSO$_4$), concentrated, and purified by column chromatography (Hexanes gradient to EtOAc:Hexanes 1:10) to give 40 (2.00 g, 66%). $^1$H-NMR (CDCl$_3$) δ 6.78 (m, 2H), 6.66 (m, 1H), 3.02 (m, 1H), 2.52 (m, 4H), 2.21 (m, 2H), 1.90 (m, 2H).

Step 5. Synthesis of 41

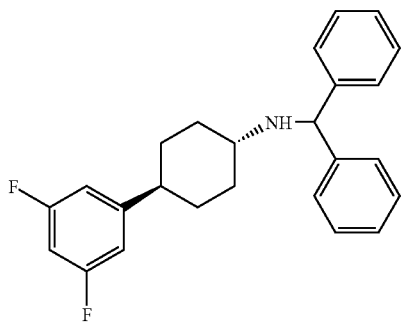

41

A mixture of the 40 (2.00 g, 9.52 mmol), diphenylmethylamine (2.09 g, 11.4 mmol), and sodium triacetoxyborohydride (2.40 g, 11.3 mmol) in dichloroethane (100 ml) was stirred for 16 hours. The mixture was diluted with CH$_2$Cl$_2$ (100 ml) and washed with 1N NaOH (100 ml). The organic portion was passed through a pad of silica, concentrated, and purified by column chromatography (Hexanes gradient to EtOAc:Hexanes 1:50) to give 41 (0.660 g, 18%). MS m/e 378 (M+H)$^+$.

Step 6. Synthesis of 42

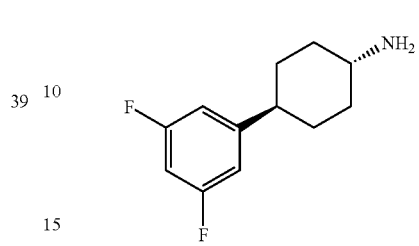

42

A mixture of 41 (0.640 g, 1.70 mmol), ammonium formate (1.90 g, 30.1 mmol), and 10% Pd/C (0.130 g) in CH$_3$OH (30 ml) was stirred at RT for 1 hour. The mixture was filtered through a pad of celite and concentrated. The residue was partitioned between CH$_2$Cl$_2$ (150 ml) and conc. NH$_4$OH (50 ml). The organic portion was dried (K$_2$CO$_3$), concentrated, and purified by column chromatography (CH$_2$Cl$_2$ gradient to 2M NH$_3$/CH$_3$OH:CH$_2$Cl$_2$ 1:10) to give 42 (0.250 g, 70%). MS m/e 212 (M+H)$^+$.

Step 7. Synthesis of 43

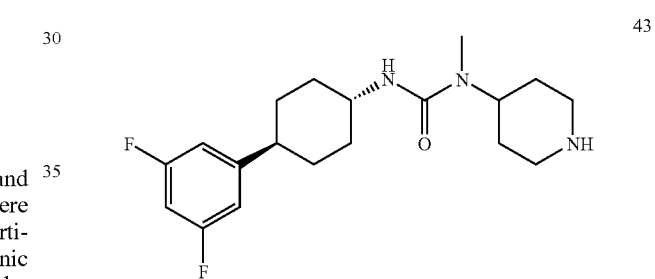

43

To a solution of 42 (0.250 g, 1.18 mmol) and pyridine (1.0 ml, 12 mmol) in an ice-water bath was added N, N'-disuccinimidyl carbonate (0.362 g, 1.42 mmol). The mixture was stirred at RT for 2.5 hours and cooled in an ice-water bath. A solution of 4-methylamino-1-Boc-piperidine (0.278 g, 1.30 mmol) was added and the mixture was stirred at RT for 16 hours. The volatiles were removed under reduced pressure and the residue was partitioned between CH$_2$Cl$_2$ (100 ml) and 1N NaOH (50 ml). The organic portion was washed with 1N HCl, brine, dried (K$_2$CO$_3$), and concentrated. The resulting solid was taken up in CH$_2$Cl$_2$ (25 ml) and 4N HCl/dioxane (25 ml) and the solution was stirred at RT for 2.5 hours. The mixture was concentrated and the residue was partitioned between CH$_2$Cl$_2$ (150 ml) and conc. NH$_4$OH (50 ml). The organic portion was dried (K$_2$CO$_3$), concentrated, and purified by column chromatography (CH$_2$Cl$_2$ gradient to 2M NH$_3$/CH$_3$OH:CH$_2$Cl$_2$ 1:10) to give 43 (0.43 g, 96%). MS m/e 352 (M+H)$^+$.

Step 8

A solution of 43 (0.058 g, 0.15 mmol), acetic anhydride (40 μl, 0.42 mmol), and triethylamine (200 μl, 1.42 mmol) in CH$_2$Cl$_2$ (2 ml) was stirred at RT for 2 hours. 1N NaOH (2 ml) was added and the organic portion was washed with brine, dried (MgSO$_4$), concentrated, and purified by PTLC (CH$_3$OH: CH$_2$Cl$_2$ 1:20) to give 7A (0.036 g, 61%).

Using essentially the same procedure, 7B was prepared.

Example 7C

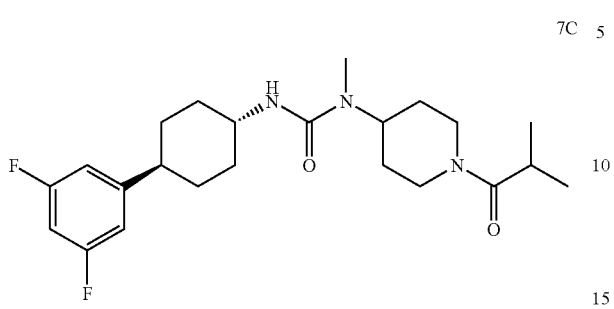

A solution of 43 (0.058 g, 0.15 mmol), isobutyryl chloride (40 μl, 0.38 mmol), and triethylamine (200 μl, 1.42 mmol) in CH$_2$Cl$_2$ (2 ml) was stirred at RT for 16 hours. The mixture was diluted with CH$_2$Cl$_2$ (5 ml) and washed with 1N NaOH (2 ml). The organic portion was dried (MgSO$_4$), concentrated, and purified by PTLC (CH$_3$OH:CH$_2$Cl$_2$ 1:20) to give 7C (0.041 g, 65%).

Using essentially the same procedure, 7D and 7E were prepared.

Example 7F

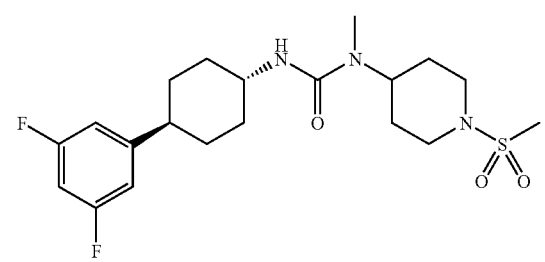

A solution of 43 (0.058 g, 0.15 mmol), methanesulfonyl chloride (40 μl, 0.52 mmol), and triethylamine (200 μl, 1.42 mmol) in CH$_2$Cl$_2$ (2 ml) was stirred at RT for 16 hours. The mixture was diluted with CH$_2$Cl$_2$ (5 ml) and washed with 1N NaOH (2 ml). The organic portion was dried (MgSO$_4$), concentrated, and purified by PTLC (CH$_3$OH:CH$_2$Cl$_2$ 1:20) to give 7F (0.030 g, 47%).

Using essentially the same procedure, 7G, 7H, 7I, and 7J were prepared.

| Example | | $^1$H NMR | MS (M + H)$^+$ |
|---|---|---|---|
| 7A | | (CDCl$_3$) δ 6.71 (m, 2H), 6.61 (m, 1H), 4.72 (m, 1H), 4.46 (m, 1H), 4.22 (m, 1H), 3.86 (m, 1H), 3.69 (m, 1H), 3.14 (m, 1H), 2.68 (s, 3H), 2.58 (m, 1H), 2.46 (m, 1H), 2.12 (m, 2H), 2.09 (s, 3H), 1.92 (m, 2H), 1.68 (m, 2H), 1.52 (m, 4H), 1.25 (m, 2H). | 394 |
| 7B | | (CDCl$_3$) δ 6.71 (m, 2H), 6.62 (m, 1H), 4.75 (m, 1H), 4.46 (m, 1H), 4.18 (m, 1H), 3.91 (m, 1H), 3.71 (m, 1H), 3.09 (m, 1H), 2.68 (s, 3H), 2.59 (m, 1H), 2.47 (m, 1H), 2.34 (m, 2H), 2.15 (m, 2H), 1.93 (m, 2H), 1.4-1.8 (m, 6H), 1.27 (m, 2H), 1.15 (t, J = 7.8 Hz, 3H). | 408 |
| 7C | | (CDCl$_3$) δ 6.71 (m, 2H), 6.58 (m, 1H), 4.74 (m, 1H), 4.44 (m, 1H), 4.21 (m, 1H), 3.97 (m, 1H), 3.69 (m, 1H), 3.09 (m, 1H), 2.78 (m, 1H), 2.66 (s, 3H), 2.56 (m, 1H), 2.44 (m, 1H), 2.14 (m, 2H), 1.93 (m, 2H), 1.4-1.8 (m, 6H), 1.25 (m, 2H), 1.10 (m, 6H). | 422 |

-continued

| Example | | ¹H NMR | MS (M + H)⁺ |
|---|---|---|---|
| 7D | | (CDCl₃) δ 6.71 (m, 2H), 6.62 (m, 1H), 4.75 (m, 1H), 4.46 (m, 1H), 4.18 (m, 1H), 3.91 (m, 1H), 3.71 (m, 1H), 3.11 (m, 1H), 2.68 (s, 3H), 2.58 (m, 1H), 2.46 (m, 1H), 2.31 (m, 2H), 2.16 (m, 2H), 1.93 (m, 2H), 1.4-1.8 (m, 8H), 1.27 (m, 2H), 0.97 (t, J = 7.6 Hz, 3H). | 422 |
| 7E | | (CDCl₃) δ 6.72 (m, 2H), 6.62 (m, 1H), 4.71 (m, 1H), 4.49 (m, 1H), 4.28 (m, 1H), 4.19 (m, 1H), 3.72 (m, 1H), 3.16 (m, 1H), 2.69 (s, 3H), 2.62 (m, 1H), 2.47 (m, 1H), 2.16 (m, 2H), 1.93 (m, 2H), 1.4-1.8 (m, 7H), 1.27 (m, 2H), 0.98 (m, 2H), 0.75 (m, 2H). | 420 |
| 7F | | (CDCl₃) δ 6.72 (m, 2H), 6.62 (m, 1H), 4.39 (m, 1H), 4.21 (m, 1H) 3.89 (m, 2H), 3.71 (m, 1H), 2.78 (s, 3H), 2.75 (m, 2H), 2.71 (s, 3H), 2.46 (m, 1H), 2.15 (m, 2H), 1.93 (m, 2H), 1.72 (m, 4H), 1.56 (m, 2H), 1.27 (m, 2H). | 430 |
| 7G | | (CDCl₃) δ 6.72 (m, 2H), 6.62 (m, 1H), 4.40 (m, 1H), 4.18 (m, 1H), 3.90 (m, 2H), 3.69 (m, 1H), 2.96 (q, J = 7.2 Hz, 2H), 2.87 (m, 2H), 2.71 (s, 3H), 2.47 (m, 1H), 2.15 (m, 2H), 1.92 (m, 2H), 1.4-1.8 (m, 6H), 1.36 (t, J = 7.2 Hz, 3H), 1.24 (m, 2H). | 444 |
| 7H | | (CDCl₃) δ 6.71 (m, 2H), 6.60 (m, 1H), 4.38 (m, 1H), 4.20 (m, 1H), 3.87 (m, 2H), 3.68 (m, 1H), 2.85 (m, 4H), 2.70 (s, 3H), 2.46 (m, 1H), 2.14 (m, 2H), 1.6-2.0 (m, 8H), 1.55 (m, 2H), 1.25 (m, 2H), 1.05 (t, J = 7.2 Hz, 3H). | 458 |
| 7I | | (CDCl₃) δ 6.72 (m, 2H), 6.62 (m, 1H), 4.41 (m, 1H), 4.19 (m, 1H), 3.92 (m, 2H), 3.71 (m, 1H), 3.17 (m, 1H), 2.96 (m, 2H), 2.71 (s, 3H), 2.47 (m, 1H), 2.15 (m, 2H), 1.92 (m, 2H), 1.4-1.8 (m, 6H), 1.33 (d, J = 7.6 Hz, 6H), 1.25 (m, 2H). | 458 |

| Example | | ¹H NMR | MS (M + H)⁺ |
|---|---|---|---|
| 7J | [structure: 3,5-difluorophenyl cyclohexyl urea N-methyl piperidine N-cyclopropylsulfonyl] | (CDCl₃) δ 6.72 (m, 2H), 6.62 (m, 1H), 4.39 (m, 1H), 4.20 (m, 1H), 3.88 (m, 2H), 3.71 (m, 1H), 2.90 (m, 2H), 2.71 (s, 3H), 2.47 (m, 1H), 2.26 (m, 1H), 2.15 (m, 2H), 1.92 (m, 2H), 1.4-1.8 (m, 6H), 1.25 (m, 2H), 1.15 (m, 2H), 0.98 (m, 2H). | 456 |

Example 8A

8A

[structure of compound 8A]

Step 1. Synthesis of 44

44

[structure of compound 44]

A mixture of 37 (6.42 g, 22.3 mmol), 3,5-dichlorophenyl boronic acid (12.8 g, 33.5 mmol), lithium chloride (4.02 g, 94.8 mmol), sodium carbonate (11.7 g, 110 mmol), and palladium tetrakis(triphenylphosphine) (2.01 g, 1.74 mmol) in DME (75 ml) and water (50 ml) was refluxed under nitrogen for 22 hours. The mixture was cooled to RT, diluted with CH₂Cl₂ (200 ml), and washed with 1N NaOH (250 ml). The aqueous portion was extracted with CH₂Cl₂ (2×150 ml) and the combined organic portion was dried (K₂CO₃), concentrated, and purified by column chromatography (Hexanes gradient to EtOAc:Hexanes 1:20) to give 44 (3.60 g, 57%). ¹H-NMR (CDCl₃) δ 7.25 (m, 2H), 7.21 (m, 1H), 6.02 (m, 1H), 4.02 (s, 4H), 2.60 (m, 2H), 2.46 (m, 2H), 1.90 (m, 2H).

Step 2. Synthesis of 45

45

[structure of compound 45]

A mixture of 44 (3.57 g, 12.5 mmol) and 10% Pt/C (0.357 g) in ethanol (120 ml) was stirred under 1 atm hydrogen for 3 hours. The mixture was filtered, concentrated, and purified by column chromatography (Hexanes gradient to EtOAc: Hexanes 1:100) to give 45 (1.70 g, 47%). ¹H-NMR (CDCl₃) δ 7.18 (m, 1H), 7.11 (m, 2H), 3.98 (s, 4H), 2.51 (m, 1H), 1.6-1.9 (m, 8H).

Step 3. Synthesis of 46

46

[structure of compound 46]

A mixture of 45 (1.54 g, 5.36 mmol) and pyridinium p-toluenesulfonate (0.337 g, 1.34 mmol) in acetone (45 ml) and water (5 ml) was refluxed for 24 hours. The mixture was concentrated and the residue was partitioned between CH₂Cl₂ (150 ml) and water (100 ml). The organic portion was washed with 1N HCl (20 ml), 1N NaOH (20 ml), brine (50 ml), dried (K₂CO₃), and concentrated to give 46 (1.30 g, 95%). ¹H-NMR (CDCl₃) δ 7.24 (m, 1H), 7.12 (m, 2H), 2.99 (m, 1H), 2.51 (m, 4H), 2.19 (m, 2H), 1.92 (m, 2H).

Step 4. Synthesis of 47

47

[structure of compound 47]

A solution of 46 (1.20 g, 4.93 mmol) and 1.0M L-selectride (5.5 ml) in THF (15 ml) was stirred in dry ice-acetone bath for 2 hours and then at RT for 16 hours. The reaction was quenched with drops of water, followed by 1N NaOH (10 ml) and aqueous H₂O₂ (10 ml). The mixture was diluted with saturated Na₂CO₃ (150 ml) and extracted by ether (3×50 ml). The combined organic portion was dried (Na₂SO₄), concentrated, and purified by column chromatography (Hexanes gradient to EtOAc:Hexanes 4.5:100) to give 47 (0.764 g, 63%). ¹H-NMR (CDCl₃) δ 7.18 (m, 1H), 7.12 (m, 2H), 4.13 (m, 1H), 2.50 (m, 1H), 1.86 (m, 4H), 1.65 (m, 4H).

Step 5. Synthesis of 48

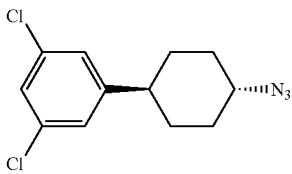

To a solution 47 (0.764 g, 3.11 mmol) and triphenylphosphine (0.863 g, 3.29 mmol) in THF (10 ml) in an ice-water bath were added diethyl azodicarboxylate (0.649 g, 3.72 mmol) and diphenylphosphoryl azide (0.978 g, 3.55 mmol). The mixture was allowed to warm to RT slowly and stirred for 16 hours. The volatiles were removed under reduced pressure and the residue was purified by column chromatography (Hexanes gradient to EtOAc:Hexanes 0.75:100) to give 48 (0.626 g, 75%). $^1$H-NMR (CDCl$_3$) δ 7.20 (m, 1H), 7.07 (m, 2H), 3.33 (m, 1H), 2.48 (m, 1H), 2.14 (m, 2H), 1.96 (m, 2H), 1.48 (m, 4H).

Step 6. Synthesis of 49

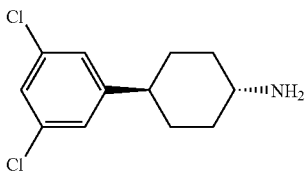

A mixture of 48 (0.626 g, 2.32 mmol) in EtOAc (10 ml) and water (0.2 ml) in an ice-water bath was treated with 1.0M trimethylphosphine in toluene (4.6 ml). The mixture was warmed to RT and stirred for 16 hours. The mixture was evaporated to dryness and purified by column chromatography (CH$_2$Cl$_2$ gradient to 7M NH$_3$/CH$_3$OH:CH$_2$Cl$_2$ 6:1000) to give 49 (0.417 g, 74%). MS m/e 244 (M+H)$^+$.

Step 7. Synthesis of 50

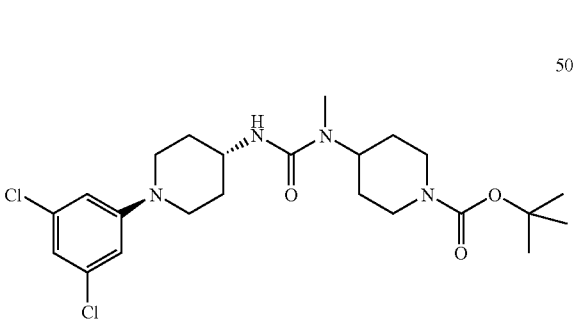

To a solution of 49 (0.417 g, 1.71 mmol) and pyridine (0.492 g, 6.22 mmol) in THF (30 ml) in an ice-water bath was added N, N'-disuccinimidyl carbonate (0.493 g, 1.93 mmol). The mixture was stirred for 30 minutes and more pyridine (0.40 ml, 4.9 mmol) was added. The mixture was then stirred at RT for 3 hours. A solution of 4-methylamino-1-Boc-piperidine (0.456 g, 2.13 mmol) in THF (10 ml) was added and the mixture was stirred at RT for 16 hours. The volatiles were removed under reduced pressure and the residue was partitioned between CH$_2$Cl$_2$ (65 ml) and 1N NaOH (50 ml). The organic portion was washed sequentially with 1N HCl (30 ml) and water (30 ml), dried (MgSO$_4$), concentrated, and purified by column chromatography (CH$_2$Cl$_2$ gradient to CH$_3$OH:CH$_2$Cl$_2$ 0.75:100) to give 50 (0.618 g, 75%). MS m/e 484 (M+H)$^+$.

Step 8. Synthesis of 51

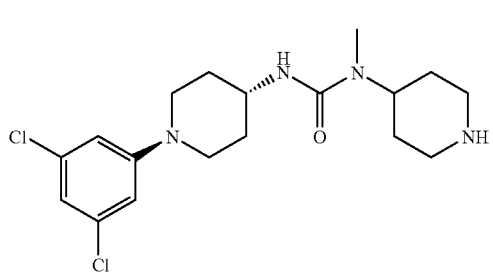

A solution of 50 (0.618 g, 1.28 mmol) in 4N HCl/dioxane (15 ml) was stirred at RT for 16 hours. The volatiles were removed under reduced pressure and the residue was partitioned between CH$_2$Cl$_2$ (2×40 ml) and conc. NH$_4$OH (40 ml). The organic portion was dried (MgSO$_4$) and concentrated to give 51 (0.446 g, 91%). MS m/e 384 (M+H)$^+$.

Step 9

A solution of 51 (0.049 g, 0.13 mmol), acetic anhydride (0.015 g, 0.15 mmol), and triethylamine (0.035 g, 0.35 mmol) in CH$_2$Cl$_2$ (5 ml) was stirred at RT for 16 hours. The solution was diluted with CH$_2$Cl$_2$ (50 ml) and washed with 1N NaOH (25 ml) and 1N HCl (25 ml). The organic portion was dried (MgSO$_4$), concentrated, and purified by PTLC (CH$_3$OH:CH$_2$Cl$_2$ 1:20) to give 8A (0.049 g, 89%).

Example 8B

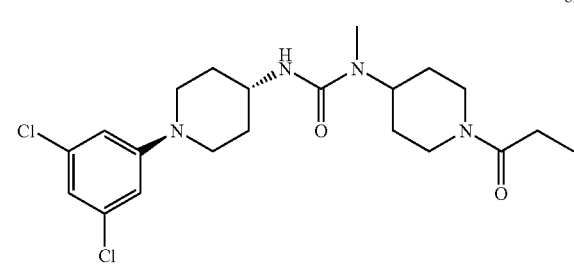

A solution of 51 (0.035 g, 0.090 mmol), propionyl chloride (0.010 g, 0.11 mmol), and triethylamine (0.020 g, 0.20 mmol) in CH$_2$Cl$_2$ (2.5 ml) was stirred at RT for 16 hours. The mixture was purified by PTLC (CH$_3$OH:CH$_2$Cl$_2$ 7:100) to give 8B (0.034 g, 86%).

Using essentially the same procedure, 8C, 8D, and 8E were prepared.

Example 8F

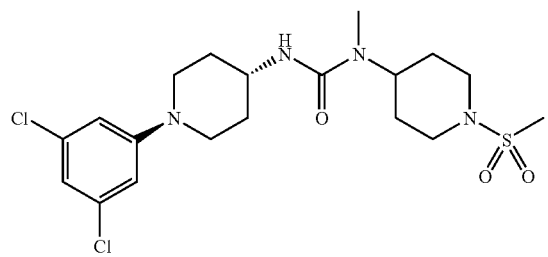

A solution of 51 (0.048 g, 0.13 mmol), methanesulfonyl chloride (0.015 g, 0.13 mmol), and triethylamine (0.033 g, 0.33 mmol) in $CH_2Cl_2$ (5 ml) was stirred at RT for 64 hours. The solution was diluted with $CH_2Cl_2$ (40 ml) and washed with 1N NaOH (20 ml). The organic portion was dried ($MgSO_4$), concentrated, and purified by PTLC ($CH_3OH$: $CH_2Cl_2$ 1:20) to give 8F (0.053 g, 91%).

Using essentially the same procedure, 8G, 8H, and 8I were prepared.

| Example | | $^1$H NMR | MS (M + H)$^+$ |
|---|---|---|---|
| 8A | | (CDCl$_3$) δ 7.18 (m, 1H), 7.07 (m, 2H), 4.73 (m, 1H), 4.46 (m, 1H), 4.21 (m, 1H), 3.86 (m, 1H), 3.69 (m, 1H), 3.14 (m, 1H), 2.68 (s, 3H), 2.58 (m, 1H), 2.44 (m, 1H), 2.14 (m, 2H), 2.10 (s, 3H), 1.90 (m, 2H), 1.4-1.8 (m, 6H), 1.26 (m, 2H). | 426 |
| 8B | | (CDCl$_3$) δ 7.18 (m, 1H), 7.08 (m, 2H), 4.75 (m, 1H), 4.46 (m, 1H), 4.19 (m, 1H), 3.92 (m, 1H), 3.71 (m, 1H), 3.10 (m, 1H), 2.68 (s, 3H), 2.59 (m, 1H), 2.44 (m, 1H), 2.35 (q, J = 7.6 Hz, 2H), 2.15 (m, 2H), 1.91 (m, 2H), 1.4-1.8 (m, 6H), 1.26 (m, 2H), 1.15 (t, J = 7.6 Hz, 3H). | 440 |
| 8C | | (CDCl$_3$) δ 7.18 (m, 1H), 7.08 (m, 2H), 4.76 (m, 1H), 4.46 (m, 1H), 4.18 (m, 1H), 3.93 (m, 1H), 3.72 (m, 1H), 3.10 (m, 1H), 2.68 (s, 3H), 2.57 (m, 1H), 2.44 (m, 1H), 2.29 (m, 2H), 2.16 (m, 2H), 1.90 (m, 2H), 1.4-1.8 (m, 8H), 1.26 (m, 2H), 0.97 (t, J = 7.4 Hz, 3H). | 454 |
| 8D | | (CDCl$_3$) δ 7.18 (m, 1H), 7.07 (m, 2H), 4.75 (m, 1H), 4.46 (m, 1H), 4.19 (m, 1H), 3.99 (m, 1H), 3.72 (m, 1H), 3.11 (m, 1H), 2.80 (m, 1H), 2.68 (s, 3H), 2.57 (m, 1H), 2.44 (m, 1H), 2.17 (m, 2H), 1.91 (m, 2H), 1.4-1.8 (m, 6H), 1.26 (m, 2H), 1.12 (m, 6H). | 454 |

| Example | | ¹H NMR | MS (M + H)⁺ |
|---|---|---|---|
| 8E | 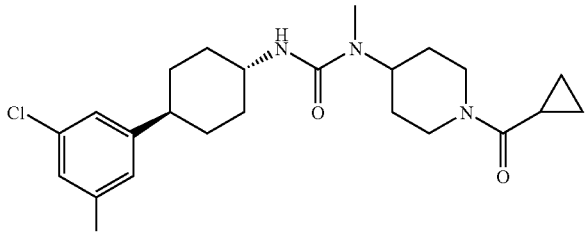 | (CDCl₃) δ 7.18 (m, 1H), 7.07 (m, 2H), 4.71 (m, 1H), 4.48 (m, 1H), 4.30 (m, 1H), 4.21 (m, 1H), 3.71 (m, 1H), 3.15 (m, 1H), 2.69 (s, 3H), 2.63 (m, 1H), 2.45 (m, 1H), 2.16 (m, 2H), 1.92 (m, 2H), 1.4-1.8 (m, 7H), 1.26 (m, 2H), 0.98 (m, 2H), 0.75 (m, 2H). | 452 |
| 8F | 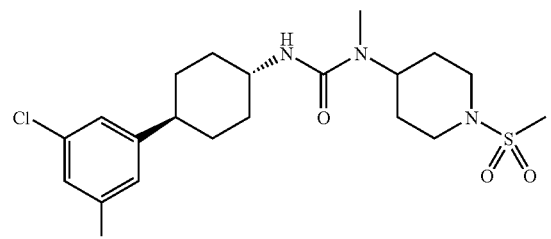 | (CDCl₃) δ 7.18 (m, 1H), 7.07 (m, 2H), 4.39 (m, 1H), 4.23 (m, 1H), 3.88 (m, 2H), 3.69 (m, 1H), 2.79 (s, 3H), 2.76 (m, 2H), 2.72 (s, 3H), 2.45 (m, 1H), 2.15 (m, 2H), 1.92 (m, 2H), 1.75 (m, 4H), 1.56 (m, 2H), 1.25 (m, 2H). | 462 |
| 8G | 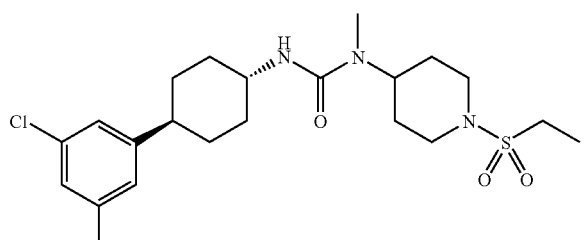 | (CDCl₃) δ 7.18 (m, 1H), 7.07 (m, 2H), 4.39 (m, 1H), 4.22 (m, 1H), 3.90 (m, 2H), 3.69 (m, 1H), 2.95 (q, J = 7.4 Hz, 2H), 2.87 (m, 2H), 2.71 (s, 3H), 2.45 (m, 1H), 2.15 (m, 2H), 1.91 (m, 2H), 1.72 (m, 4H), 1.56 (m, 2H), 1.36 (t, J = 7.4 Hz, 3H), 1.25 (m, 2H). | 476 |
| 8H | 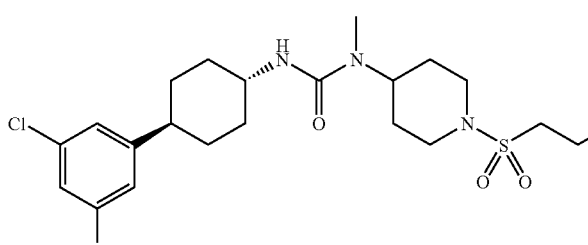 | (CDCl₃) δ 7.18 (m, 1H), 7.07 (m, 2H), 4.39 (m, 1H), 4.21 (m, 1H), 3.89 (m, 2H), 3.69 (m, 1H), 2.86 (m, 4H), 2.71 (s, 3H), 2.44 (m, 1H), 2.15 (m, 2H), 1.87 (m, 4H), 1.71 (m, 4H), 1.55 (m, 2H), 1.25 (m, 2H), 1.06 (t, J = 7.6 Hz, 3H). | 490 |
| 8I | 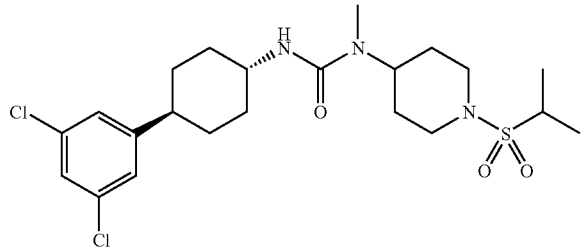 | (CDCl₃) δ 7.18 (m, 1H), 7.08 (m, 2H), 4.41 (m, 1H), 4.21 (m, 1H), 3.92 (m, 2H), 3.70 (m, 1H), 3.18 (m, 1H), 2.96 (m, 2H), 2.71 (s, 3H), 2.45 (m, 1H), 2.15 (m, 2H), 1.91 (m, 2H), 1.68 (m, 4H), 1.56 (m, 2H), 1.33 (d, J = 6.4 Hz, 6H), 1.27 (m, 2H). | 490 |

Example 9A

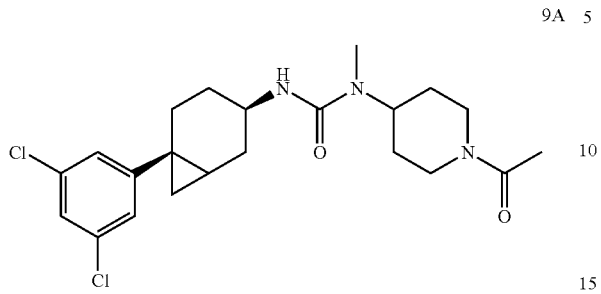

Step 1. Synthesis of 52

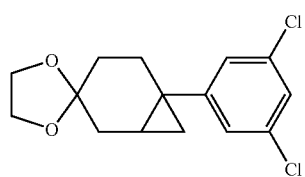

To a solution of 1 M ZnEt$_2$ in hexanes (7.3 ml) in CH$_2$Cl$_2$ (8 ml) in an ice-water bath was added TFA (0.842 g, 7.38 mmol) in CH$_2$Cl$_2$ (6 ml) dropwise. Upon stirring for 20 minutes, a solution of CH$_2$I$_2$ (2.08 g, 7.78 mmol) in CH$_2$Cl$_2$ (4 ml) was added. After an additional 20 minutes, 44 (1.01 g, 3.53 mmol) in CH$_2$Cl$_2$ (5 ml) was added and the reaction was stirred at RT for 40 hours. The mixture was cooled in an ice-water bath and quenched with CH$_3$OH (5 ml), washed with 1N NaOH (60 ml), dried (MgSO$_4$), and purified by column chromatography (Hexanes gradient to EtOAc:Hexanes 1:200) to give 52 (0.608 g, 57%). $^1$H-NMR (CDCl$_3$) δ 7.17 (m, 2H), 7.15 (m, 1H), 3.90 (m, 4H), 2.19 (m, 3H), 1.80 (m, 1H), 1.63 (m, 1H), 1.46 (m, 1H), 1.24 (m, 1H), 1.01 (m, 1H), 0.78 (m, 1H).

Step 2. Synthesis of 53

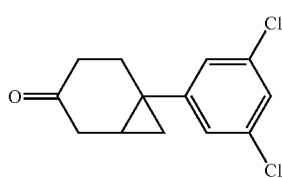

A mixture of 52 (0.606 g, 2.03 mmol) and water (1 ml) in 1:1 TFA-CH$_2$Cl$_2$ (10 ml) was stirred at RT for 2 hours. The volatiles were removed under reduced pressure and the residue was partitioned between EtOAc (50 ml) and saturated Na$_2$CO$_3$ (40 ml). The organic portion was dried (MgSO$_4$) and purified by column chromatography (Hexanes gradient to EtOAc:Hexanes 1:50) to give 53 (0.460 g, 89%). $^1$H-NMR (CDCl$_3$) δ 7.20 (m, 1H), 7.17 (m, 2H), 2.84 (m, 1H), 2.68 (m, 1H), 2.42 (m, 2H), 2.26 (m, 2H), 1.49 (m, 1H), 1.07 (m, 1H), 0.88 (m, 1H).

Step 3. Synthesis of 54 and 55

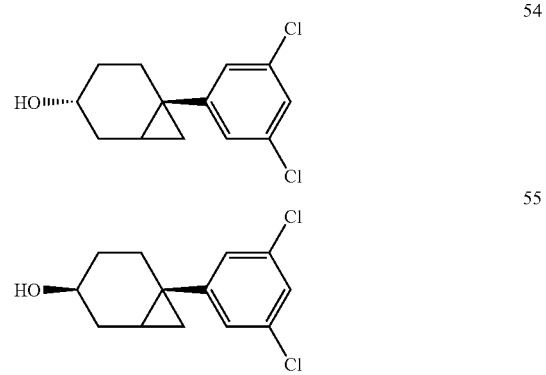

A solution of 53 (0.460 g, 1.80 mmol) and 1M L-selectride (2.0 ml) in THF (7.5 ml) was stirred in a dry ice-acetone bath for 2 hours and then at RT for 3 hours. More 1M L-selectride (0.6 ml) was added and the solution was stirred at RT for 16 hours. The reaction was quenched with several drops of water, 1N NaOH (5 ml), and aqueous H$_2$O$_2$ (5 ml). The mixture was diluted with saturated Na$_2$CO$_3$ (80 ml) and extracted with ether (2×50 ml). The combined organic portion was dried (MgSO$_4$) and purified by PTLC (CH$_3$OH:CH$_2$Cl$_2$ 1:100) to give 54 (0.210 g, 45%) and 55 (0.216 g, 47%).

54 $^1$H-NMR (CDCl$_3$) δ 7.15 (m, 1H), 7.09 (m, 2H), 3.69 (m, 1H), 2.47 (m, 1H), 2.22 (m, 1H), 1.98 (m, 1H), 1.74 (m, 1H), 1.68 (m, 1H), 1.48 (m, 1H), 1.22 (m, 2H), 0.98 (m, 1H), 0.78 (m, 1H).

55 $^1$H-NMR (CDCl$_3$) δ 7.17 (m, 3H), 3.81 (m, 1H), 2.23 (m, 1H), 1.98 (m, 3H), 1.60 (m, 1H), 1.49 (m, 2H), 1.22 (m, 1H), 1.00 (m, 1H), 0.58 (m, 1H).

Step 4. Synthesis of 56

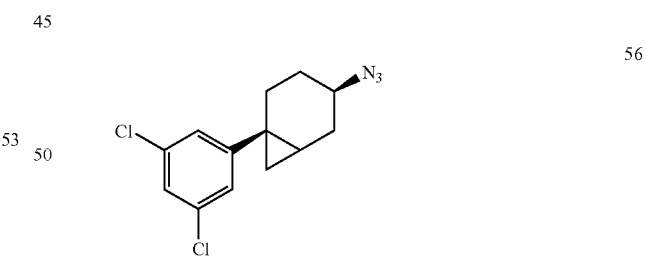

To a solution of 54 (0.209 g, 0.813 mmol) and triphenylphosphine (0.226 g, 0.862 mmol) in THF (5 ml) in an ice-water bath were added diethyl azodicarboxylate (0.222 g, 1.27 mmol) and diphenylphosphoryl azide (0.293 g, 1.06 mmol). The ice-water bath was removed and the mixture was stirred at RT for 16 hours. The volatiles were removed under reduced pressure and the residue was purified by PTLC (EtOAc:Hexanes 1:20) to give 56 (0.113 g, 49%). $^1$H-NMR (CDCl$_3$) δ 7.17 (m, 3H), 3.56 (m, 1H), 2.16 (m, 2H), 1.98 (m, 2H), 1.67 (m, 1H), 1.50 (m, 1H), 1.24 (m, 1H), 1.03 (m, 1H), 0.59 (m, 1H).

Step 5. Synthesis of 57

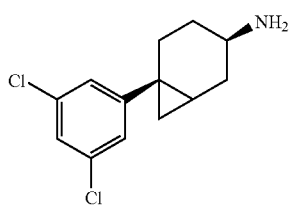

A mixture of 56 (0.112 g, 0.397 mmol) and 1M trimethylphosphine in toluene (0.8 ml) in EtOAc (5 ml) and water (50 µl) was stirred at RT for 16 hours. The mixture was evaporated to dryness and purified by PTLC (7M $NH_3$/$CH_3OH$:$CH_2Cl_2$ 1:50) to give 57 (0.093 g, 92%). MS m/e 256 (M+H)$^+$.

Step 6. Synthesis of 58

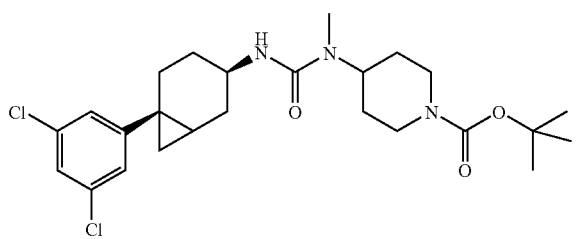

To a mixture of 57 (0.093 g, 0.364 mmol) and N,N'-disuccinimidyl carbonate (0.120 g, 0.469 mmol) in THF (5 ml) in an ice-water bath was added pyridine (0.190 g, 2.40 mmol). The mixture was stirred at 0° C. for 30 minutes then at RT for 3 hours. A solution of 4-methylamino-1-Boc-piperidine (0.098 g, 0.458 mmol) in THF (5 ml) was added and the mixture was stirred at RT for 16 hours. The volatiles were removed under reduced pressure and the residue was partitioned between $CH_2Cl_2$ (40 ml) and 1N NaOH (30 ml). The organic portion was dried ($MgSO_4$) and purified by PTLC ($CH_3OH$:$CH_2Cl_2$ 1:33) to give 58 (0.169 g, 94%). MS m/e 496 (M+H)$^+$.

Step 7. Synthesis of 59

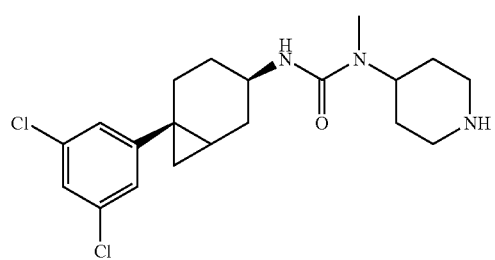

A solution of 58 (0.169 g, 0.341 mmol) in 1:1 TFA-$CH_2Cl_2$ (10 ml) in an ice-water bath was stirred for 30 minutes and then stirred at RT for 16 hours. The volatiles were removed under reduced pressure and the residue was partitioned between $CH_2Cl_2$ (50 ml) and conc. $NH_4OH$ (25 ml). The organic portion was dried ($MgSO_4$) and evaporated to give 59 (0.114 g, 84%). MS m/e 396 (M+H)$^+$.

Step 8

A solution of 59 (0.027 g, 0.069 mmol), acetic anhydride (0.0088 g, 0.086 mmol), and triethylamine (0.013 g, 0.13 mmol) in $CH_2Cl_2$ (5 ml) was stirred at RT for 16 hours. The mixture was evaporated to dryness and purified by PTLC ($CH_3OH$:$CH_2Cl_2$ 1:20) to give 9A (0.029 g, 97%).

Example 9B

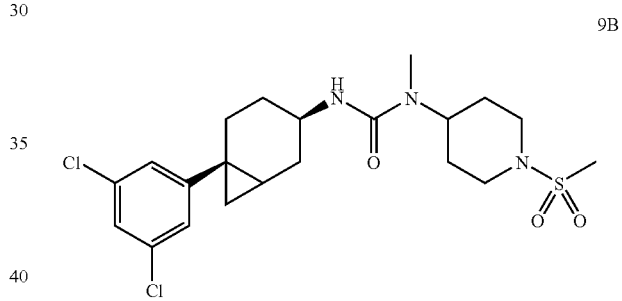

A solution of 59 (0.033 g, 0.082 mmol), methanesulfonyl chloride (0.011 g, 0.096 mmol), and triethylamine (0.020 g, 0.20 mmol) in $CH_2Cl_2$ (5 ml) was stirred at RT for 16 hours. The mixture was evaporated to dryness and purified by PTLC ($CH_3OH$:$CH_2Cl_2$ 1:20) to give 9B (0.037 g, 95%).

| Example | | $^1$H NMR | MS (M + H)$^+$ |
|---|---|---|---|
| 9A | 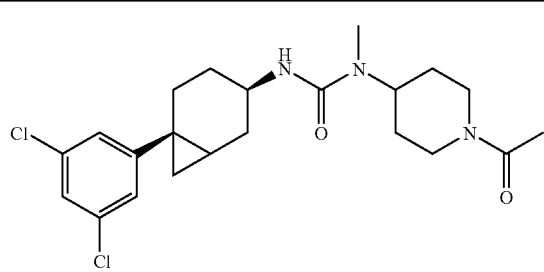 | ($CDCl_3$) δ 7.15 (m, 1H), 7.11 (m, 2H), 4.73 (m, 1H), 4.43 (m, 1H), 4.28 (m, 1H), 3.87 (m, 1H), 3.70 (m, 1H), 3.13 (m, 1H), 2.69 (s, 3H), 2.57 (m, 1H), 2.10 (m, 6H), 1.2-1.9 (m, 8H), 1.04 (m, 1H), 0.71 (m, 1H). | 438 |

-continued

| Example | | ¹H NMR | MS (M + H)⁺ |
|---|---|---|---|
| 9B | 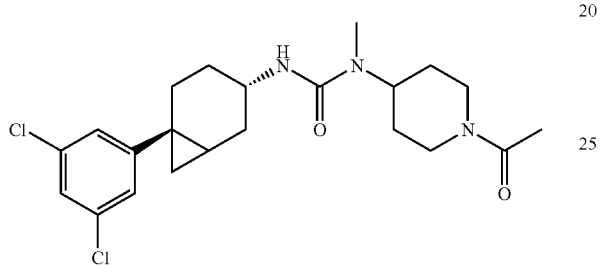 | (CDCl₃) δ 7.15 (m, 1H), 7.10 (m, 2H), 4.34 (m, 2H), 3.88 (m, 2H), 3.69 (m, 1H), 2.78 (s, 3H), 2.75 (m, 2H), 2.72 (s, 3H), 2.09 (m, 3H), 1.74 (m, 5H), 1.43 (m, 2H), 1.29 (m, 1H), 1.03 (m, 1H), 0.71 (m, 1H). | 474 |

Example 10A

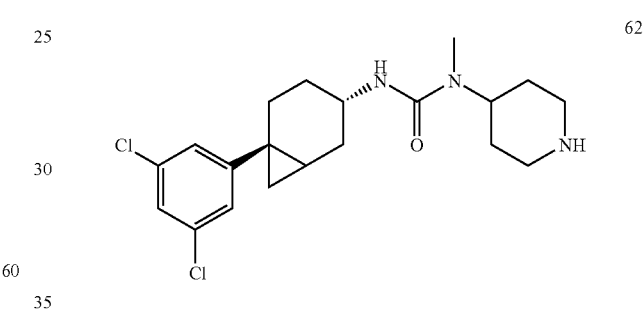

10A

Step 1. Synthesis of 60

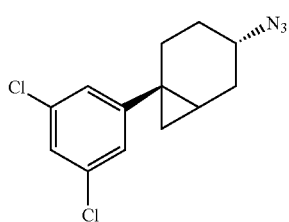

60

To a solution of 55 (0.216 g, 0.842 mmol) and triphenylphosphine (0.246 g, 0.938 mmol) in THF (5 ml) in an ice-water bath were added diethyl azodicarboxylate (0.200 g, 1.15 mmol) and diphenylphosphoryl azide (0.268 g, 0.974 mmol). The ice-water bath was removed and the mixture was stirred at RT for 16 hours. The volatiles were removed under reduced pressure and the residue was purified by PTLC (EtOAc:Hexanes 1:20) to give 60 (0.142 g, 60%). ¹H-NMR (CDCl₃) δ 7.17 (m, 1H), 7.10 (m, 2H), 3.37 (m, 1H), 2.47 (m, 1H), 2.27 (m, 1H), 1.97 (m, 1H), 1.83 (m, 1H), 1.58 (m, 1H), 1.28 (m, 2H), 1.03 (m, 1H), 0.77 (m, 1H).

Step 2. Synthesis of 61

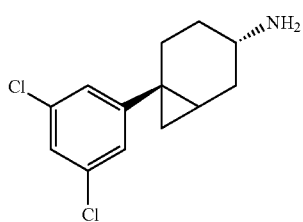

61

A mixture of the 60 (0.142 g, 0.504 mmol) and 1M trimethylphosphine in toluene (1.0 ml) in EtOAc (5 ml) and water (100 μl) was stirred at RT for 16 hours. The mixture was evaporated to dryness and purified by PTLC (7M NH₃/CH₃OH:CH₂Cl₂ 1:33) to give 61 (0.102 g, 79%). MS m/e 256 (M+H)⁺.

Step 3. Synthesis of 62

62

To a mixture of 61 (0.102 g, 0.398 mmol) and N,N'-disuccinimidyl carbonate (0.134 g, 0.524 mmol) in THF (5 ml) in an ice-water bath was added pyridine (0.280 g, 3.54 mmol). The mixture was stirred at 0° C. for 30 minutes then at RT for 3 hours. A solution of 4-methylamino-1-Boc-piperidine (0.120 g, 0.561 mmol) in THF (4 ml) was added and the mixture was stirred at RT for 16 hours. The volatiles were removed under reduced pressure and the residue was partitioned between CH₂Cl₂ (50 ml) and 0.5N HCl (30 ml). The organic portion was washed with 1N NaOH (30 ml), dried (MgSO₄), and concentrated. The resulting solid was taken up in 4N HCl/dioxane (5 ml) and stirred at RT for 16 hours. The volatiles were removed under reduced pressure and the residue was partitioned between EtOAc (2×40 ml) and conc. NH₄OH (35 ml). The organic portion was dried (K₂CO₃), concentrated, and purified by PTLC (2.3M NH₃/CH₃OH:CH₂Cl₂ 3:17) to give 62 (0.089 g, 56%). ¹H-NMR (CD₃OD) δ 7.21 (m, 3H), 4.15 (m, 1H), 3.60 (m, 1H), 3.11 (m, 2H), 2.73 (s, 3H), 2.67 (m, 2H), 2.44 (m, 1H), 2.23 (m, 1H), 2.04 (m, 1H), 1.64 (m, 5H), 1.45 (m, 1H), 1.26 (m, 2H), 0.97 (m, 1H), 0.79 (m, 1H).

Step 4

A solution of the 62 (0.022 g, 0.055 mmol), acetic anhydride (0.0069 g, 0.067 mmol), and triethylamine (0.012 g, 0.12 mmol) in CH₂Cl₂ (5 ml) was stirred at RT for 16 hours. The mixture was evaporated to dryness and purified by PTLC (CH₃OH:CH₂Cl₂ 1:20) to give 10A (0.024 g, 98%).

Using essentially the same procedure, 10B was prepared.

Example 10C

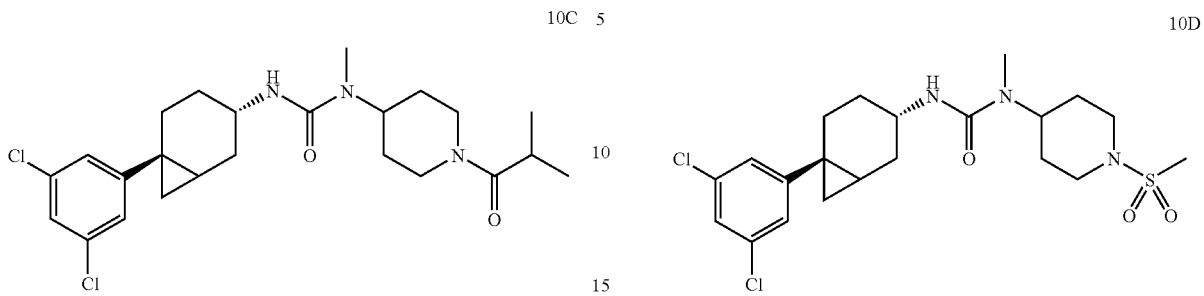

A solution of 62 (0.026 g, 0.068 mmol), isobutyryl chloride (0.0075 g, 0.070 mmol), and triethylamine (0.012 g, 0.12 mmol) in $CH_2Cl_2$ (3 ml) was stirred at RT for 16 hours. The mixture was evaporated to dryness and purified by PTLC ($CH_3OH:CH_2Cl_2$ 1:20) to give 10C (0.029 g, 90%).

Example 10D

A solution of 62 (0.022 g, 0.056 mmol), methanesulfonyl chloride (0.0087 g, 0.075 mmol), and triethylamine (0.011 g, 0.11 mmol) in $CH_2Cl_2$ (5 ml) was stirred at RT for 16 hours. The mixture was evaporated to dryness and purified by PTLC ($CH_3OH:CH_2Cl_2$ 1:20) to give 10D (0.027 g, 100%).

| Example | | $^1$H NMR | MS (M + H)$^+$ |
|---|---|---|---|
| 10A | | (CDCl$_3$) δ 7.15 (m, 1H), 7.12 (m, 2H), 4.72 (m, 1H), 4.44 (m, 1H), 4.08 (m, 1H), 3.86 (m, 1H), 3.65 (m, 1H), 3.14 (m, 1H), 2.66 (s, 3H), 2.57 (m, 2H), 2.21 (m, 1H), 2.10 (s, 3H), 2.05 (m, 1H), 1.83 (m, 1H), 1.68 (m, 2H), 1.51 (m, 2H), 1.27 (m, 2H), 1.08 (m, 1H), 0.98 (m, 1H), 0.70 (m, 1H). | 438 |
| 10B | | (CDCl$_3$) δ 7.15 (m, 1H), 7.11 (m, 2H), 4.75 (m, 1H), 4.43 (m, 1H), 4.08 (m, 1H), 3.90 (m, 1H), 3.66 (m, 1H), 3.09 (m, 1H), 2.66 (s, 3H), 2.57 (m, 2H), 2.35 (q, J = 7.2 Hz, 2H), 2.21 (m, 1H), 2.05 (m, 1H), 1.83 (m, 1H), 1.68 (m, 2H), 1.47 (m, 2H), 1.28 (m, 2H), 1.14 (t, J = 7.2 Hz, 3H), 1.06 (m, 1H), 0.98 (m, 1H), 0.70 (m, 1H). | 452 |
| 10C | | (CDCl$_3$) δ 7.15 (m, 1H), 7.12 (m, 2H), 4.76 (m, 1H), 4.45 (m, 1H), 4.07 (m, 1H), 3.99 (m, 1H), 3.65 (m, 1H), 3.10 (m, 1H), 2.80 (m, 1H), 2.66 (s, 3H), 2.57 (m, 2H), 2.21 (m, 1H), 2.06 (m, 1H), 1.4-1.9 (m, 5H), 1.29 (m, 2H), 1.12 (m, 7H), 0.98 (m, 1H), 0.71 (m, 1H). | 466 |

| Example | | ¹H NMR | MS (M + H)⁺ |
|---|---|---|---|
| 10D | 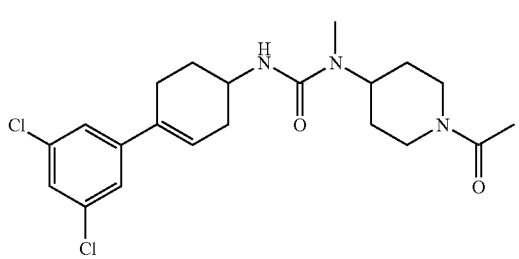 | (CDCl₃) δ 7.15 (m, 1H), 7.12 (m, 2H), 4.38 (m, 1H), 4.10 (m, 1H), 3.88 (m, 2H), 3.66 (m, 1H), 2.79 (s, 3H), 2.75 (m, 2H), 2.70 (s, 3H), 2.57 (m, 1H), 2.23 (m, 1H), 2.06 (m, 1H), 1.76 (m, 5H), 1.29 (m, 2H), 1.09 (m, 1H), 0.99 (m, 1H), 0.71 (m, 1H). | 474 |

Example 11A

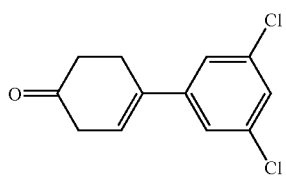
11A

Step 1. Synthesis of 63

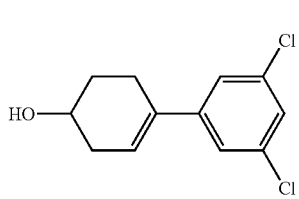
63

A solution of 44 (2.85 g, 10.0 mmol) and pyridinium p-toluenesulfonate (0.628 g, 2.50 mmol) in acetone (90 ml) and water (10 ml) was refluxed for 20 hours. The mixture was concentrated and the residue was partitioned between CH₂Cl₂ (200 ml) and water (100 ml). The organic portion was washed with 1N HCl (30 ml), 1N NaOH (30 ml), brine (50 ml), dried (K₂CO₃), concentrated, and purified by column chromatography (Hexanes gradient to EtOAc:Hexanes 3:100) to give 63 (1.82 g, 76%). ¹H-NMR (CDCl₃) δ 7.27 (m, 3H), 6.15 (m, 1H), 3.08 (m, 2H), 2.84 (m, 2H), 2.64 (m, 2H).

Step 2. Synthesis of 64

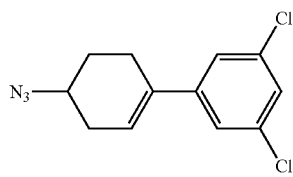
64

A mixture of 63 (1.20 g, 4.98 mmol) and sodium borohydride (0.230 g, 6.08 mmol) in MeOH (50 ml) was stirred at 0° C. for 2 hours. Water (2.5 ml) was added and the mixture was stirred for 30 minutes. The mixture was then concentrated and the residue was partitioned between CH₂Cl₂ (150 ml) and water (100 ml). The organic portion was dried (K₂CO₃) and concentrated to give 64 (1.15 g, 95%). ¹H-NMR (CDCl₃) δ 7.23 (m, 2H), 7.20 (m, 1H), 6.03 (m, 1H), 4.05 (m, 1H), 2.54 (m, 2H), 2.44 (m, 1H), 2.20 (m, 1H), 1.98 (m, 1H), 1.83 (m, 1H).

Step 3. Synthesis of 65

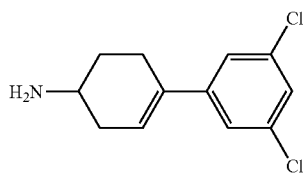
65

To a solution of 64 (1.00 g, 4.12 mmol) and triphenylphosphine (1.13 g, 4.30 mmol) in THF (12 ml) in an ice-water bath were added diethyl azodicarboxylate (0.857 g, 4.92 mmol) and diphenylphosphoryl azide (1.30 g, 4.72 mmol). The ice-water bath was removed and the mixture was stirred at RT for 16 hours. The volatiles were removed under reduced pressure and the residue was taken up in CH₂Cl₂ (100 ml), washed with water and saturated sodium bicarbonate, dried (K₂CO₃), and purified by column chromatography (Hexanes) to give 65 (0.272 g, 25%). ¹H-NMR (CDCl₃) δ 7.23 (m, 3H), 6.04 (m, 1H), 3.76 (m, 1H), 2.54 (m, 2H), 2.45 (m, 1H), 2.30 (m, 1H), 2.07 (m, 1H), 1.88 (m, 1H).

Step 4. Synthesis of 66

66

A mixture of the 65 (0.300 g, 1.12 mmol) and 1M trimethylphosphine in toluene (2.24 ml) in EtOAc (5 ml) and water (100 μl) was stirred at RT for 16 hours. The mixture was evaporated to dryness and purified by column chromatography (2M NH₃/CH₃OH:CH₂Cl₂ 1:20) to give 66 (0.266 g, 98%). MS m/e 242 (M+H)⁺.

Step 5. Synthesis of 67

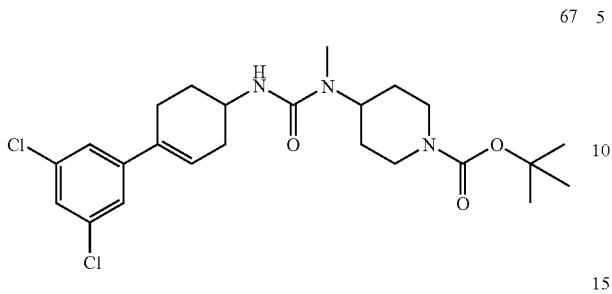

To a mixture of 66 (0.266 g, 1.10 mmol) and N, N'-disuccinimidyl carbonate (0.338 g, 1.32 mmol) in THF (20 ml) in an ice-water bath was added pyridine (0.70 ml, 8.6 mmol). The mixture was stirred at 0° C. for 30 minutes then at RT for 2 hours. A solution of 4-methylamino-1-Boc-piperidine (0.259 g, 1.21 mmol) in THF (5 ml) was added and the mixture was stirred at RT for 16 hours. The volatiles were removed under reduced pressure and the residue was partitioned between $CH_2Cl_2$ (100 ml) and 1N NaOH (50 ml). The organic portion was washed with water and brine, dried ($K_2CO_3$), concentrated, and purified by column chromatography ($CH_2Cl_2$ gradient to MeOH:$CH_2Cl_2$ 1:50) to give 67 (0.520 g, 98%). $^1$H-NMR (CDCl$_3$) δ 7.24 (m, 2H), 7.22 (m, 1H), 6.09 (m, 1H), 4.34 (m, 2H), 4.18 (m, 2H), 4.05 (m, 1H), 2.78 (m, 2H), 2.69 (s, 3H), 2.63 (m, 1H), 2.48 (m, 2H), 2.06 (m, 2H), 1.72 (m, 1H), 1.61 (m, 2H), 1.51 (m, 2H), 1.46 (s, 9H).

Step 6. Synthesis of 68

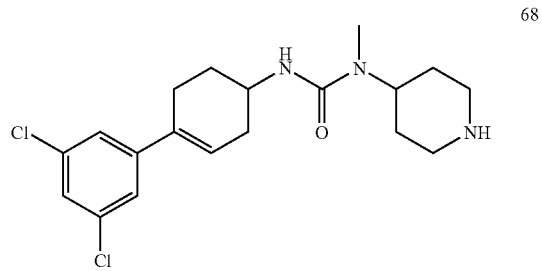

A solution of 67 (0.420 g, 0.871 mmol) in 4N HCl/dioxane (10 ml) and $CH_2Cl_2$ (10 ml) stirred at RT for 2 hours. The mixture was concentrated to give 68 (0.360 g, 99%). $^1$H-NMR (CD$_3$OD) δ 7.34 (m, 2H), 7.27 (m, 1H), 6.16 (m, 1H), 4.34 (m, 1H), 3.89 (m, 1H), 3.48 (m, 2H), 3.10 (m, 2H), 2.81 (s, 3H), 2.52 (m, 3H), 1.6-2.3 (m, 7H).

Step 7

A solution of the 68 (0.050 g, 0.12 mmol), acetic anhydride (40 μl, 0.42 mmol), and triethylamine (200 μl, 1.42 mmol) in $CH_2Cl_2$ (5 ml) was stirred at RT for 4 hours. The mixture was evaporated to dryness and purified by PTLC (CH$_3$OH:CH$_2$Cl$_2$ 1:10) to give 11A (0.038 g, 75%).

Using essentially the same procedure, 11B was prepared.

| Example | Structure | $^1$H NMR | MS (M + H)$^+$ |
|---|---|---|---|
| 11A | (structure shown) | (CDCl$_3$) δ 7.24 (m, 2H), 7.22 (m, 1H), 6.09 (m, 1H), 4.73 (m, 1H), 4.47 (m, 1H), 4.32 (m, 1H), 4.04 (m, 1H), 3.86 (m, 1H), 3.14 (m, 1H), 2.68 (s, 3H), 2.4-2.65 (m, 4H), 2.10 (s, 3H), 2.06 (m, 2H), 1.69 (m, 3H), 1.52 (m, 2H). | 424 |
| 11B | (structure shown) | (CDCl$_3$) δ 7.23 (m, 2H), 7.20 (m, 1H), 6.07 (m, 1H), 4.74 (m, 1H), 4.46 (m, 1H), 4.34 (m, 1H), 4.04 (m, 1H), 3.90 (m, 1H), 3.08 (m, 1H), 2.67 (s, 3H), 2.4-2.65 (m, 4H), 2.34 (q, J = 7.2 Hz, 2H), 2.06 (m, 2H), 1.69 (m, 3H), 1.49 (m, 2H), 1.13 (t, J = 7.2 Hz, 3H). | 438 |

EXAMPLE 12A

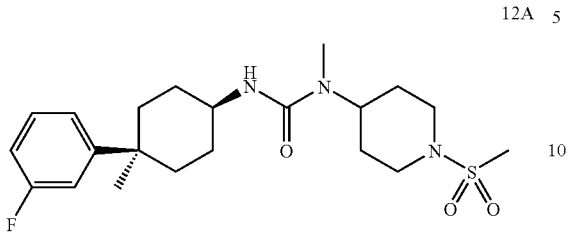

Step 1. Synthesis of 69

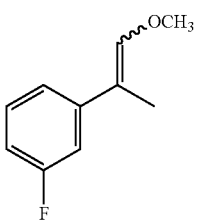

To a suspension of methoxymethylenetriphenylphosphonium chloride (16.4 g, 47.8 mmol) in THF (30 ml) in an ice-water bath was added potassium t-butoxide (6.72 g, 60.0 mmol) in t-butanol (40 ml). The mixture was stirred at 0° C. for 1 hour. 3'-Fluoroacetophenone (5.00 g, 36.2 mmol) was added and the mixture was stirred at RT for 3 hours. The reaction was diluted with water (100 ml) and extracted with ether (2×100 ml). The organic portion was washed with brine, dried (MgSO$_4$), concentrated, and purified by column chromatography (Hexanes) to give 69 (4.80 g, 80%). $^1$H-NMR (CDCl$_3$) δ 7.2-7.5 (m, 2H), 7.08 (m, 0.5H), 6.99 (m, 0.5H), 6.86 (m, 1H), 6.46 (m, 0.5H), 6.16 (m, 0.5H), 3.74 (s, 1.5H), 3.71 (s, 1.5H), 1.97 (m, 1.5H), 1.91 (m, 1.5H).

Step 2. Synthesis of 70

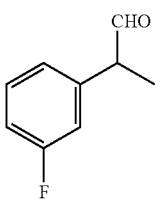

A solution of 69 (4.80 g, 28.9 mmol) and p-toluenesulfonic acid (0.338 g, 1.78 mmol) in dioxane (90 ml) and water (18 ml) was refluxed for 20 hours. The mixture was diluted with water (100 ml) and extracted with ether (2×200 ml). The combined organic portion was washed with brine, dried (MgSO$_4$), and purified by column chromatography (Hexanes gradient to EtOAc:Hexanes 1:100) to give 70 (1.90 g, 43%). $^1$H-NMR (CDCl$_3$) δ 9.68 (d, J=1.6 Hz, 1H), 7.35 (m, 1H), 7.01 (m, 2H), 6.93 (m, 1H), 3.64 (m,1H), 1.45 (d, J=7.6 Hz, 3H).

Step 3. Synthesis of 71

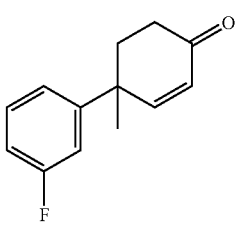

To a solution of 70 (1.90 g, 12.5 mmol) in EtOH (120 ml) and ether (60 ml) in an ice-water bath were added potassium hydroxide (0.21 g, 3.7 mmol) and methyl vinyl ketone (1.31 g, 18.7 mmol). The mixture was then warmed to RT and stirred for 16 hours. The mixture was neutralized with 5% citric acid, concentrated, and partitioned between CH$_2$Cl$_2$ (2×150 ml) and aqueous sodium bicarbonate. The combined organic portion was washed with brine, dried (MgSO$_4$), and purified by column chromatography (Hexanes gradient to EtOAc:Hexanes 1:20) to give 71 (2.00 g, 78%). MS m/e 205 (M+H)$^+$.

Step 4. Synthesis of 72 and 73

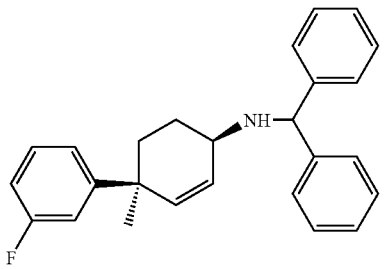

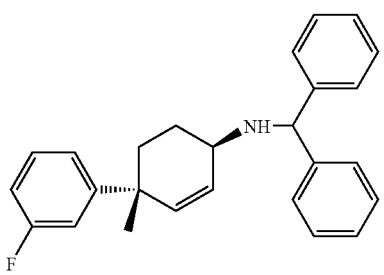

A mixture of 71 (1.02 g, 5.00 mmol), aminodiphenylmethane (1.10 g, 6.00 mmol), and sodium triacetoxyborohydride (2.56 g, 12.1 mmol) in dichloroethane (150 ml) was stirred at RT for 48 hours. The mixture was diluted with CH$_2$Cl$_2$ (150 ml) and washed with conc. NH$_4$OH (100 ml). The organic portion was washed with brine, dried (K$_2$CO$_3$), and purified by column chromatography (Hexanes gradient to EtOAc:Hexanes 1:200) to give 72 (0.960 g, 52%) and 73 (0.320 g, 18%).

72 $^1$H-NMR (CDCl$_3$) δ 7.42 (m, 3H), 7.0-7.35 (m, 1OH), 6.86 (m, 1H), 5.97 (m, 1H), 5.70 (m, 1H), 5.06 (s, 1H), 3.11 (m, 1H), 1.90 (m, 2H), 1.57 (m, 2H), 1.31 (s, 3H), 1.21 (m, 1H).

73 ¹H-NMR (CDCl₃) δ 7.42 (m, 3H), 7.15-7.35 (m, 8H), 7.05 (m, 2H), 6.85 (m, 1H), 5.97 (m, 1H), 5.70 (m, 1H), 5.06 (s, 1H), 3.09 (m, 1H), 1.4-2.0 (m, 4H), 1.38 (s, 3H), 1.21 (m, 1H).

Step 5. Synthesis of 74

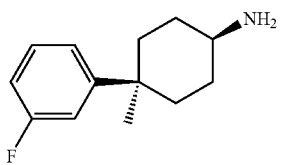

A mixture of 72 (0.660 g, 1.78 mmol), ammonium formate (1.90 g, 30.2 mmol), and 10% Pd/C (0.120 g) in CH₃OH (50 ml) was stirred at RT for 2 days. The mixture was filtered and concentrated. The residue was taken up in CH₂Cl₂ (150 ml) and washed with conc. NH₄OH (20 ml), saturated sodium bicarbonate, and brine. The organic portion was dried (K₂CO₃), concentrated, and purified by column chromatography (CH₂Cl₂ gradient to 2M NH₃/CH₃OH: CH₂Cl₂ 1:20) to give 74 (0.400 g, 100%). MS m/e 208 (M+H)⁺.

Step 6

To an ice-cooled solution of 74 (0.041 g, 0.20 mmol) and pyridine (200 µl, 2.45 mmol) in THF (5 ml) was added N,N'-disuccinimidyl carbonate (0.072 g, 0.28 mmol). The mixture was stirred at RT for 6 hours. N-Methyl-1-(methylsulfonyl)-4-piperidineamine (0.042 g, 0.22 mmol) was added at 0° C. and the mixture was stirred at RT for 16 hours. The mixture was diluted with CH₂Cl₂ (50 ml) and washed with 1N NaOH (20 ml), 1N HCl (20 ml), saturated sodium bicarbonate, and brine sequentially. The organic portion was dried (MgSO₄), concentrated, and purified by PTLC (CH₃OH:CH₂Cl₂ 1:20) to give 12A (0.045 g, 53%).

Using essentially the same procedure, 12B and 12C were prepared from 74.

Using essentially the same procedure, 12D, 12E, and 12F were prepared from 73.

| Example | | ¹H NMR | MS (M + H)⁺ |
|---|---|---|---|
| 12A | | (CDCl₃) δ 7.30 (m, 1H), 7.14 (m, 1H), 7.05 (m, 1H), 6.89 (m, 1H), 4.34 (m, 1H), 4.02 (m, 1H), 3.86 (m, 2H), 3.74 (m, 1H), 2.77 (s, 3H), 2.72 (m, 2H), 2.61 (s, 3H), 2.29 (m, 2H), 1.85 (m, 2H), 1.5-1.8 (m, 6H), 1.14 (s, 3H), 1.10 (m, 2H). | 426 |
| 12B | | (CDCl₃) δ 7.30 (m, 1H), 7.14 (m, 1H), 7.05 (m, 1H), 6.89 (m, 1H), 4.33 (m, 1H), 4.03 (m, 1H), 3.87 (m, 2H), 3.74 (m, 1H), 2.94 (q, J = 7.4 Hz, 2H), 2.84 (m, 2H), 2.60 (s, 3H), 2.28 (m, 2H), 1.85 (m, 2H), 1.5-1.8 (m, 6H), 1.34 (t, J = 7.4 Hz, 3H), 1.14 (s, 3H), 1.10 (m, 2H). | 440 |
| 12C | | (CDCl₃) δ 7.30 (m, 1H), 7.14 (m, 1H), 7.05 (m, 1H), 6.89 (m, 1H), 4.70 (m, 1H), 4.40 (m, 1H), 4.01 (m, 1H), 3.83 (m, 1H), 3.74 (m, 1H), 3.11 (m, 1H), 2.57 (s, 3H), 2.54 (m, 1H), 2.28 (m, 2H), 2.08 (s, 3H), 1.87 (m, 2H), 1.4-1.8 (m, 6H), 1.14 (s, 3H), 1.10 (m, 2H). | 390 |
| 12D | | (CDCl₃) δ 7.27 (m, 1H), 7.15 (m, 1H), 7.06 (m, 1H), 6.88 (m, 1H), 4.40 (m, 1H), 4.31 (m, 1H), 3.88 (m, 2H), 3.68 (m, 1H), 2.79 (s, 3H), 2.76 (m, 2H), 2.74 (s, 3H), 1.4-2.0 (m, 11H), 1.26 (s, 3H), 1.20 (m, 1H). | 426 |

-continued

| Example | | ¹H NMR | MS (M + H)⁺ |
|---|---|---|---|
| 12E | | (CDCl₃) δ 7.27 (m, 1H), 7.15 (m, 1H), 7.06 (m, 1H), 6.88 (m, 1H), 4.40 (m, 1H), 4.29 (m, 1H), 3.91 (m, 2H), 3.66 (m, 1H), 2.96 (q, J = 7.4 Hz, 2H), 2.86 (m, 2H), 2.73 (s, 3H), 1.92 (m, 2H), 1.81 (m, 4H), 1.71 (m, 4H), 1.49 (m, 2H), 1.36 (t, J = 7.4 Hz, 3H), 1.26 (s, 3H). | 440 |
| 12F | | (CDCl₃) δ 7.27 (m, 1H), 7.15 (m, 1H), 7.06 (m, 1H), 6.88 (m, 1H), 4.73 (m, 1H), 4.47 (m, 1H), 4.28 (m, 1H), 3.86 (m, 1H), 3.68 (m, 1H), 3.14 (m, 1H), 2.71 (s, 3H), 2.57 (m, 1H), 2.10 (s, 3H), 1.93 (m, 2H), 1.81 (m, 3H), 1.68 (m, 3H), 1.51 (m, 4H), 1.26 (s, 3H). | 390 |

Example 13A

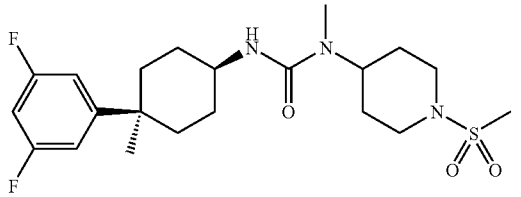

Step 1. Synthesis of 75

To an ice-cooled suspension of methoxymethylenetriphenylphosphonium chloride (13.2 g, 38.4 mmol) in THF (30 ml) was added potassium t-butoxide (5.38 g, 48.0 mmol) in t-butanol (40 ml). The mixture was stirred at 0° C. for 1.5 hours. 3',5'-Difluoroacetophenone (5.00 g, 32.0 mmol) was added and the mixture was stirred at RT for 16 hours. The reaction was diluted with water (100 ml) and extracted with ether (2×200 ml). The organic portion was washed with brine, dried (Na₂SO₄), concentrated, and purified by column chromatography (Hexanes) to give 75 (4.80 g, 68%). ¹H-NMR (CDCl₃) δ 7.17 (m, 1H), 3 6.79 (m, 1H), 6.61 (m, 1H), 6.49 (m, 0.5H), 6.20 (m, 0.5H), 3.75 (s, 1.5H). 3.73 (s, 1.5H), 1.93 (m, 1.5H), 1.88 (m, 1.5H).

Step 2. Synthesis of 76

A solution of 75 (4.80 g, 26.1 mmol) and p-toluenesulfonic acid (0.338 g, 1.78 mmol) in dioxane (90 ml) and water (18 ml) was refluxed for 20 hours. The mixture was diluted with water (100 ml) and extracted with ether (2×200 ml). The combined organic portion was washed with brine, dried (Na₂SO₄), filtered and purified by column chromatography (Hexanes gradient to EtOAc:Hexanes 1:100) to give 76 (1.80 g, 41%). ¹H-NMR (CDCl₃) δ 9.66 (d, J=1.2 Hz, 1H), 6.74 (m, 3H), 3.63 (m, 1H), 1.45 (d, J=6.8 Hz, 3H).

Step 3. Synthesis of 77

To a solution of 76 (1.80 g, 10.6 mmol) in EtOH (120 ml) and ether (60 ml) in an ice-water bath were added potassium hydroxide (0.178 g, 3.17 mmol) and methyl vinyl ketone (1.11 g, 15.8 mmol). The mixture was then warmed to RT and stirred for 16 hours. The mixture was neutralized with 5% citric acid, concentrated, and partitioned between CH$_2$Cl$_2$ (2×150 ml) and aqueous sodium bicarbonate. The combined organic portion was washed with brine, dried (Na$_2$SO$_4$), and purified by column chromatography (Hexanes gradient to EtOAc:Hexanes 1:20) to give 77 (1.50 g, 64%). MS m/e 223 (M+H)$^+$.

Step 4. Synthesis of 78 and 79

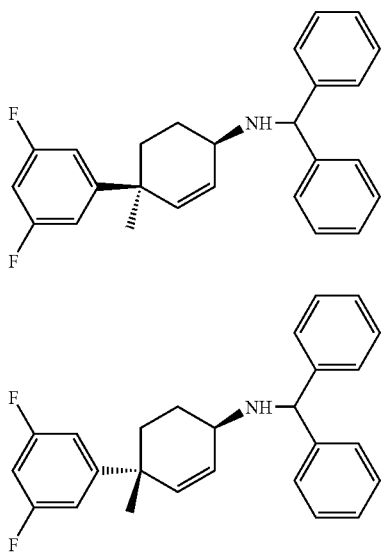

A mixture of 77 (1.50 g, 6.76 mmol), aminodiphenylmethane (1.49 g, 8.11 mmol), and sodium triacetoxyborohydride (3.46 g, 16.4 mmol) in dichloroethane (150 ml) was stirred at RT for 18 hours. The mixture was diluted with CH$_2$Cl$_2$ (150 ml) and washed with conc. NH$_4$OH (100 ml). The organic portion was dried (K$_2$CO$_3$) and purified by column chromatography (Hexanes gradient to EtOAc:Hexanes 1:33) to give 78 (0.440 g, 16%) and 79 (0.322 g, 12%).

78 $^1$H-NMR (CDCl$_3$) δ 7.42 (m, 4H), 7.30 (m, 4H), 7.21 (m, 2H), 6.87 (m, 2H), 6.62 (m, 1H), 5.98 (m, 1H), 5.67 (m, 1H), 5.06 (s, 1H), 3.12 (m, 1H), 1.88 (m, 2H), 1.60 (m, 1H), 1.29 (s, 3H), 1.20 (m, 2H).

79 $^1$H-NMR (CDCl$_3$) δ 7.46 (m, 4H), 7.32 (m, 4H), 7.23 (m, 2H), 6.83 (m, 2H), 6.62 (m, 1H), 5.99 (m, 1H), 5.69 (m, 1H), 5.08 (s, 1H), 3.10 (m, 1H), 1.70 (m, 4H), 1.50 (m, 1H), 1.38 (s, 3H).

Step 5. Synthesis of 80

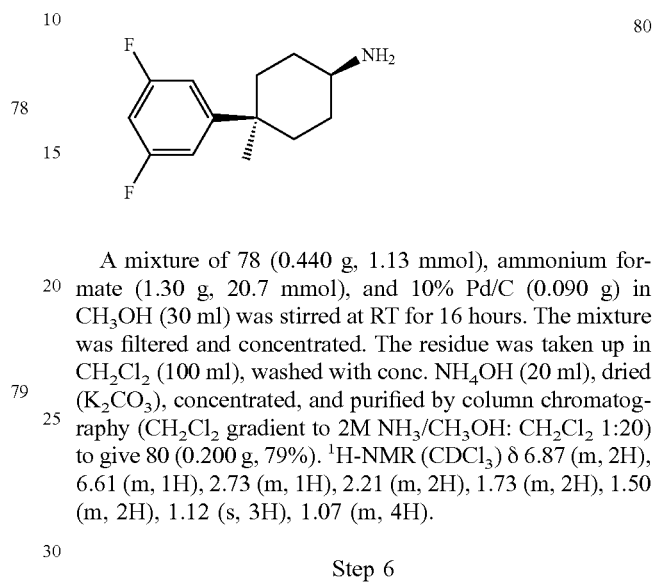

A mixture of 78 (0.440 g, 1.13 mmol), ammonium formate (1.30 g, 20.7 mmol), and 10% Pd/C (0.090 g) in CH$_3$OH (30 ml) was stirred at RT for 16 hours. The mixture was filtered and concentrated. The residue was taken up in CH$_2$Cl$_2$ (100 ml), washed with conc. NH$_4$OH (20 ml), dried (K$_2$CO$_3$), concentrated, and purified by column chromatography (CH$_2$Cl$_2$ gradient to 2M NH$_3$/CH$_3$OH: CH$_2$Cl$_2$ 1:20) to give 80 (0.200 g, 79%). $^1$H-NMR (CDCl$_3$) δ 6.87 (m, 2H), 6.61 (m, 1H), 2.73 (m, 1H), 2.21 (m, 2H), 1.73 (m, 2H), 1.50 (m, 2H), 1.12 (s, 3H), 1.07 (m, 4H).

Step 6

To an ice-cooled solution of 80 (0.045 g, 0.20 mmol) and pyridine (200 μl, 2.45 mmol) in THF (5 ml) was added N,N'-disuccinimidyl carbonate (0.072 g, 0.28 mmol). The mixture was stirred at RT for 4 hours. N-Methyl-1-(methylsulfonyl)-4piperidineamine (0.042 g, 0.22 mmol) was added at 0° C. and the mixture was stirred at RT for 16 hours. The mixture was diluted with CH$_2$Cl$_2$ (50 ml) and washed with 1N NaOH (20 ml), 1N HCl (20 ml), saturated sodium bicarbonate, and brine sequentially. The organic portion was dried (MgSO$_4$), concentrated, and purified by PTLC (CH$_3$OH:CH$_2$Cl$_2$ 1:20) to give 13A (0.005 g, 6%).

Using essentially the same procedure, 13B was prepared from 80.

Using essentially the same procedure, 13C and 13D were prepared from 79.

| Example | | $^1$H NMR | MS (M + H)$^+$ |
|---|---|---|---|
| 13A | | (CDCl$_3$) δ 6.87 (m, 2H), 6.64 (m, 1H), 4.34 (m, 1H), 4.05 (m, 1H), 3.86 (m, 2H), 3.72 (m, 1H), 2.77 (s, 3H), 2.72 (m, 2H), 2.62 (s, 3H), 2.22 (m, 2H), 1.87 (m, 2H), 1.5–1.8 (m, 6H), 1.13 (s, 3H), 1.10 (m, 2H). | 444 |

-continued

| Example | | $^1$H NMR | MS (M + H)$^+$ |
|---|---|---|---|
| 13B | 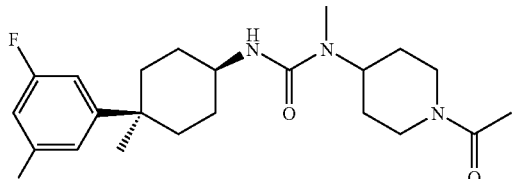 | (CDCl$_3$) δ 6.85 (m, 2H), 6.64 (m, 1H), 4.69 (m, 1H), 4.40 (m, 1H), 4.03 (m, 1H), 3.84 (m, 1H), 3.73 (m, 1H), 3.11 (m, 1H), 2.59 (s, 3H), 2.55 (m, 1H), 2.22 (m, 2H), 2.08 (s, 3H), 1.87 (m, 2H), 1.4-1.7 (m, 6H), 1.13 (s, 3H), 1.09 (m, 2H). | 408 |
| 13C | 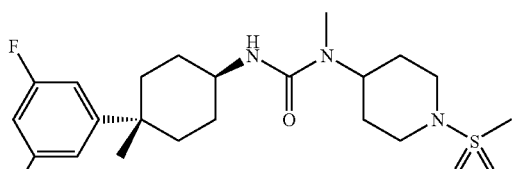 | (CDCl$_3$) δ 6.87 (m, 2H), 6.63 (m, 1H), 4.39 (m, 1H), 4.29 (m, 1H), 3.89 (m, 2H), 3.66 (m, 1H), 2.79 (s, 3H), 2.76 (m, 2H), 2.74 (s, 3H), 1.94 (m, 2H), 1.6-1.9 (m, 8H), 1.48 (m, 2H), 1.25 (s, 3H). | 444 |
| 13D | 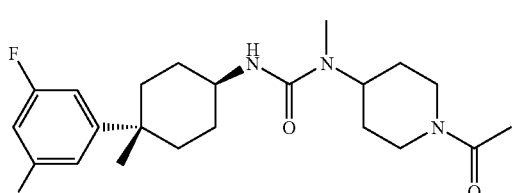 | (CDCl$_3$) δ 6.87 (m, 2H), 6.63 (m, 1H), 4.74 (m, 1H), 4.47 (m, 1H), 4.27 (m, 1H), 3.87 (m, 1H), 3.68 (m, 1H), 3.14 (m, 1H), 2.70 (s, 3H), 2.58 (m, 1H), 2.10 (s, 3H), 1.94 (m, 2H), 1.4-1.9 (m, 10H), 1.25 (s, 3H). | 408 |

What is claimed is:

1. A compound represented by the structural formula

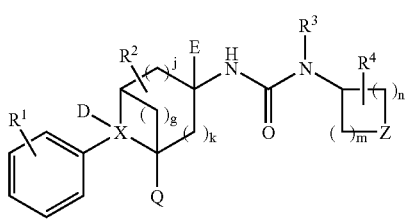

I or a pharmaceutically acceptable salt thereof, wherein:
X is independently N or C;
Z is independently NR$^8$;
D is independently H, —OH, -alkyl or substituted -alkyl with the proviso that when X is N, D and the X-D bond are absent;
E is independently H, -alkyl or substituted -alkyl, or D and E can independently be joined together via a —(CH$_2$)$_p$- bridge;
Q is independently H, -alkyl or substituted -alkyl, or D, X, Q and the carbon to which Q is attached can jointly form a 3 to 7-membered ring;
g, j, k, m and n can be the same or different and are independently selected;
g is 0;
j and k are independently 0 to 3 such that the sum of j and k is 0, 1, 2 or 3;
m and n are independently 0 to 3 such that the sum of m and n is 1, 2, 3, 4 or 5;
p is 1 to 3;
R$^1$ is 1 to 5 substituents which can be the same or different, each R$^1$ being independently selected from the group consisting of hydrogen, hydroxy, halogen, haloalkyl, -alkyl, substituted -alkyl, -cycloalkyl, CN, alkoxy, cycloalkoxy, alkylthio, cycloalkylthio, —NR$^5$R$^6$, —NO$_2$, —CONR$^5$R$^6$, —NR$^5$COR$^6$, —NR$^5$CONR$^5$R$^6$ where the two R$^5$ moieties can be the same or different, —NR$^6$C(O)OR$^7$, —C(O)OR$^6$, —SOR$^7$, —SO$_2$R$^7$, —SO$_2$NR$^5$R$^6$, aryl and heteroaryl;
R$^2$ is 1 to 6 substituents which can be the same or different, each R$^2$ being independently selected from the group consisting of hydrogen, -alkyl, substituted -alkyl, alkoxy, and hydroxy, with the proviso that when X is N and R$^2$ is hydroxy or alkoxy, R$^2$ is not directly attached to a carbon adjacent to X;
R$^3$ is independently hydrogen, -alkyl or substituted -alkyl;
R$^4$ is 1 to 6 substituents which can be the same or different, each R$^4$ being independently selected from hydrogen, -alkyl, substituted -alkyl, alkoxy, and hydroxy, with the proviso that when Z is NR$^8$ and R$^4$ is hydroxy or alkoxy, R$^4$ is not directly attached to a carbon adjacent to the NR$^8$;
R$^5$ and R$^6$ are independently hydrogen, -alkyl, substituted -alkyl or -cycloalkyl;
R$^7$ is independently -alkyl, substituted -alkyl or -cycloalkyl;
R$^8$ is independently selected from the group consisting of hydrogen, -alkyl, substituted -alkyl, -cycloalkyl, -alkylcycloalkyl, aryl, heteroaryl, aralkyl, heteroaralkyl, —SO$_2$R$^{10}$, —SO$_2$NR$^5$R$^{11}$, —C(O)R$^{11}$, —C(O)NR$^5$R$^{11}$ and —C(O)OR$^{10}$;
R$^9$ is independently hydrogen, -alkyl, substituted -alkyl, hydroxy, alkoxy, —NR$^5$R$^{11}$, aryl, or heteroaryl; or R$^3$ and R[9] can be joined together and with the carbon to which they are attached form a carbocyclic or heterocyclic ring having 3 to 7 ring atoms;

R[10] is -alkyl, substituted -alkyl, -cycloalkyl, -alkylcycloalkyl, aryl or heteroaryl; and R[11] is independently hydrogen, -alkyl, substituted -alkyl, -cycloalkyl, aryl or heteroaryl.

2. The compound of claim 1 or a pharmaceutically acceptable salt thereof, wherein R[1] is 1 to 5 substituents which can be the same or different, each R[1] being independently selected from the group consisting of Cl, Br, I or F;

X is N;

D is absent and the X-D bond is absent;

E is H;

g is 0;

j is 1;

k is 1;

m is 2;

n is 2;

R[2] is H;

R[3] is methyl;

R[4] is H; and

Z is NR[8], where R[8] is independently selected from the group consisting of hydrogen, -alkyl, substituted -alkyl, -cycloalkyl, -alkylcycloalkyl, aryl, heteroaryl, aralkyl, heteroaralkyl, —SO$_2$R[10], —SO$_2$NR[5]R[11], —C(O)R[11], —C(O)NR[5]R[11] and —C(O)OR[10].

3. A compound represented by the structural formula

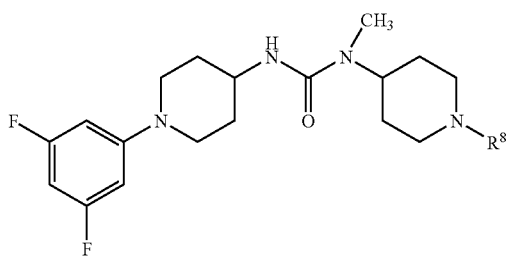

II or a pharmaceutically acceptable salt thereof, wherein R[8] is defined in the following table:

| R[8] |
| --- |
| —COCH$_3$ |
| —COCH$_2$CH$_3$ |
| —CO—⊲ |
| —COCH(CH$_3$)$_2$ |
| —CO(CH$_2$)$_2$CH$_3$ |
| —COOC(CH$_3$)$_3$ |
| —SO$_2$CH$_3$ |
| —SO$_2$CH$_2$CH$_3$ |
| —SO$_2$—⊲ |
| —SO$_2$CH(CH$_3$)$_2$ |
| —SO$_2$(CH$_2$)$_2$CH$_3$ |
| —SO$_2$Ph. |

4. A compound of claim 1 selected from the group consisting of

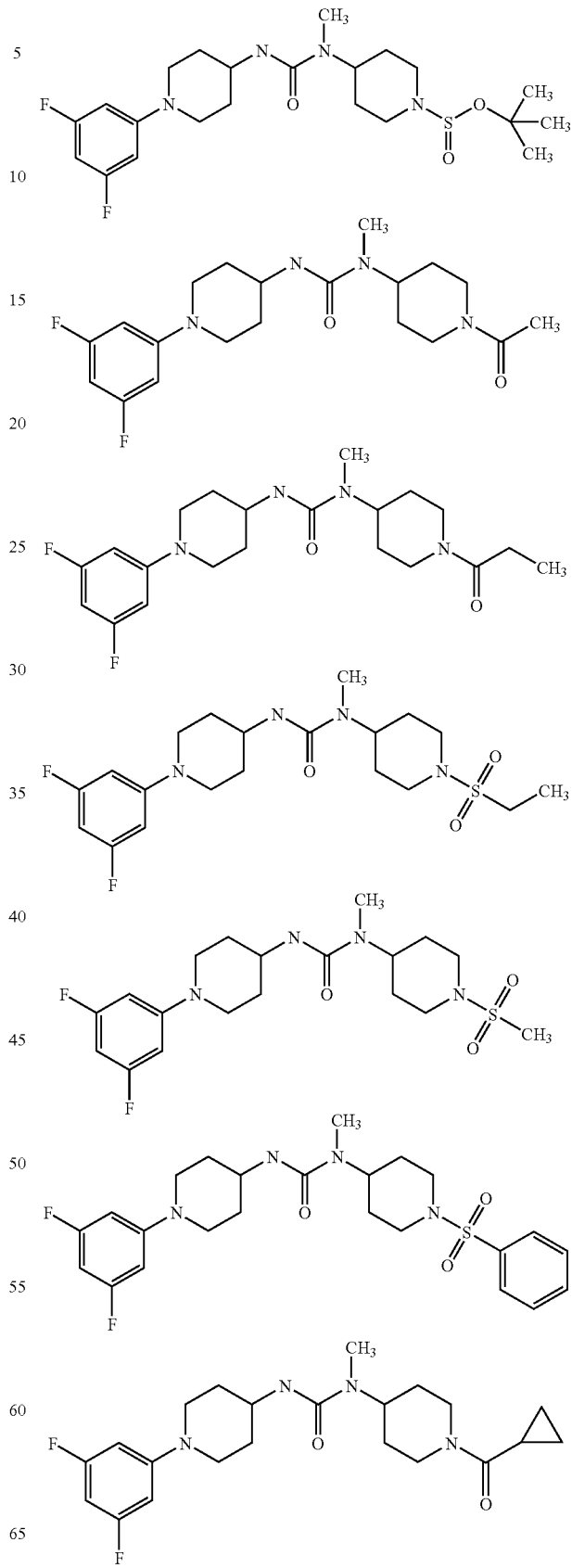

-continued
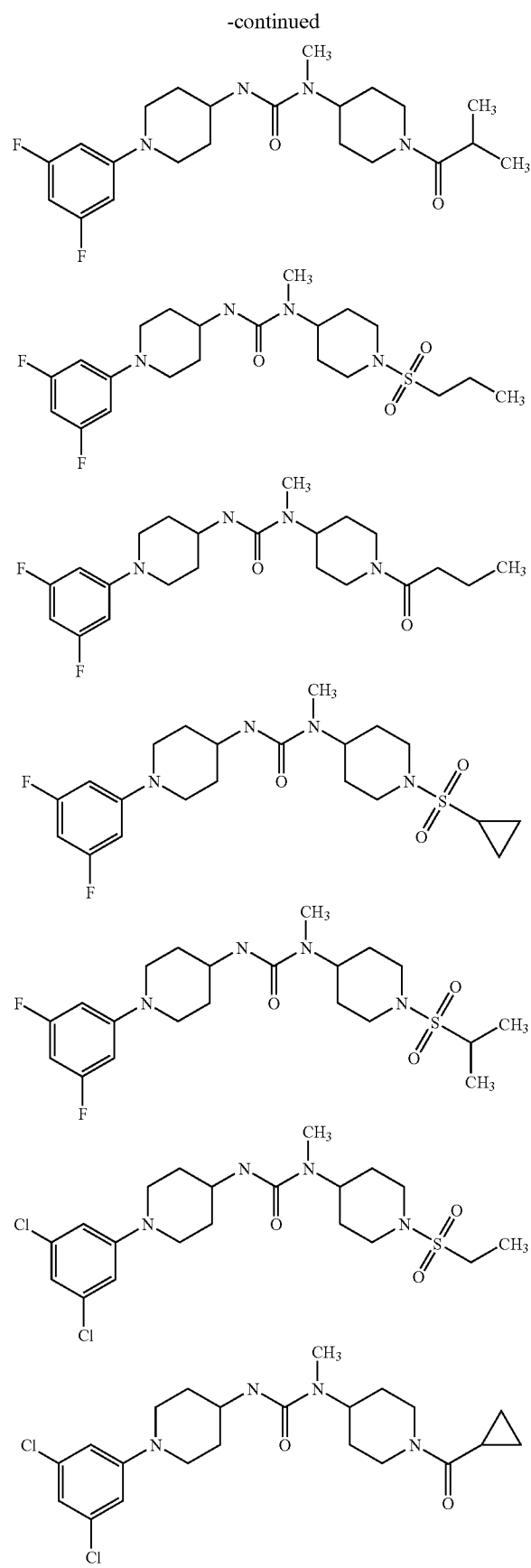
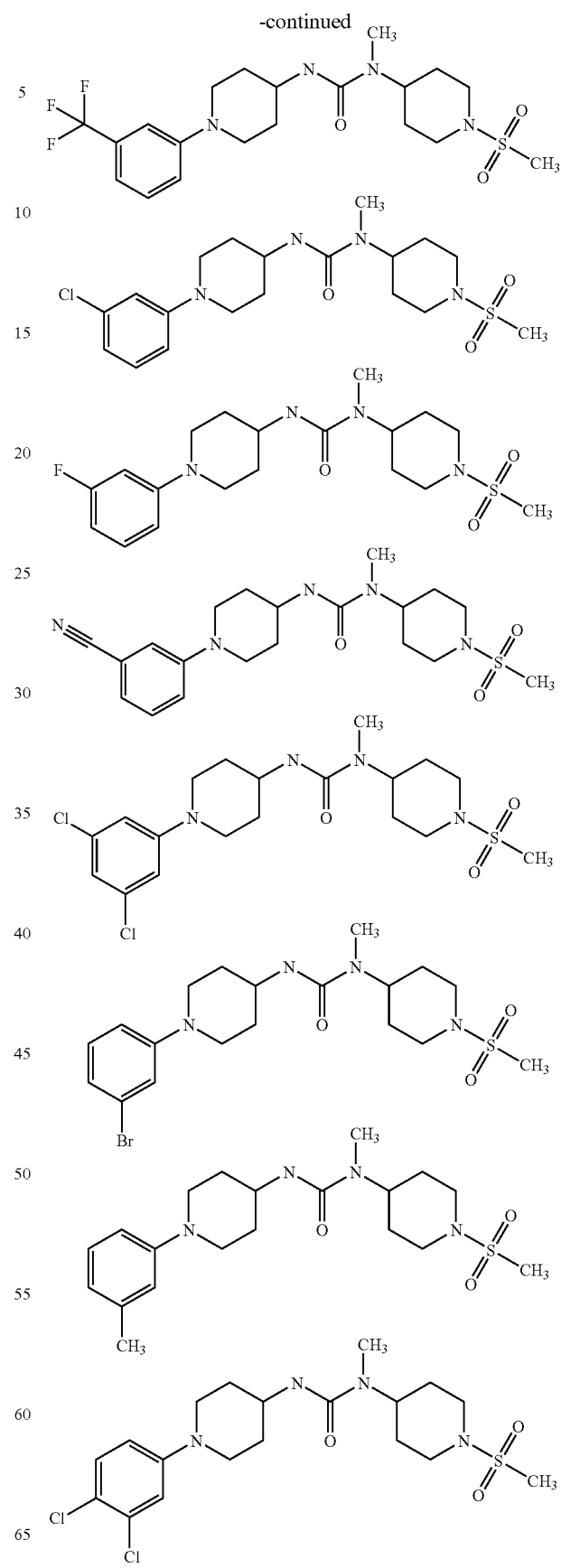

-continued
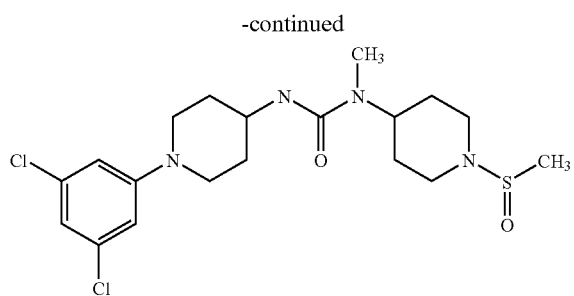
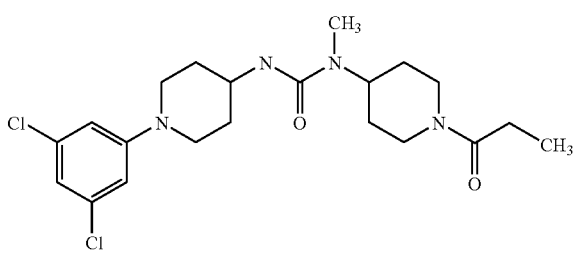
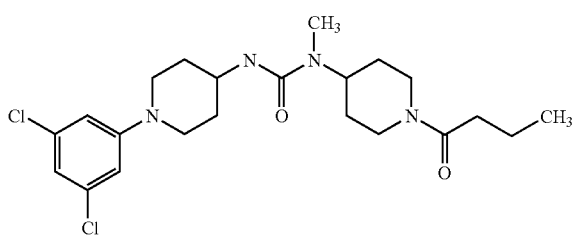
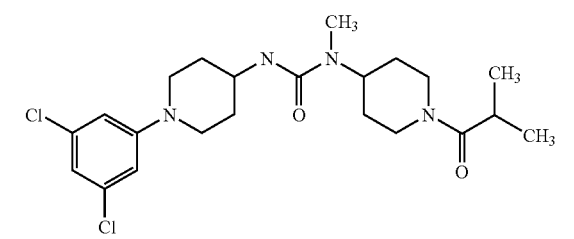
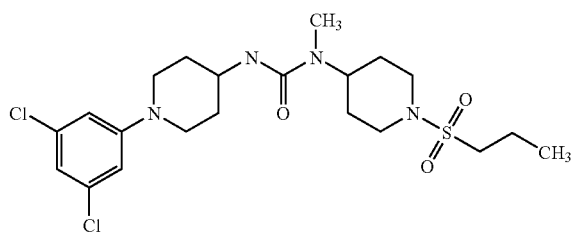
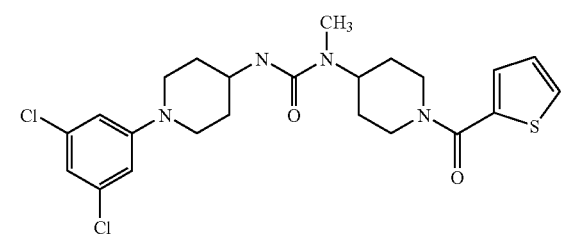
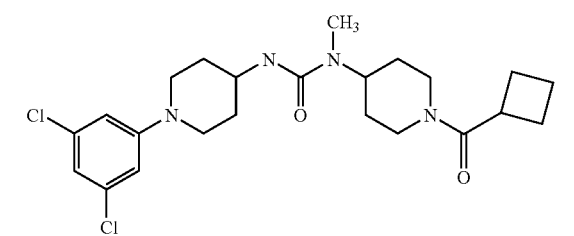
-continued
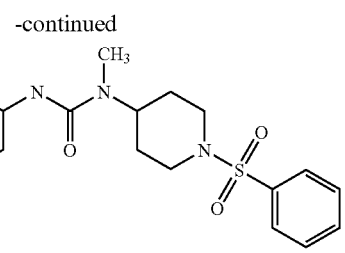
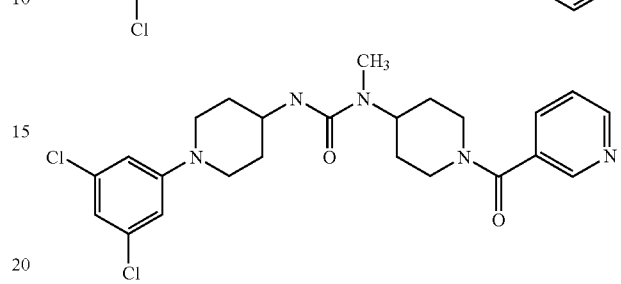
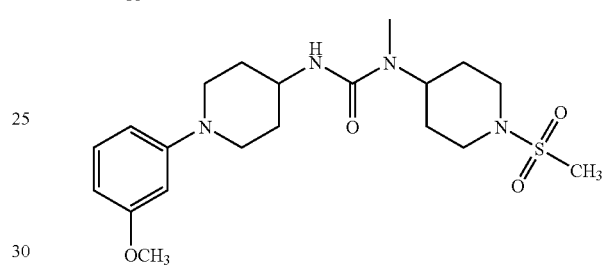
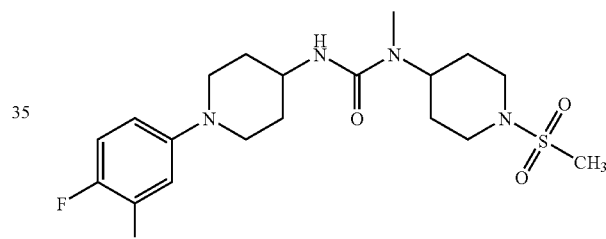
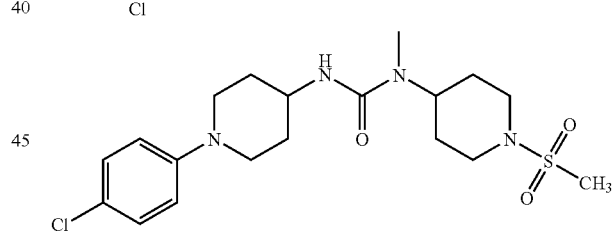
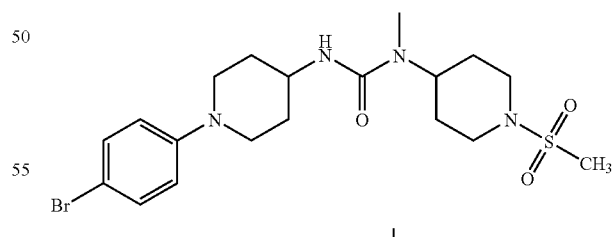
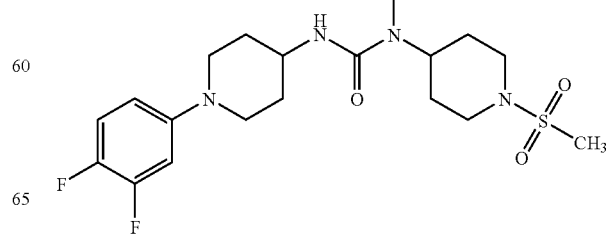

-continued

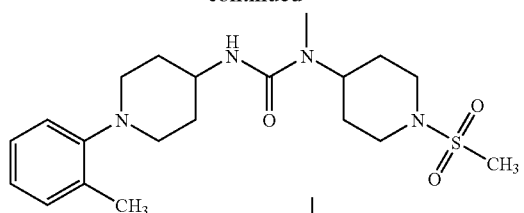

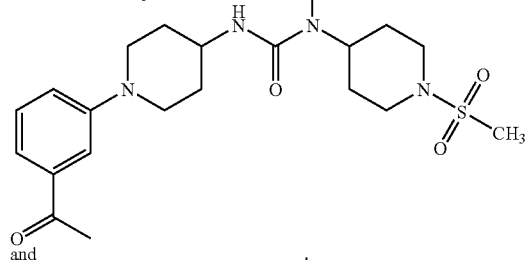

and

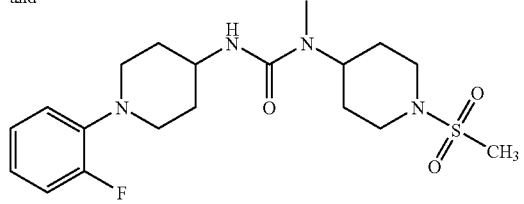

or a pharmaceutically acceptable salt of said compound.

5. A pharmaceutical composition comprising a therapeutically effective amount of a compound of claim 1 in combination with a pharmaceutically acceptable carrier.

6. A method of treating obesity or diabetes comprising administering an effective amount of a compound of claim 1 to a mammal in need of such treatment.

7. A pharmaceutical unit dosage composition, which comprises an effective amount of a compound as, defined in claim 1 and a pharmaceutically acceptable carrier thereof.

8. A method of treating obesity or diabetes comprising administering to a mammal in need of such treatment a therapeutically effective amount of a compound of claim 7 or a pharmaceutically acceptable salt of said compound.

9. A pharmaceutical composition made by combining an effective amount of the compound of claim 1 and a pharmaceutically acceptable carrier therefor.

10. A process for making a pharmaceutical composition comprising combining an effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 7,304,076 B2
APPLICATION NO. : 10/692559
DATED : December 4, 2007
INVENTOR(S) : Andrew Stamford It is certified that error appears in the above-identified patent and that said Letters Patent is hereby corrected as shown below:

In the Title:

Page 1, left side column, No. (54): Please correct the Title to:

-- New Neuropeptide Y Y5 Receptor Antagonists --

In the Claims:

Claim 1, col. 113, line 51: Please correct "X is independently N or C;" to -- X is N; --

Claim 4, col. 119, lines 5-10: Please correct the structure:

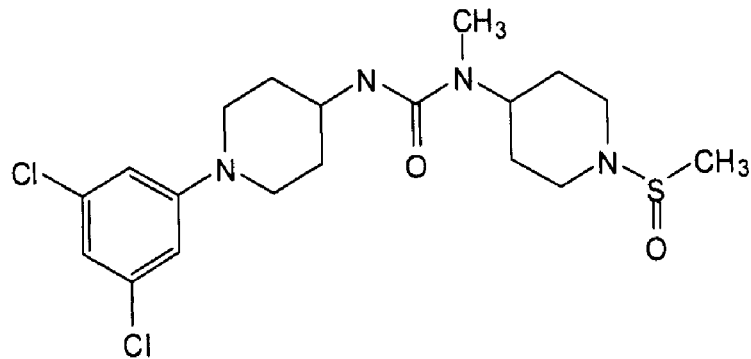

to

UNITED STATES PATENT AND TRADEMARK OFFICE
CERTIFICATE OF CORRECTION

PATENT NO.         : 7,304,076 B2
APPLICATION NO. : 10/692559
DATED              : December 4, 2007
INVENTOR(S)      : Andrew Stamford It is certified that error appears in the above-identified patent and that said Letters Patent is hereby corrected as shown below:

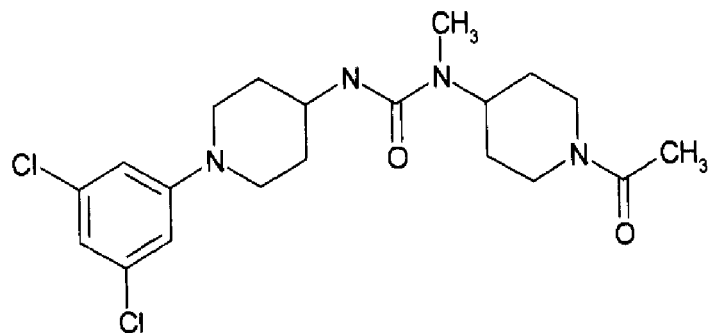

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.         : 7,304,076 B2                                              Page 1 of 1
APPLICATION NO.    : 10/692559
DATED              : December 4, 2007
INVENTOR(S)        : Andrew W. Stamford et al.

It is certified that error appears in the above-identified patent and that said Letters Patent is hereby corrected as shown below:

<u>Title Page,</u>
Item [54], Title, the word "NEW" (as inserted by Certificate of Correction issued June 17, 2008) should be deleted and title is to reinstate to read --NEUROPEPTIDE Y Y5 RECEPTOR ANTAGONISTS--.

Signed and Sealed this

Twenty-second Day of July, 2008

JON W. DUDAS
*Director of the United States Patent and Trademark Office*